United States Patent
Kim et al.

(10) Patent No.: US 12,358,883 B2
(45) Date of Patent: Jul. 15, 2025

(54) LIGHT-EMITTING DEVICE AND ELECTRONIC APPARATUS INCLUDING THE SAME

(71) Applicant: Samsung Display Co., Ltd., Yongin-si (KR)

(72) Inventors: Seulong Kim, Yongin-si (KR); Hyein Jeong, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 845 days.

(21) Appl. No.: 17/551,077

(22) Filed: Dec. 14, 2021

(65) Prior Publication Data

US 2022/0223789 A1 Jul. 14, 2022

(30) Foreign Application Priority Data

Jan. 4, 2021 (KR) ........................ 10-2021-0000446

(51) Int. Cl.
| | |
|---|---|
| *H10K 50/13* | (2023.01) |
| *H10K 85/40* | (2023.01) |
| *H10K 85/60* | (2023.01) |
| *H10K 50/11* | (2023.01) |
| *H10K 50/12* | (2023.01) |
| *H10K 50/155* | (2023.01) |
| *H10K 50/16* | (2023.01) |
| *H10K 50/17* | (2023.01) |
| *H10K 71/00* | (2023.01) |
| *H10K 101/10* | (2023.01) |

(52) U.S. Cl.
CPC .......... *H10K 85/633* (2023.02); *H10K 85/40* (2023.02); *H10K 85/624* (2023.02); *H10K 85/626* (2023.02); *H10K 85/636* (2023.02); *H10K 85/6572* (2023.02); *H10K 85/6574* (2023.02); *H10K 85/6576* (2023.02); *H10K 50/11* (2023.02); *H10K 50/12* (2023.02); *H10K 50/13* (2023.02); *H10K 50/155* (2023.02); *H10K 50/16* (2023.02); *H10K 50/171* (2023.02); *H10K 71/00* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 9,040,172 B2 | 5/2015 | Parham et al. | |
| 9,172,055 B2 | 10/2015 | Kim et al. | |
| 10,862,057 B2 | 12/2020 | Kim et al. | |
| 10,930,853 B2 | 2/2021 | Kim et al. | |
| 10,944,056 B2 | 3/2021 | Montenegro et al. | |
| 11,575,087 B1 * | 2/2023 | Toyoshima | ............ H10K 85/40 |
| 2008/0261076 A1 * | 10/2008 | Kwong | ................ H10K 85/381 |
| | | | 546/4 |
| 2013/0207046 A1 | 8/2013 | Pflumm | |
| 2014/0124744 A1 | 5/2014 | Oh | |
| 2015/0228899 A1 | 8/2015 | Kato et al. | |
| 2016/0079542 A1 * | 3/2016 | Itoi | ...................... H10K 85/636 |
| | | | 257/40 |
| 2016/0099417 A1 * | 4/2016 | Sato | ..................... H10K 85/633 |
| | | | 257/40 |
| 2016/0133850 A1 | 5/2016 | Matsuura | |
| 2016/0141510 A1 | 5/2016 | Sasaki et al. | |
| 2016/0155943 A1 * | 6/2016 | Sasaki | ..................... C09K 11/06 |
| 2016/0163982 A1 * | 6/2016 | Ishihara | ............... H10K 85/636 |
| | | | 257/40 |
| 2016/0365515 A1 * | 12/2016 | Suganuma | ......... H10K 85/6574 |
| 2016/0380197 A1 * | 12/2016 | Morimoto | ............ H10K 85/631 |
| | | | 257/40 |
| 2019/0288220 A1 * | 9/2019 | Kim | ..................... H10K 85/655 |
| 2021/0151681 A1 * | 5/2021 | Kang | ................ H10K 85/636 |
| 2022/0173318 A1 * | 6/2022 | Kim | ..................... H10K 85/626 |
| 2023/0006160 A1 * | 1/2023 | Tasaki | ....................... G09F 9/30 |
| 2023/0036664 A1 * | 2/2023 | Toyoshima | ........ H10K 85/6576 |

(Continued)

FOREIGN PATENT DOCUMENTS

| | | | | |
|---|---|---|---|---|
| KR | 10-2014-0104895 A | 8/2014 | | |
| KR | 10-2014-0133572 A | 11/2014 | | |
| KR | 10-2016-0060536 A | 5/2016 | | |
| KR | 10-2017-0061768 A | 6/2017 | | |
| KR | 20170134163 A * | 12/2017 | ............. H01L 51/50 | |
| KR | 10-1932563 B1 | 12/2018 | | |
| KR | 20200082020 A * | 7/2020 | ............. H01L 51/00 | |
| KR | 10-2020-0103611 A | 9/2020 | | |

OTHER PUBLICATIONS

Machine translation of KR-20170134163-A, translation generated Oct. 2024, 42 pages. (Year: 2024).*
Machine translation of KR-20200082080-A, translation generated Oct. 2024, 21 pages. (Year: 2024).*
Mistuhiro Koden "OLED Displays and Lighting", John Wiley & Sons, Ltd, The Atrium, Southern Gate, Chichester, West Sussex, PO19 8SQ, United Kingdom, 2017, 235 pages. (Year: 2017).*
Third Party Observation for application No. EP20210152336.

*Primary Examiner* — Robert S Loewe
(74) *Attorney, Agent, or Firm* — Womble Bond Dickinson (US) LLP

(57) ABSTRACT

A light-emitting device includes a first electrode, a second electrode facing the first electrode, and an interlayer including an emission layer between the first electrode and the second electrode and a hole transport region between the first electrode and the emission layer, wherein the emission layer may include a dopant, the hole transport region may include a first hole transport layer, a second hole transport layer between the first hole transport layer and the emission layer, and a third hole transport layer between the second hole transport layer and the emission layer, the first hole transport layer may include a first compound, the second hole transport layer may include a second compound, the third hole transport layer may include a third compound, and the first to third compounds may each independently be an amine-based compound, but may be different from each other.

20 Claims, 4 Drawing Sheets

(56) References Cited

U.S. PATENT DOCUMENTS

| | | | |
|---|---|---|---|
| 2023/0171977 A1* | 6/2023 | Tasaki | H10K 85/633 |
| | | | 257/40 |
| 2023/0263001 A1* | 8/2023 | Toyoshima | H10K 50/155 |
| | | | 257/40 |
| 2024/0130223 A1* | 4/2024 | Toyoshima | H10K 85/6574 |
| 2024/0130224 A1* | 4/2024 | Toyoshima | H10K 85/615 |
| 2024/0147843 A1* | 5/2024 | Tasaki | H10K 85/633 |

* cited by examiner

LIGHT-EMITTING DEVICE AND ELECTRONIC APPARATUS INCLUDING THE SAME

CROSS-REFERENCE TO RELATED APPLICATION

This application claims priority to and the benefit of Korean Patent Application No. 10-2021-0000446, filed on Jan. 4, 2021, in the Korean Intellectual Property Office, the entire content of which is hereby incorporated by reference.

BACKGROUND

1. Field

One or more embodiments relate to a light-emitting device and an electronic apparatus including the light-emitting device.

2. Description of the Related Art

Organic light-emitting devices from among light-emitting devices are self-emissive devices, and compared to devices in the related art, have wide viewing angles, excellent contrast, and excellent characteristics in terms of luminance, driving voltage, and response speed.

An organic light-emitting device may have a structure in which a first electrode is located on a substrate, and a hole transport region, an emission layer, an electron transport region, and a second electrode are sequentially formed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

SUMMARY

Aspects according to one or more embodiments are directed toward a light-emitting device having excellent light efficiency and an electronic apparatus including the light-emitting device.

Additional aspects will be set forth in part in the description which follows and, in part, will be apparent from the description, or may be learned by practice of the presented embodiments of the disclosure.

According to an embodiment of the disclosure, a light-emitting device includes a first electrode,
a second electrode facing the first electrode, and
an interlayer including an emission layer between the first electrode and the second electrode and a hole transport region between the first electrode and the emission layer,
wherein the emission layer may include a dopant,
the hole transport region may include a first hole transport layer, a second hole transport layer between the first hole transport layer and the emission layer, and a third hole transport layer between the second hole transport layer and the emission layer,
the first hole transport layer may include a first compound,
the second hole transport layer may include a second compound,
the third hole transport layer may include a third compound,
the first to third compounds may each independently be an amine-based compound, but may be different from each other, and
Equation 1 may be satisfied.

$$T_1(HTM3) \geq T_1(D) + 0.3 \text{ eV} \qquad \text{Equation 1}$$

In Equation 1,
$T_1(HTM3)$ is a triplet energy level in electron volt (eV) of the third compound,
$T_1(D)$ is a triplet energy level in electron volt (eV) of the dopant, and
$T_1(HTM3)$ and $T_1(D)$ are values evaluated utilizing the density functional theory (DFT) method of the Gaussian program, which is structure-optimized at the B3LYP/6-31G(d,p) level.

According to another embodiment of the disclosure, an electronic apparatus includes the light-emitting device.

BRIEF DESCRIPTION OF THE DRAWINGS

The above and other aspects, features, and enhancements of certain embodiments of the disclosure will be more apparent from the following description taken in conjunction with the accompanying drawings, in which.

DETAILED DESCRIPTION

Figure 1:
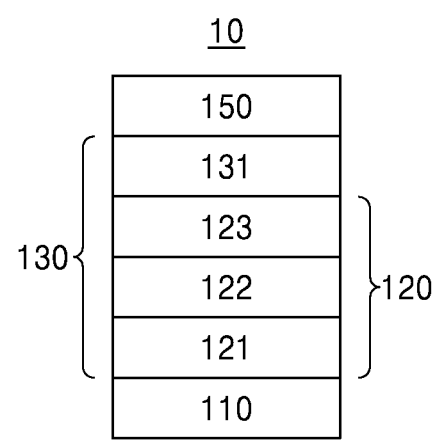
FIG. 1 is a schematic cross-sectional view of a light-emitting device according to an embodiment.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b and c" indicates only a, only b, only c, both a and b, both a and c, both b and c, all of a, b, and c, or variations thereof.

A light-emitting device according to an embodiment of the disclosure includes: a first electrode;
a second electrode facing the first electrode; and
an interlayer including an emission layer between the first electrode and the second electrode and a hole transport region between the first electrode and the emission layer,
wherein the emission layer may include a dopant,
the hole transport region may include a first hole transport layer, a second hole transport layer between the first hole transport layer and the emission layer, and a third hole transport layer between the second hole transport layer and the emission layer,
the first hole transport layer may include a first compound,
the second hole transport layer may include a second compound, the third hole transport layer may include a third compound, the first to third compounds may each independently be an amine-based compound, but may be different from each other, and Equation 1 may be satisfied:

$$T_1(HTM3) \geq T_1(D) + 0.3 \text{ eV} \qquad \text{Equation 1}$$

wherein, in Equation 1, $T_1(HTM3)$ is a triplet energy level in electron volt (eV) of the third compound, $T_1(D)$ is a triplet energy level in electron volt (eV) of the dopant, and $T_1(HTM3)$ and $T_1(D)$ are values evaluated utilizing a density functional theory (DFT) method of a Gaussian program, which is structure-optimized at a B3LYP/6-31G(d,p) level.

In an embodiment, the first to third compounds may each independently be a group represented by Formula 1-1 or Formula 1-2:

Formula 1-1

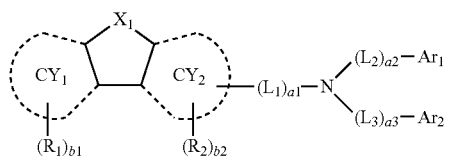

Formula 1-2

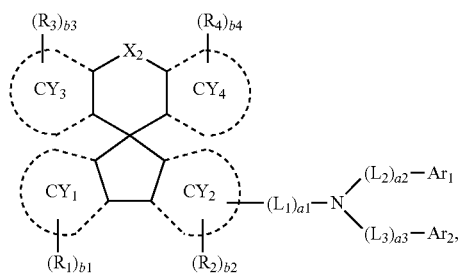

wherein, in Formula 1-1, $X_1$ may be *—$C(Z_{1a})(Z_{1b})$—*', in Formula 1-2, $X_2$ may be a single bond, *—O—*', *—S—*', *—$C(Z_{2a})(Z_{2b})$—*', or *—$N(Z_{2a})(Z_{2b})$—*', in Formulae 1-1 and 1-2, $CY_1$ to $CY_4$ may each independently be a $C_3$-$C_{60}$ carbocyclic group or a $C_1$-$C_{60}$ heterocyclic group, $L_1$ to $L_3$ may each independently be a single bond, a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_6$ heterocyclic group unsubstituted or substituted with at least one $R_{10a}$, a1 to a3 may each independently be an integer from 0 to 5, $Ar_1$ and $Ar_2$ may each independently be a $C_3$-$C_{60}$ carbocyclic group unsubstituted or substituted with at least one $R_{10a}$ or a $C_1$-$C_6$ heterocyclic group unsubstituted or substituted with at least one $R_{10a}$, $R_1$ to $R_4$, $Z_{1a}$, $Z_{1b}$, $Z_{2a}$, and $Z_{2b}$ may each independently be:

hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$B(Q_1)(Q_2)$, —$C(=O)(Q_1)$, —$S(=O)_2(Q_1)$, or —$P(=O)(Q_1)(Q_2)$, b1 to b4 may each independently be an integer from 0 to 10, when b1 is 2 or more, two $R_1(s)$ of two or more $R_1(s)$ may optionally be linked together to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, when b2 is 2 or more, two $R_2(s)$ of two or more $R_2(s)$ may optionally be linked together to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, when b3 is 2 or more, two $R_3(s)$ of two or more $R_3(s)$ may optionally be linked together to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, when b4 is 2 or more, two $R_4(s)$ of two or more $R_4(s)$ may optionally be linked together to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —Si$(Q_{11})(Q_{12})(Q_{13})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_6$ heterocyclic group, a $C_6$-$C_{60}$ aryloxy group, or a $C_6$-$C_{60}$ arylthio group, each unsubstituted or substituted with deuterium, —F, —$C_1$, —Br, —I, a hydroxyl group, a cyano group, a nitro group, a $C_1$-$C_6$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, —$Si(Q_{21})(Q_{22})(Q_{23})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$B(Q_{31})(Q_{32})$, —$C(=O)(Q_{31})$, —$S(=O)_2(Q_{31})$, or —$P(=O)(Q_{31})(Q_{32})$, $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_6$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, and

* and *' each indicate a binding site to a neighboring atom.

In an embodiment, the first compound may be a carbazole-free compound.

In an embodiment, the first compound may not include groups represented by Formulae 2-1 to 2-3:

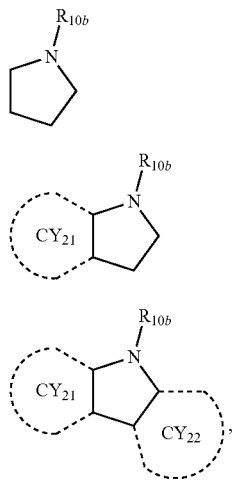

wherein, in Formulae 2-1 to 2-3, $CY_{21}$ and $CY_{22}$ may each independently be a $C_3$-$C_{20}$ carbocyclic group or a $C_1$-$C_{20}$ heterocyclic group, and $R_{10b}$ is the same as described in connection with $R_{10a}$.

In an embodiment, the second compound may be a carbazole-containing compound.

In an embodiment, the second compound may include groups represented by Formulae 2-1 to 2-3.

In an embodiment, $CY_1$ to $CY_4$, $Ar_1$, and $Ar_2$ in Formulae 1-1 and 1-2 may each independently be a π electron-rich $C_3$-$C_{60}$ cyclic group unsubstituted or substituted with at least one $R_{10a}$.

In an embodiment, the π electron-rich $C_3$-$C_{60}$ cyclic group may be a) a second ring or b) a condensed cyclic group in which two or more second rings are condensed with each other, and the second ring may be a benzene group, a cyclopentadiene group, a pyrrole group, a furan group, a thiophene group, or a silole group.

In an embodiment, $CY_1$ to $CY_4$, $Ar_1$, and $Ar_2$ in Formulae 1-1 and 1-2 may each independently be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphtho pyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonaphthothiophene group, an (indolo) phenanthrene group, a (benzofurano)phenanthrene group, or a (benzothieno)phenanthrene group, each unsubstituted or substituted with at least one $R_{10a}$.

In an embodiment, $CY_1$ to $CY_4$ in Formulae 1-1 and 1-2 may each independently be a benzene group or a naphthalene group, each unsubstituted or substituted with at least one $R_{10a}$.

In an embodiment, $Ar_1$ and $Ar_2$ in Formulae 1-1 and 1-2 may each independently be a benzene group, a naphthalene group, a fluorene group, a spiro-bifluorene group, a benzofluorene group, a dibenzofluorene group, a phenalene group, a phenanthrene group, an anthracene group, a pyrrole group, a furan group, a thiophene group, an isoindole group, an indole group, an indene group, a benzofuran group, a benzothiophene group, a benzosilole group, a naphtho pyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a benzonaphthofuran group, or a benzonaphthothiophene group, each unsubstituted or substituted with at least one $R_{10a}$.

In an embodiment, $L_1$ to $L_3$ in Formulae 1-1 and 1-2 may each independently be: a single bond; or a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{10a}$.

In an embodiment, $L_1$ to $L_3$ in Formulae 1-1 and 1-2 may each independently be: a single bond; or a benzene group, a fluorene group, or a carbazole group, each unsubstituted or substituted with at least one $R_{10a}$.

In an embodiment, $R_1$ to $R_4$, $Z_{1a}$, $Z_{1b}$, $Z_{2a}$, and $Z_{2b}$ in Formulae 1-1 and 1-2 may each independently be: hydrogen, deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, —$Si(Q_{31})(Q_{32})(Q_{33})$, —$B(Q_{31})(Q_{32})$, —$C(=O)(Q_{31})$, —$S(=O)_2(Q_{31})$, —$P(=O)(Q_{31})(Q_{32})$, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, —$P(=O)(Q_{31})(Q_{32})$, or any combination thereof; or —$Si(Q_1)(Q_2)(Q_3)$, —$B(Q_1)(Q_2)$, —$C(=O)(Q_1)$, —$S(=O)_2(Q_1)$, or —$P(=O)(Q_1)(Q_2)$. $Q_1$ to $Q_3$ and $Q_{31}$ to $Q_{33}$ are each the same as described in the present specification.

In an embodiment, $R_1$ to $R_4$, $Z_{1a}$, $Z_{1b}$, $Z_{2a}$, and $Z_{2b}$ in Formulae 1-1 and 1-2 may each independently be:

hydrogen, deuterium, —F, —Cl, —Br, —I, a hydroxyl group, a cyano group, or a nitro group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a cyclopentyl group, a cyclohexyl group, a cyclopentenyl group, a cyclohexenyl group, a phenyl group, a naphthyl group, —$Si(Q_{31})(Q_{32})(Q_{33})$, —$B(Q_{31})(Q_{32})$, —$C(=O)(Q_{31})$, —$S(=O)_2(Q_{31})$, —$P(=O)(Q_{31})(Q_{32})$, or any combination thereof;

a cyclopentyl group, a cyclohexyl group, a cyclopentenyl group, a cyclohexenyl group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a carbazolyl group, a benzofuranyl group, a dibenzofuranyl group, a dibenzothiophenyl group, a benzocarbazolyl group, or a dibenzocarbazolyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, a cyclopentenyl group, a cyclohexenyl group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, —$Si(Q_{31})(Q_{32})(Q_{33})$, —$B(Q_{31})(Q_{32})$, —$C(=O)(Q_{31})$, —$S(=O)_2(Q_{31})$, —$P(=O)(Q_{31})(Q_{32})$, or any combination thereof; or —$Si(Q_1)(Q_2)(Q_3)$, —$B(Q_1)(Q_2)$, —$C(=O)(Q_1)$, —$S(=O)_2(Q_1)$, or —$P(=O)(Q_1)(Q_2)$. $Q_1$ to $Q_3$ and $Q_{31}$ to $Q_{33}$ are each the same as described in the present specification.

In an embodiment, the first to third compounds may each independently be selected from Compounds 1 to 57, but embodiments are not limited thereto:

1
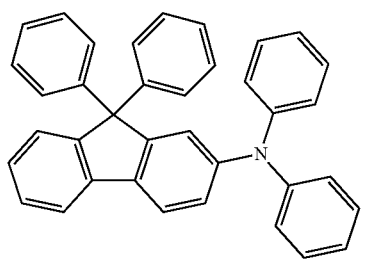
2
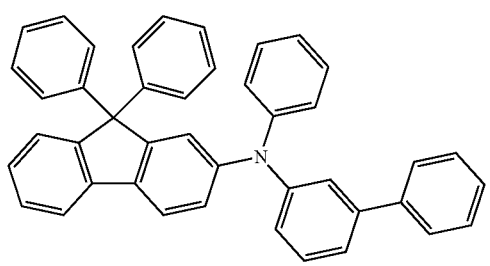
3
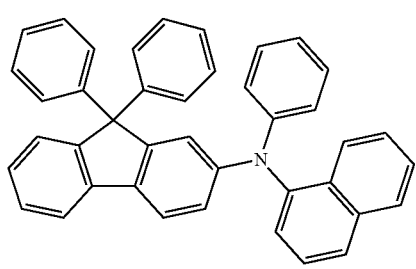
4
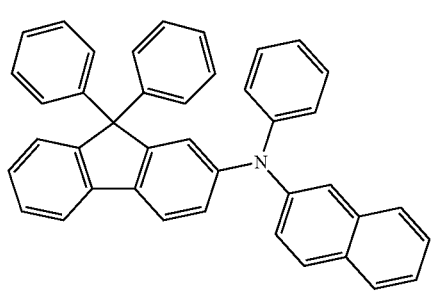
5
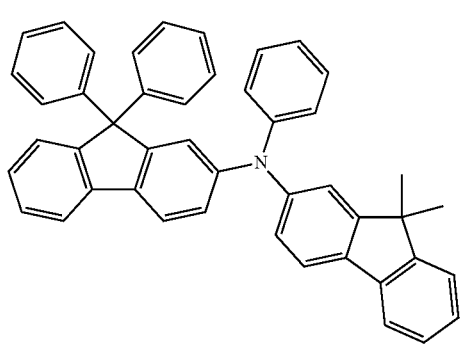
6
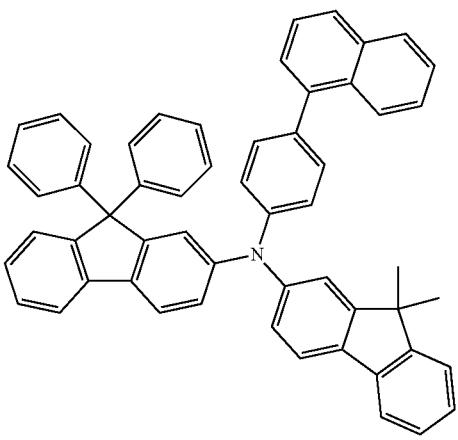
7
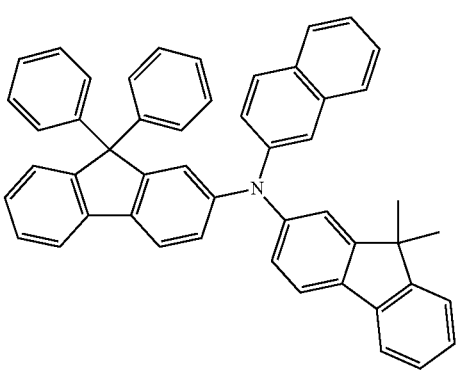
8
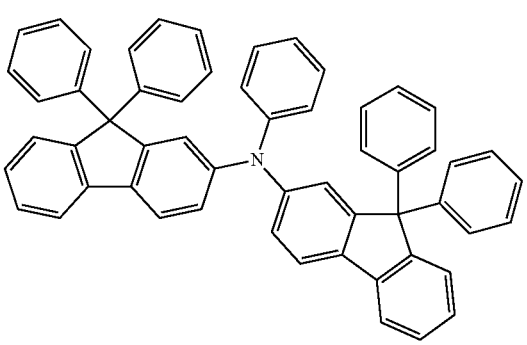
9
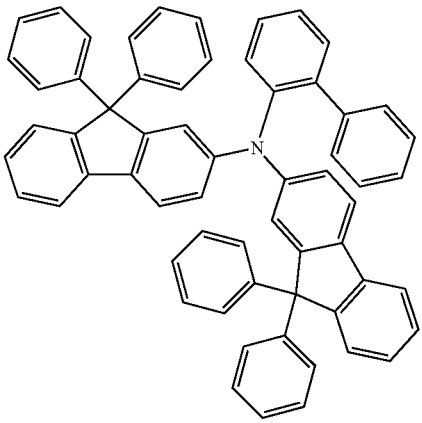

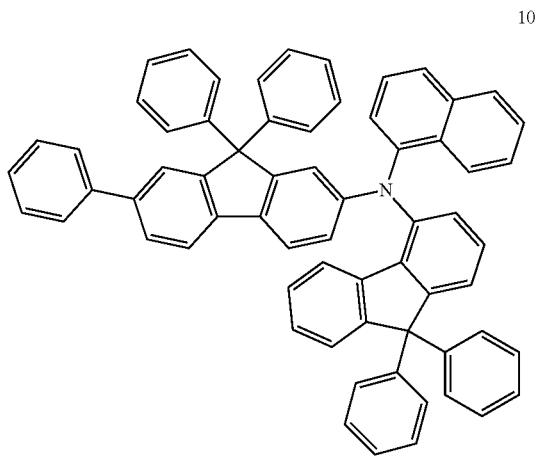
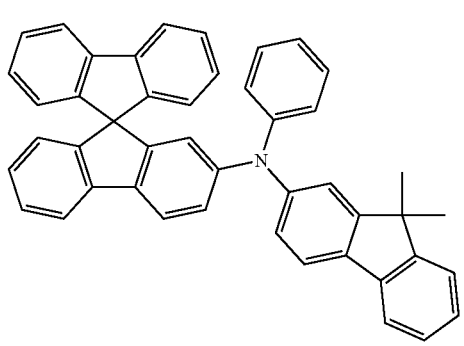
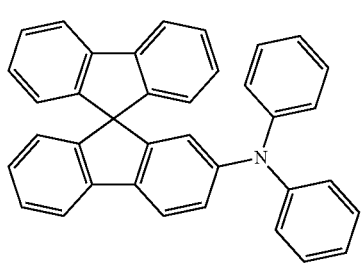
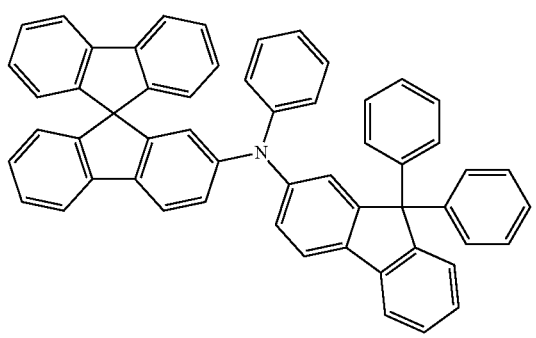
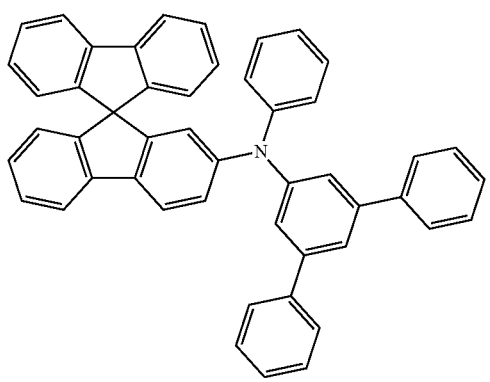
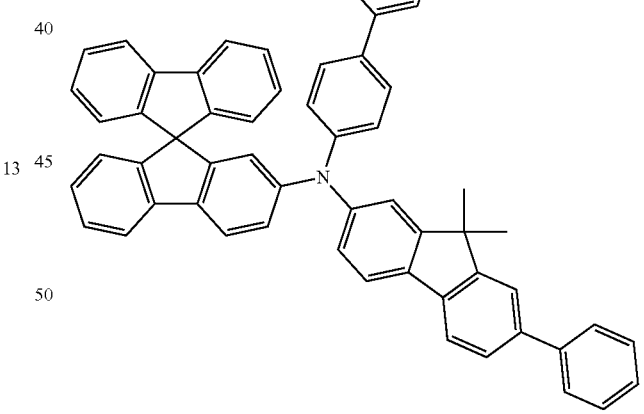
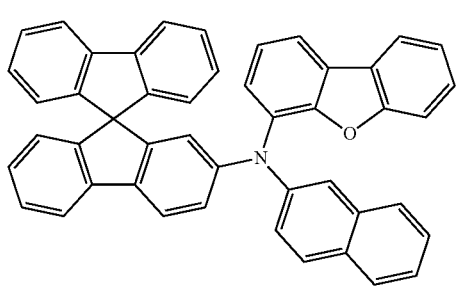
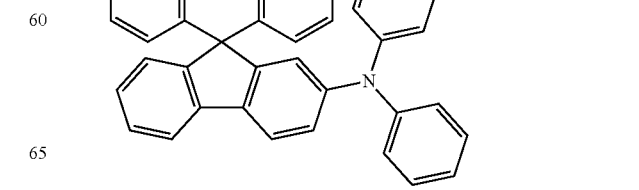

19
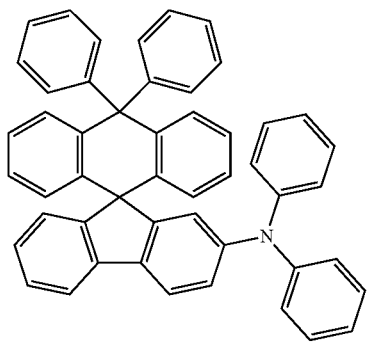
20
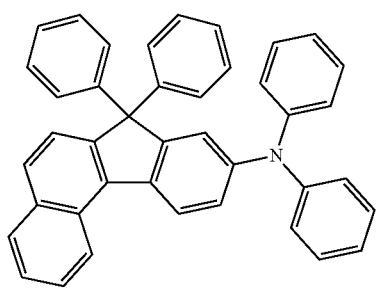
21
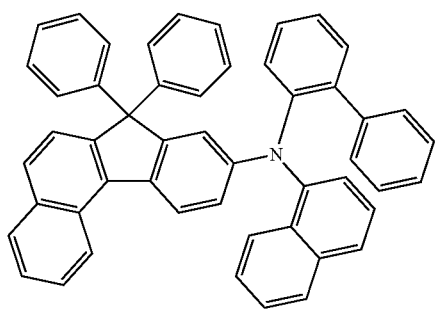
22
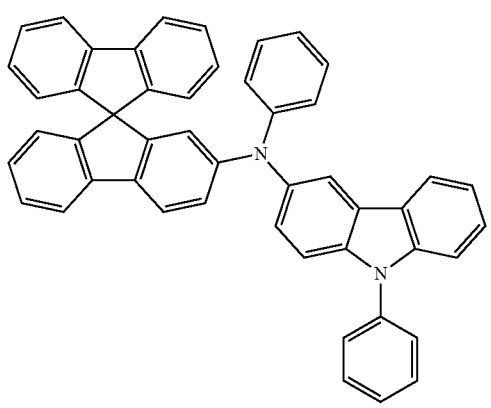
23
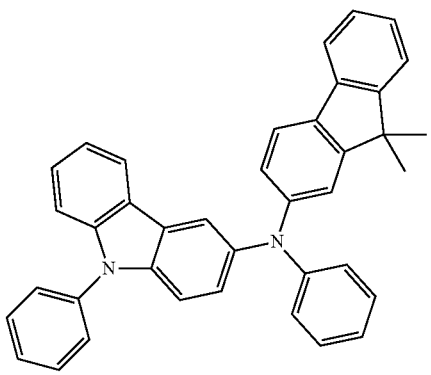
24
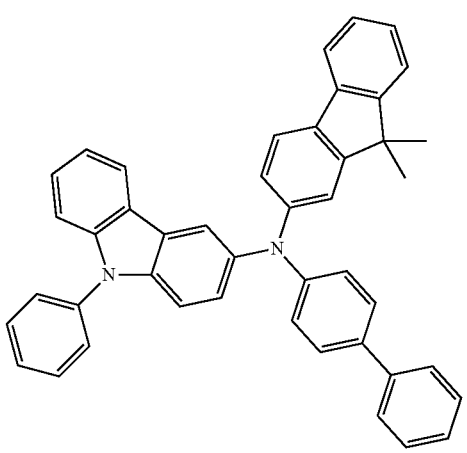
25
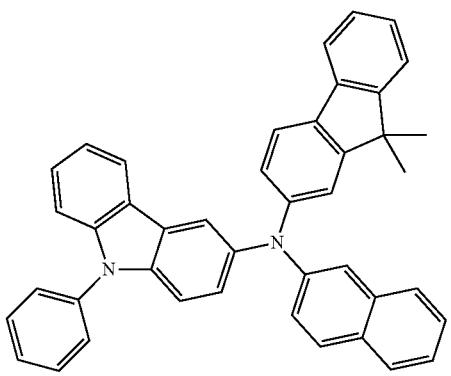
26
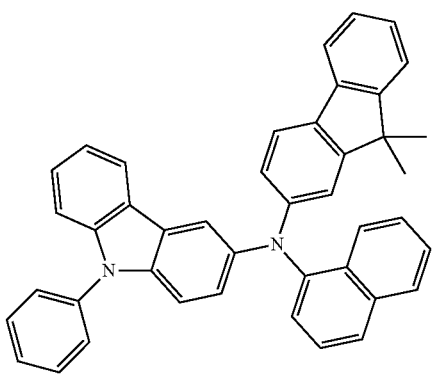

27
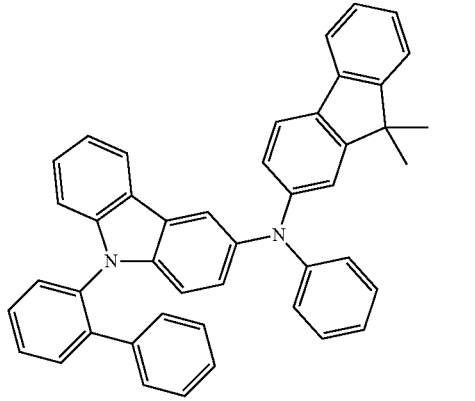
28
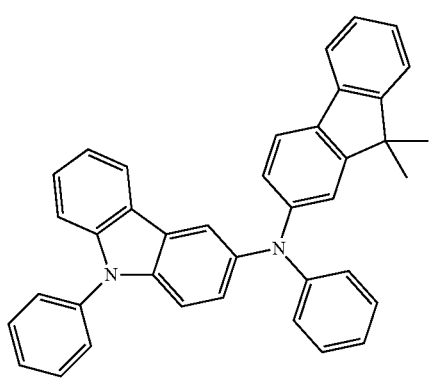
29
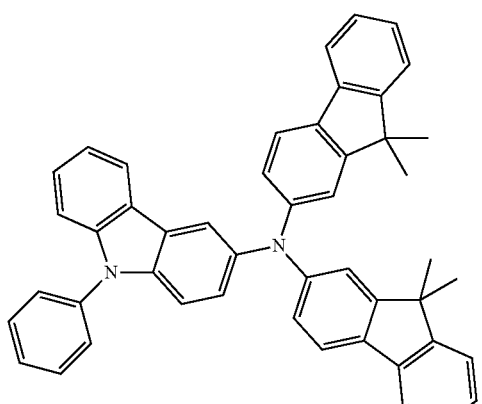
30
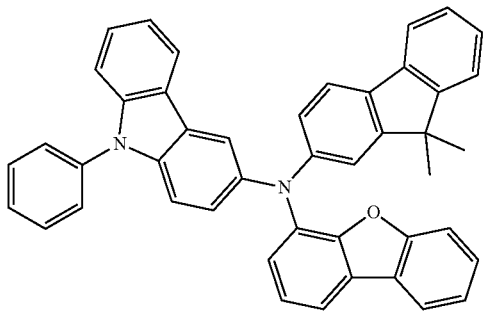
31
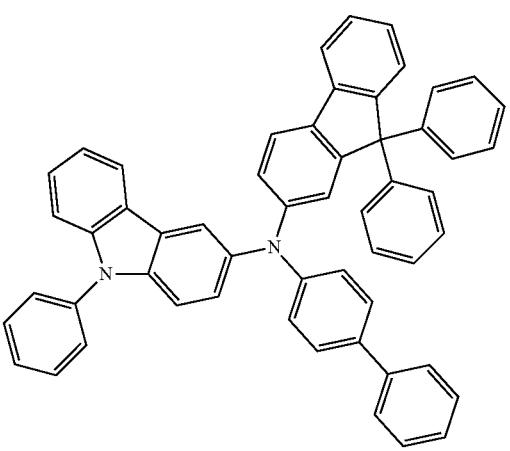
32
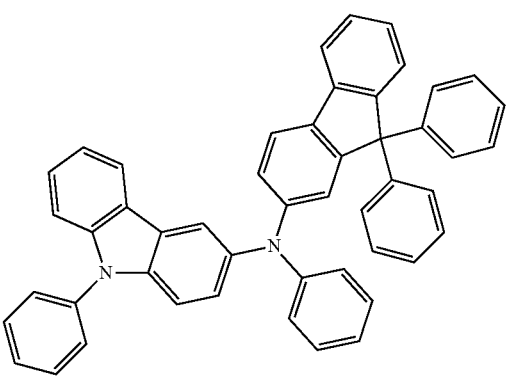
33
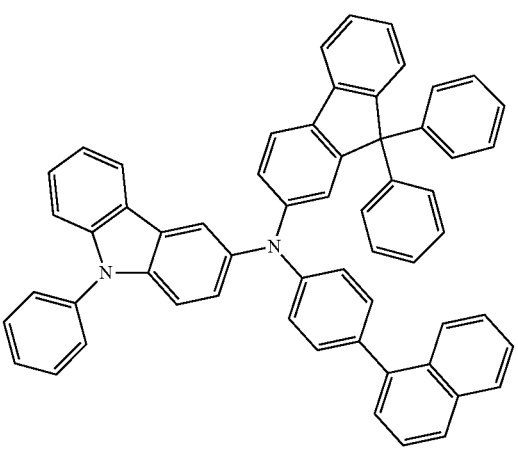

34
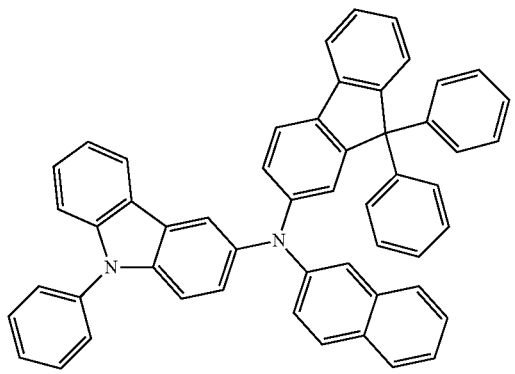
35
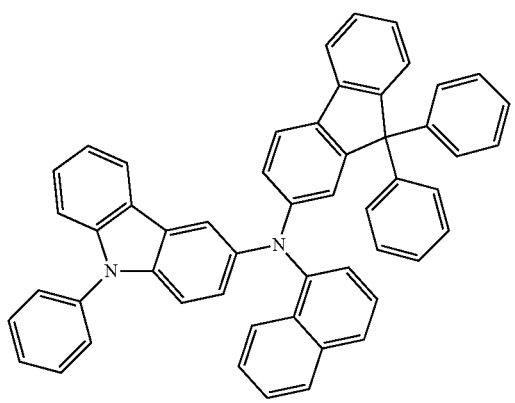
36
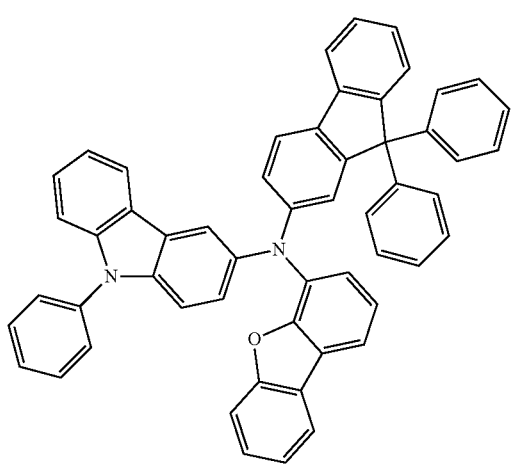
37
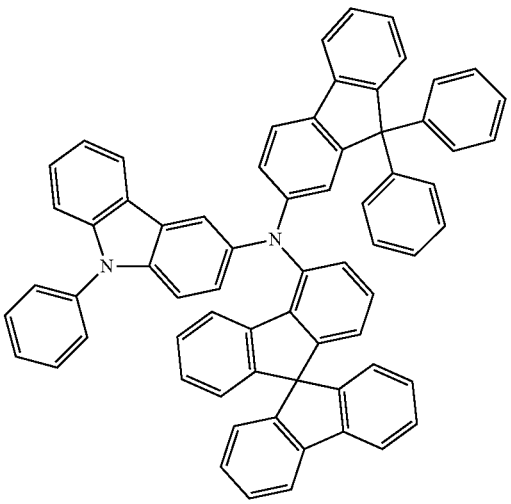
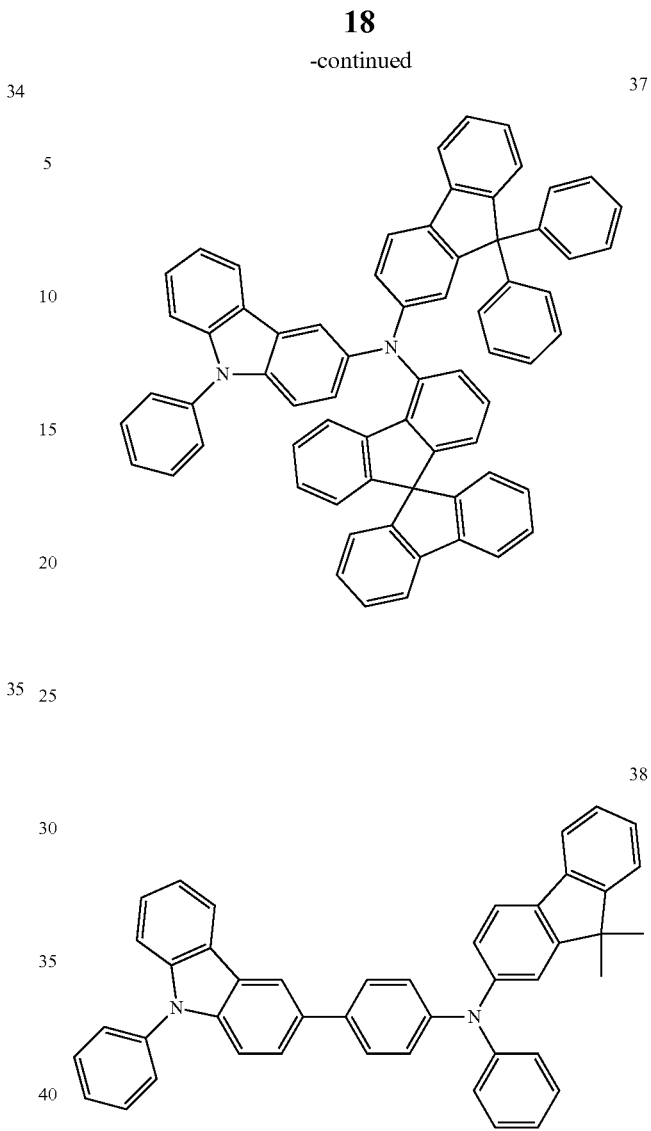
38
39
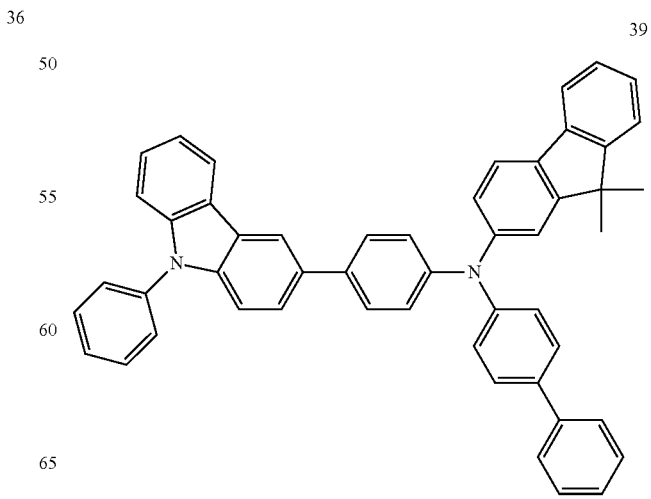

40
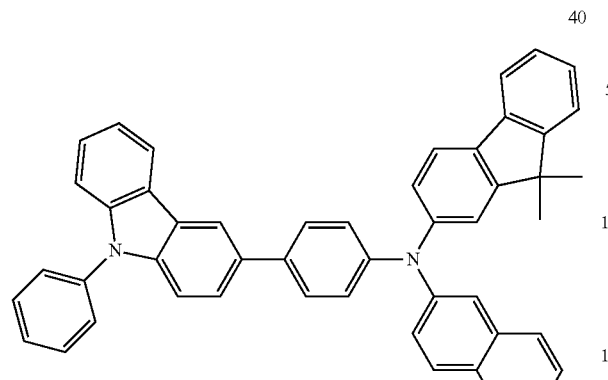
41
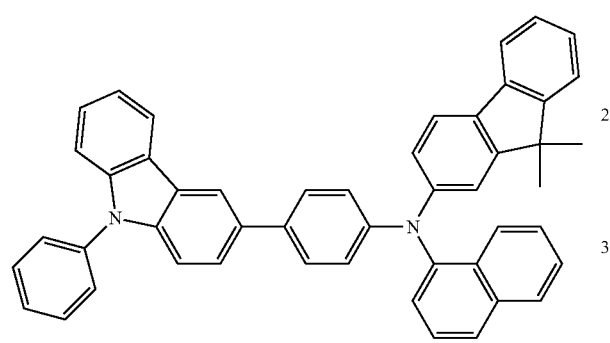
42
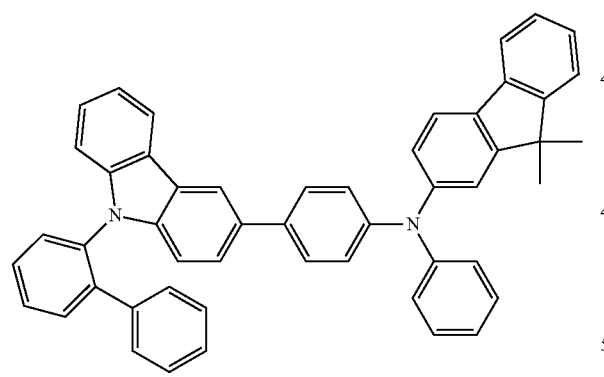
43
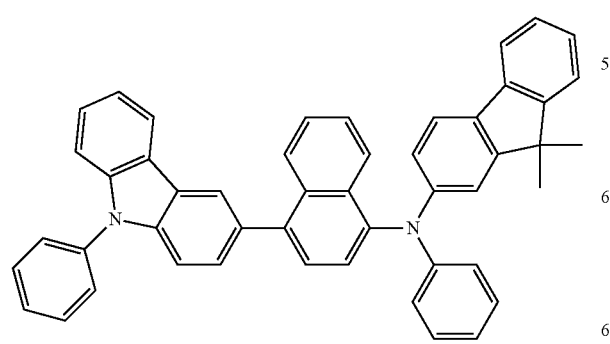
44
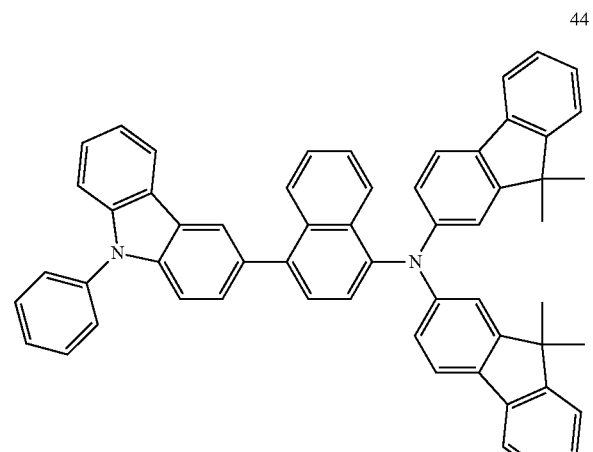
45
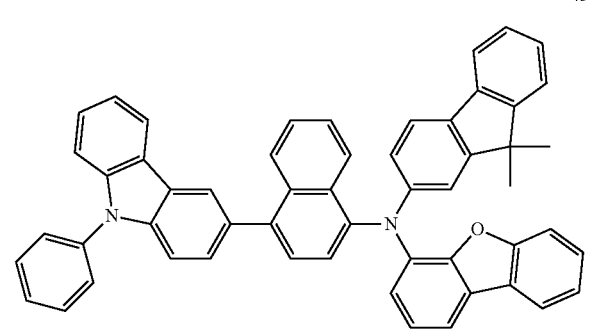
46
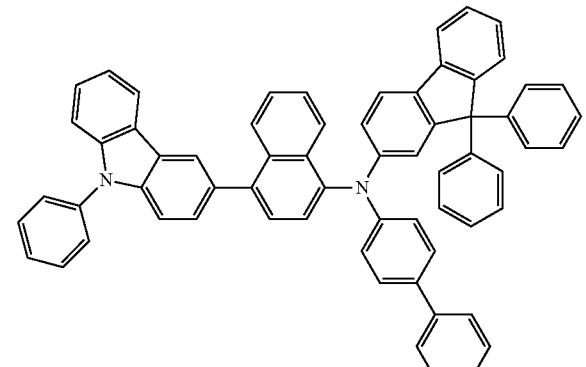
47
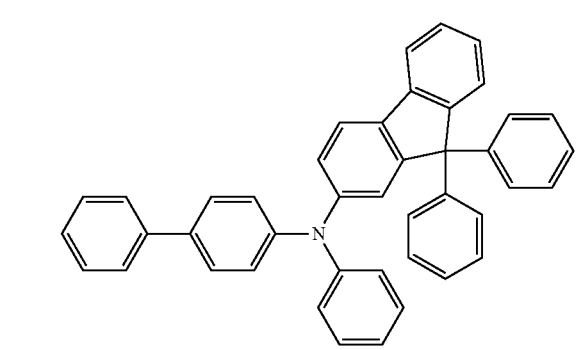

48
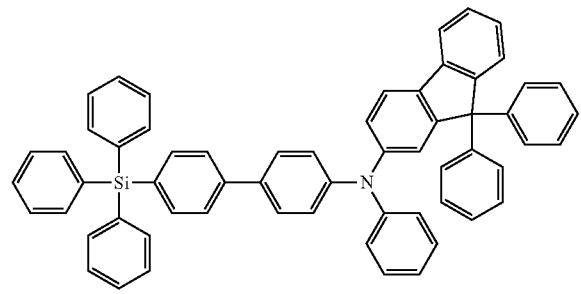
49
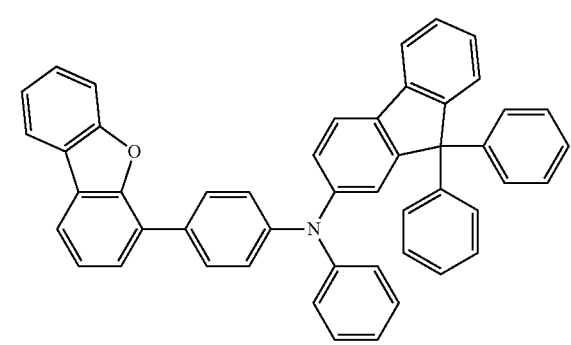
50
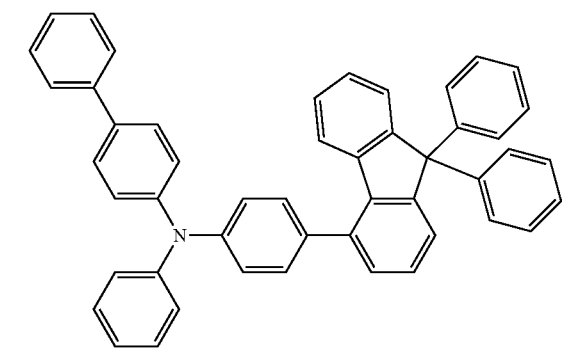
51
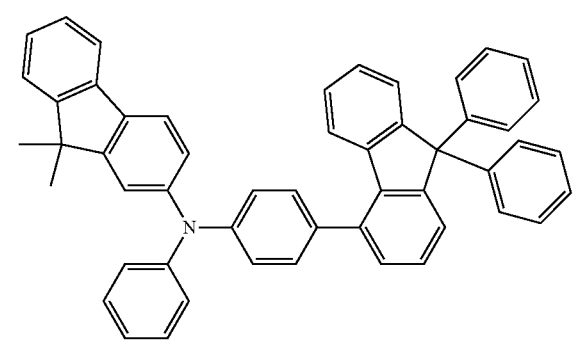
52
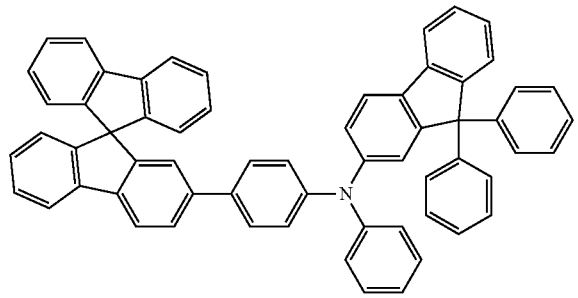
53
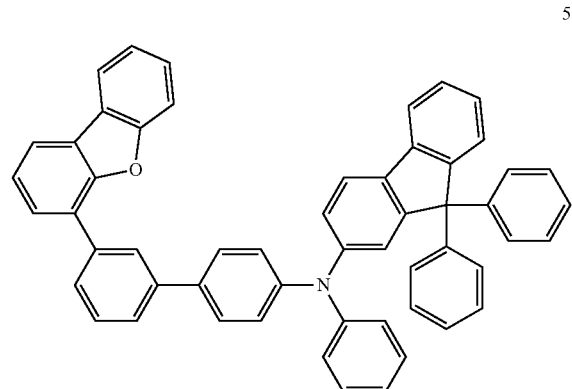
54
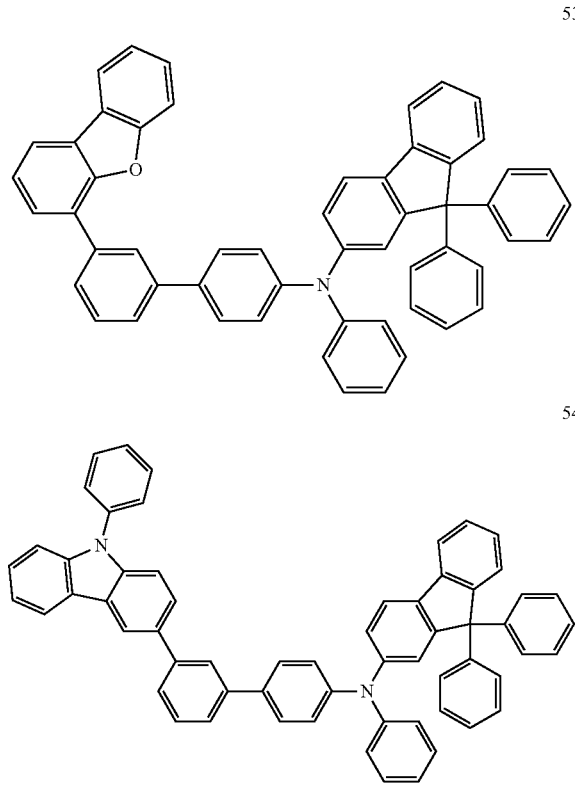
55
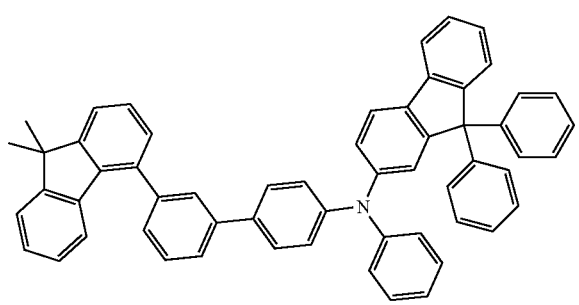
56
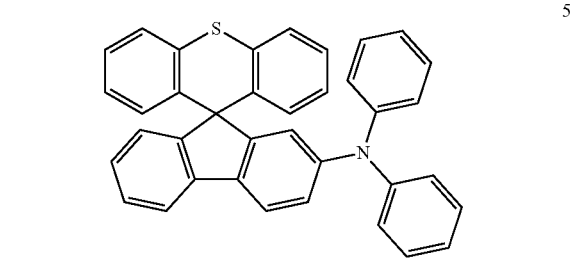

-continued

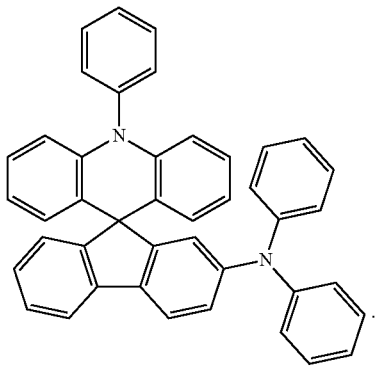

In an embodiment, the first compound may be selected from Compounds 1 to 21, 56, and 57, but embodiments are not limited thereto.

In an embodiment, the second compound may be selected from Compounds 22 to 46 and 54, but embodiments are not limited thereto.

In an embodiment, the third compound may be selected from Compounds 47 to 55, but embodiments are not limited thereto.

Synthesis methods of the first to third compounds may be recognizable by one of ordinary skill in the art by referring to Examples provided below.

In an embodiment, the first electrode of the light-emitting device may be an anode,
the second electrode of the light-emitting device may be a cathode,
the interlayer may further include an electron transport region between the emission layer and the second electrode,
the hole transport region may further include a hole injection layer, an emission auxiliary layer, an electron blocking layer, or any combination thereof, and
the electron transport region may include a buffer layer, a hole blocking layer, an electron control layer, an electron transport layer, an electron injection layer, or any combination thereof.

In an embodiment, the hole transport region of the light-emitting device may further include a p-dopant.

In an embodiment, in the light-emitting device, i) the first hole transport layer may be in direct contact with the second hole transport layer,
ii) the second hole transport layer may be in direct contact with the third hole transport layer, or
iii) the first hole transport layer may be in direct contact with the second hole transport layer, and the second hole transport layer may be in direct contact with the third hole transport layer.

In an embodiment, in the light-emitting device, the third hole transport layer may be in direct contact with the emission layer.

In an embodiment, thicknesses of the first hole transport layer and the third hole transport layer may each independently be from about 5 nm to about 80 nm.

In an embodiment, thicknesses of the first hole transport layer and the third hole transport layer may each independently be from about 5 nm to about 30 nm.

In an embodiment, thicknesses of the first hole transport layer and the third hole transport layer may each independently be from about 30 nm to about 50 nm.

In an embodiment, thicknesses of the first hole transport layer and the third hole transport layer may each independently be from about 50 nm to about 80 nm.

In an embodiment, thicknesses of the first hole transport layer and the third hole transport layer may each independently be from about 5 nm to about 65 nm.

In an embodiment, a thickness of the second hole transport layer may be greater than or equal to the thickness of the first hole transport layer or the third hole transport layer.

In an embodiment, a thickness of the second hole transport layer may be greater than the thickness of the first hole transport layer or the third hole transport layer.

In an embodiment, $T_1(HTM3)$ may be about 1.7 eV or more and about 2.8 eV or less.

In an embodiment, a difference between $T_1(HTM3)$ and $T_1(D)$ may be about 0.3 eV or more and about 0.8 eV or less.

In an embodiment, a difference between $T_1(HTM3)$ and $T_1(D)$ may be about 0.3 eV or more and about 0.6 eV or less.

In an embodiment, the first electrode of the light-emitting device may be patterned according to a first subpixel, a second subpixel, and a third subpixel,
the emission layer may include a first emission layer that is formed in the first subpixel and emits first-color light, a second emission layer that is formed in the second subpixel and emits second-color light, and a third emission layer that is formed in the third subpixel and emits third-color light,
the first hole transport layer and the second hole transport layer may be common layers formed over all of the first subpixel, the second subpixel, and the third subpixel,
the third hole transport layer may include a hole transport layer 3-1 formed in the first subpixel, a hole transport layer 3-2 formed in the second subpixel, and a hole transport layer 3-3 formed in the third subpixel,
the first emission layer may include a first dopant,
the second emission layer may include a second dopant,
the third emission layer may include a third dopant,
the hole transport layer 3-1 may include a third compound (e.g., a first third compound),
the hole transport layer 3-2 may include a third compound (e.g., a second third compound),
the hole transport layer 3-3 may include a third compound (e.g., a third compound),
the third compound included in the hole transport layer 3-1, the third compound included in the hole transport layer 3-2, and the third compound included in the hole transport layer 3-3 may be identical to or different from each other, and
Equation 2 may be satisfied:

$$T_1(HTM3\text{-}1) > T_1(D1);$$

$$T_1(HTM3\text{-}2) > T_1(D2); \text{ and}$$

$$T_1(HTM3\text{-}3) > T_1(D3), \quad \text{Equation 2}$$

wherein, in Equation 2,
$T_1(HTM3\text{-}1)$ is a triplet energy level in electron volt (eV) of the first third compound included in the hole transport layer 3-1,
$T_1(HTM3\text{-}2)$ is a triplet energy level in electron volt (eV) of the second third compound included in the hole transport layer 3-2,
$T_1(HTM3\text{-}3)$ is a triplet energy level in electron volt (eV) of the third compound included in the hole transport layer 3-3,
$T_1(D1)$ is a triplet energy level in electron volt (eV) of the first dopant, $T_1(D2)$ is a triplet energy level in electron volt (eV) of the second dopant, $T_1(D3)$ is a triplet energy level in electron volt (eV) of the third dopant, and $T_1(HTM3-1)$ to $T_1(HTM3-3)$ and $T_1(D1)$ to $T_1(D3)$ are values evaluated utilizing the DFT method of the Gaussian program, which is structure-optimized at the B3LYP/6-31G(d,p) level.

In an embodiment, the light-emitting device may further satisfy Equation 2-1:

$$T_1(HTM3\text{-}1) \geq T_1(D1)+0.3 \text{ eV};$$

$$T_1(HTM3\text{-}2) \geq T_1(D2)+0.3 \text{ eV; and}$$

$$T_1(HTM3\text{-}3) \geq T_1(D3)+0.3 \text{ eV.} \qquad \text{Equation 2-1}$$

In an embodiment, at least two of the first-color light to the third-color light of the light-emitting device may be different from each other. That is, at least two selected from the first-color light to the third-color light of the light-emitting device may have different color from each other.

In an embodiment, the emission layer of the light-emitting device may emit red light, green light, blue light, and/or white light. In an embodiment, the emission layer may emit blue light. The blue light may have a maximum emission wavelength of, for example, about 400 nm to about 490 nm. The emission layer is the same as described in the present specification.

In the light-emitting device, the first hole transport layer includes the first compound, the second hole transport layer includes the second compound, the third hole transport layer includes the third compound, and the first to third compounds are each independently an amine-based compound, but are different from each other. Thus, rapid hole injection and transport are possible, and accordingly, thin film stability and layer-to-layer charge transfer performance may be improved.

In addition, because the light-emitting device satisfies Equation 1 in the present specification, electrons and holes may effectively generate excitons in the emission layer, and prevent or reduce diffusion of excitons such that excitons are effectively limited to the emission layer, and thus luminescence efficiency may be improved. Accordingly, charge balance in the light-emitting device is adjusted (e.g., the light-emitting device has a suitable charge balance), and thus the light-emitting device may have low driving voltage, high efficiency, and long lifespan.

In an embodiment, the light-emitting device may include a capping layer located outside the first electrode or located outside the second electrode.

In an embodiment, the light-emitting device may further include a first capping layer located outside the first electrode and/or a second capping layer located outside the second electrode, and the first capping layer and/or the second capping layer may include a heterocyclic compound represented by Formula 1. The first capping layer and/or the second capping layer are each the same as described in the present specification.

In an embodiment, the light-emitting device may include:
a first capping layer located outside the first electrode (e.g., facing away from the second electrode) and including at least one of the first to third compounds; or
a second capping layer located outside the second electrode (e.g., facing away from the first electrode) and including at least one of the first to third compounds; or
the first capping layer and the second capping layer. That is, the light-emitting device may include both the first capping layer located outside the first electrode and the second capping layer located outside the second electrode.

The wording "(interlayer and/or capping layer) includes a first compound" as used herein may be understood as "(interlayer and/or capping layer) may include one kind of the amine-based compound or two or more different kinds of amine-based compounds belonging to the category of the amine-based compound."

In an embodiment, the interlayer and/or the capping layer may include only Compound 1 as the amine-based compound. For example, Compound 1 may be present in the hole transport region of the light-emitting device. In an embodiment, the interlayer may include Compound 1, Compound 2, and Compound 3, as the first to third compounds. For example, Compound 1 and Compound 2 may be present in an identical layer (for example, Compound 1 and Compound 2 may both be present in the hole transport region), or different layers (for example, Compound 1 may be present in the hole transport region and Compound 2 may be present in the electron transport region).

The term "interlayer" as used herein refers to a single layer or a plurality of layers located between the first electrode and the second electrode of the light-emitting device.

According to another embodiment of the present disclosure, an electronic apparatus includes the light-emitting device as described above. The electronic apparatus may further include a thin-film transistor. In an embodiment, the electronic apparatus may further include a thin-film transistor including a source electrode and a drain electrode, and the first electrode of the light-emitting device may be electrically connected to the source electrode or the drain electrode. In an embodiment, the electronic apparatus may further include a color filter, a color conversion layer, a touch screen layer, a polarizing layer, or any combination thereof. More details on the electronic apparatus are the same as described in the present specification.

Description of FIG. 1

FIG. 1 is a schematic cross-sectional view of a light-emitting device 10 according to an embodiment of the disclosure. The light-emitting device 10 includes a first electrode 110, a hole transport region 120, a first hole transport layer 121, a second hole transport layer 122, a third hole transport layer 123, an emission layer 131, an interlayer 130, and a second electrode 150. That is, the light-emitting device 10 includes a first electrode 110, an interlayer 130, and a second electrode 150. The interlayer 130 includes a hole transport region 120 (including a first hole transport layer 121, a second hole transport layer 122, and a third hole transport layer 123), and an emission layer 131.

Hereinafter, a structure of the light-emitting device 10 according to an embodiment and a method of manufacturing the light-emitting device 10 will be described in connection with FIG. 1.

First Electrode 110

In FIG. 1, a substrate may be additionally located under the first electrode 110 or above the second electrode 150. As the substrate, a glass substrate or a plastic substrate may be utilized. In an embodiment, the substrate may be a flexible substrate, and may include plastics with suitable (e.g., excellent) heat resistance and durability, such as polyimide, polyethylene terephthalate (PET), polycarbonate, polyethylene naphthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that can facilitate injection of holes.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide (SnO$_2$), zinc oxide (ZnO), or any combinations thereof. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be utilized as the material for forming the first electrode 110.

The first electrode 110 may have a single-layered structure consisting of a single layer or a multi-layered structure including a plurality of layers. For example, the first electrode 110 may have a three-layered structure of ITO/Ag/ITO.

Interlayer 130

The interlayer 130 may be located on the first electrode 110. The interlayer 130 may include an emission layer.

The interlayer 130 may further include a hole transport region between the first electrode 110 and the emission layer and an electron transport region between the emission layer and the second electrode 150.

The interlayer 130 may further include a metal-containing compound such as an organometallic compound, an inorganic material such as quantum dots, and/or the like, in addition to various suitable organic materials.

In an embodiment, the interlayer 130 may include i) two or more emitting units sequentially stacked between the first electrode 110 and the second electrode 150 and ii) a charge generation layer between two adjacent emitting units. When the interlayer 130 includes the emitting unit and the charge generation layer as described above, the light-emitting device 10 may be a tandem light-emitting device.

Hole Transport Region 120 in Interlayer 130

The hole transport region 120 may have: i) a single-layered structure consisting of a single layer consisting of a single material, ii) a single-layered structure consisting of a single layer consisting of a plurality of different materials, or iii) a multi-layered structure including a plurality of layers including different materials.

In an embodiment, the hole transport region 120 may include the first hole transport layer 121, the second hole transport layer 122 between the first hole transport layer 121 and the emission layer, and the third hole transport layer 123 between the second hole transport layer 122 and the emission layer.

The hole transport region 120 may include a hole injection layer, a hole transport layer, an emission auxiliary layer, an electron blocking layer, or any combination thereof.

In an embodiment, the hole transport region 120 may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, constituting layers are stacked sequentially from the first electrode 110 in the respective stated order.

The hole transport region 120 may include the first to third compounds according to the present specification.

In an embodiment, the first hole transport layer 121 may include the first compound, the second hole transport layer 122 may include the second compound, the third hole transport layer 123 may include the third compound, and the first compound to the third compound may each independently be an amine-based compound, but may be different from each other.

The hole transport region 120 may further include a compound represented by Formula 201, a compound represented by Formula 202, or any combination thereof:

Formula 201

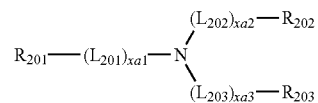

Formula 202

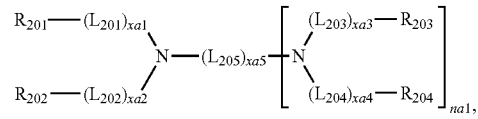

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N(Q$_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and 0201 may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group and/or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$ or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one of the groups represented by Formulae CY201 to CY217.

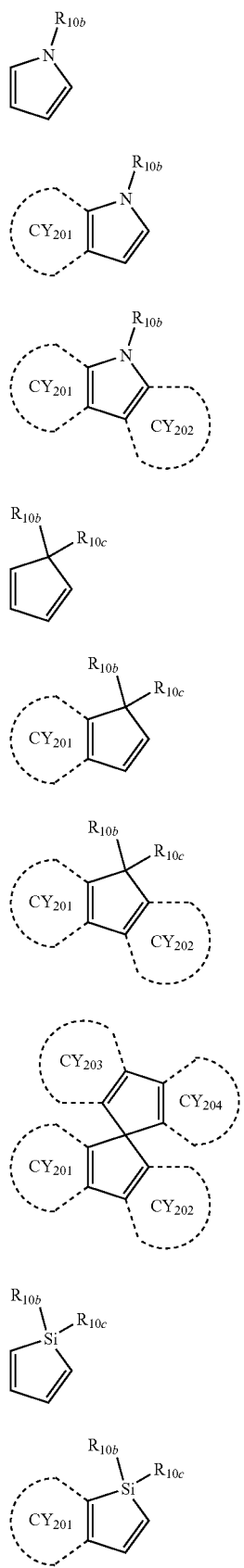
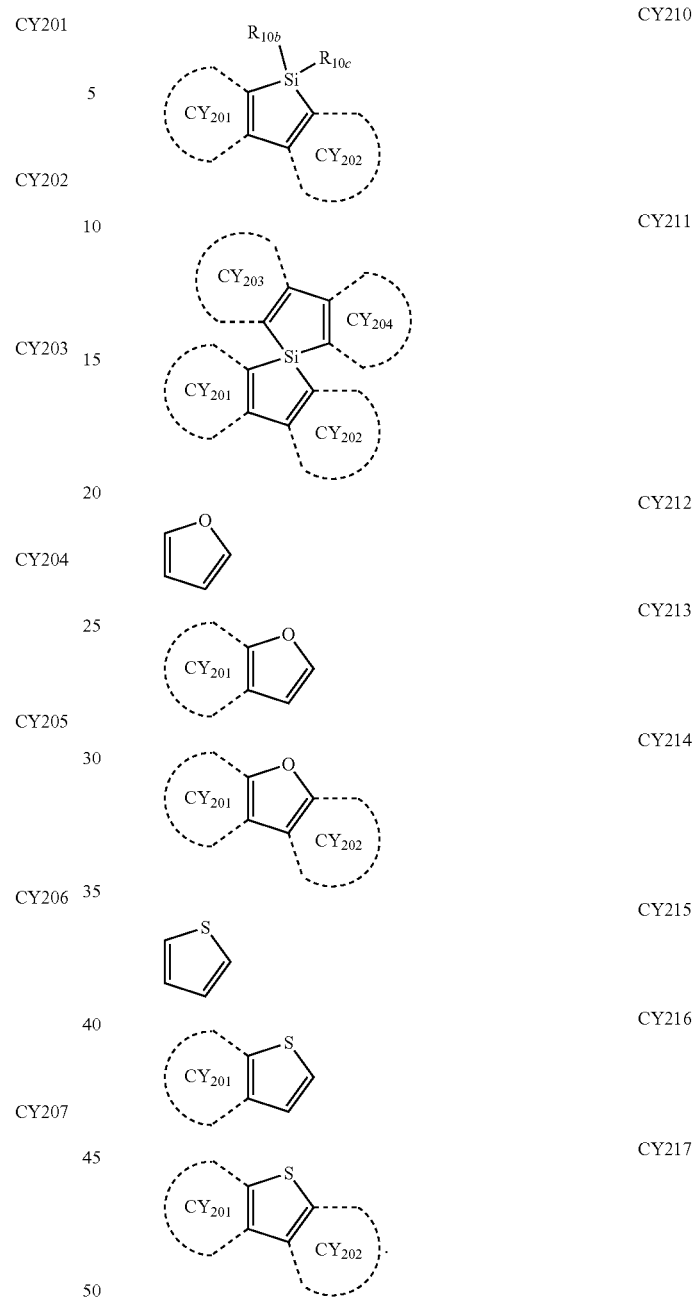

In Formulae CY201 to CY217, $R_{10b}$ and $R_{10c}$ are each the same as described in connection with $R_{10a}$ in the present specification, $CY_{201}$ to $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$ as described in the present specification.

In an embodiment, $CY_{201}$ to $CY_{204}$ in Formulae CY201 to CY217 may each independently be a benzene group, a naphthalene group, a phenanthrene group, or an anthracene group.

In an embodiment, each of Formulae 201 and 202 may include at least one of the groups represented by Formulae CY201 to CY203.

In an embodiment, Formula 201 may include at least one of the groups represented by Formulae CY201 to CY203 and at least one of the groups represented by Formulae CY204 to CY217.

In an embodiment, xa1 in Formula 201 may be 1, $R_{201}$ may be a group represented by one of Formulae CY201 to CY203, xa2 may be 0, and $R_{202}$ may be a group represented by one of Formulae CY204 to CY207.

In an embodiment, each of Formulae 201 and 202 may not include the groups represented by Formulae CY201 to CY203.

In an embodiment, each of Formulae 201 and 202 may not include groups represented by Formulae CY201 to CY203, and may include at least one of the groups represented by Formulae CY204 to CY217.

In an embodiment, each of Formulae 201 and 202 may not include the groups represented by Formulae CY201 to CY217.

In an embodiment, the hole transport region 120 may include one of Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris (N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

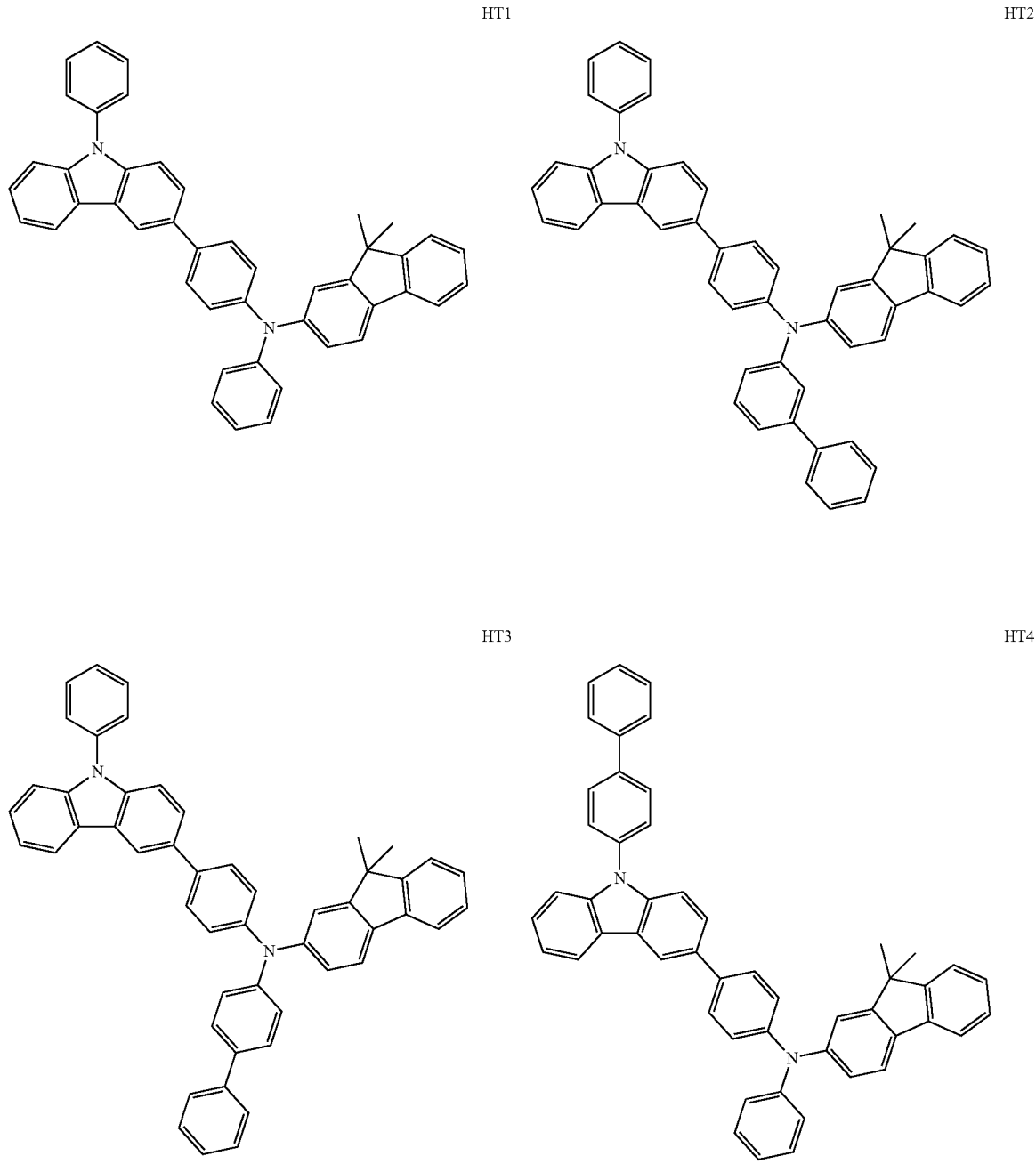

HT5
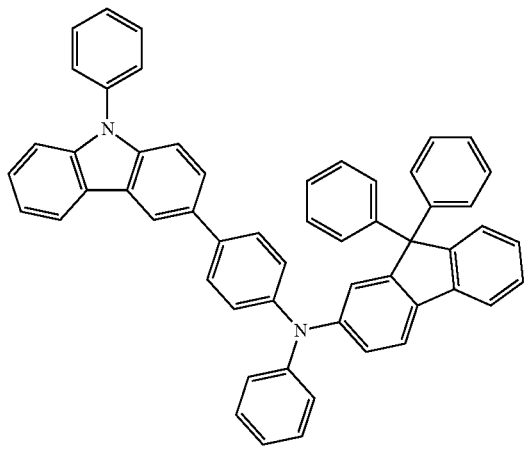
HT6
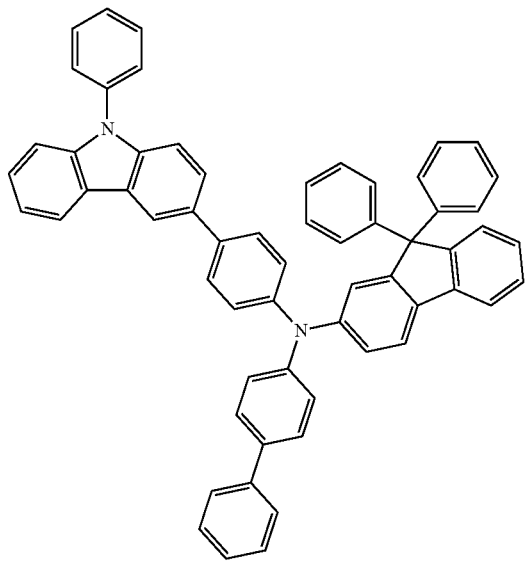
HT7
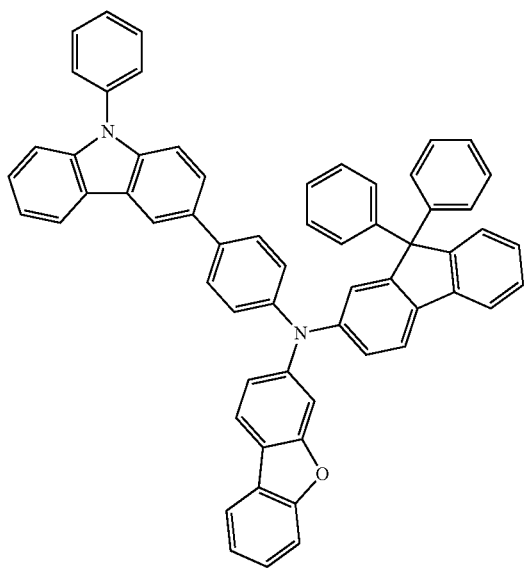
HT8
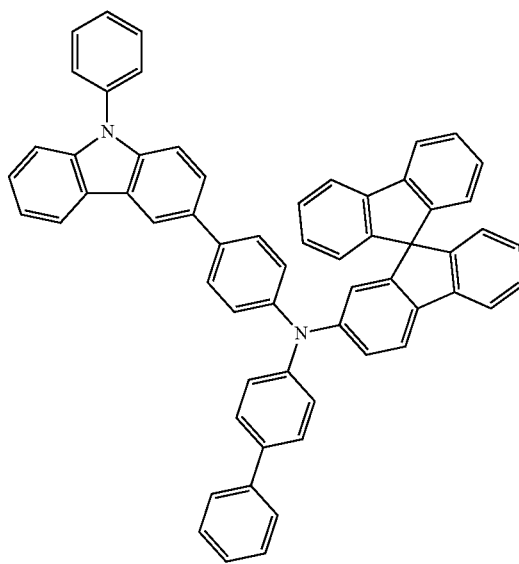

HT9
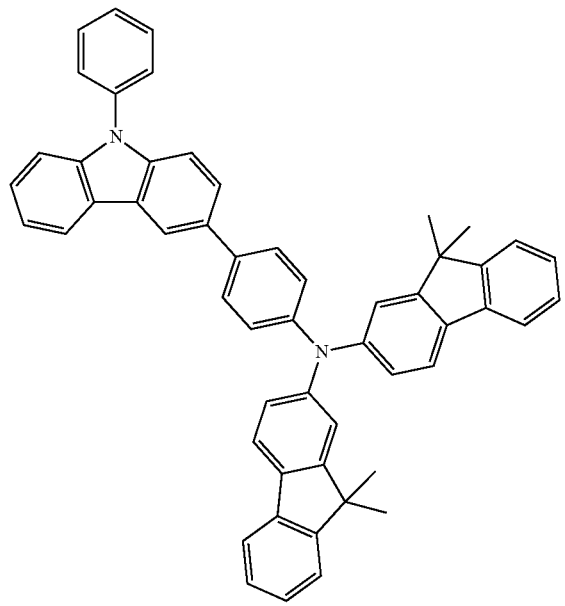
HT10
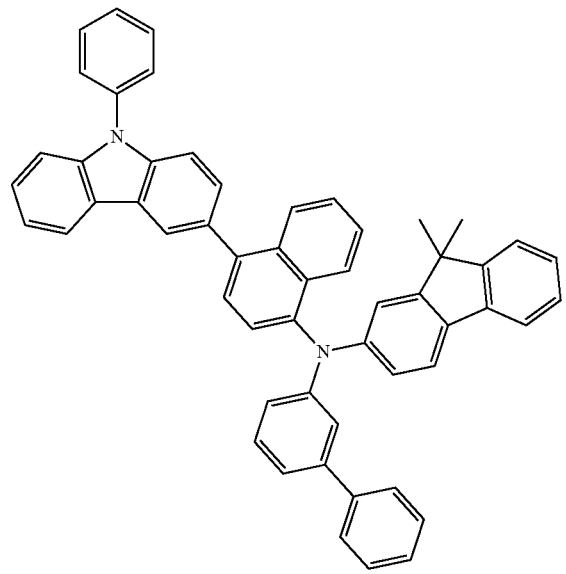
HT11
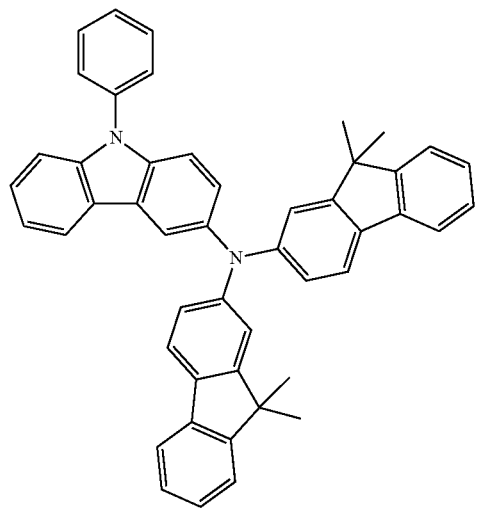
H12
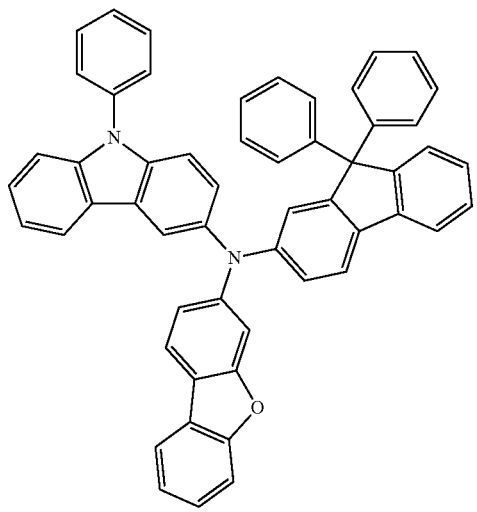

-continued
HT13
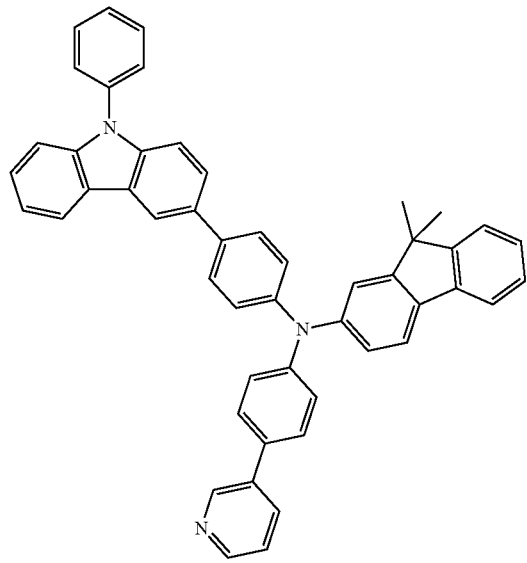
HT14
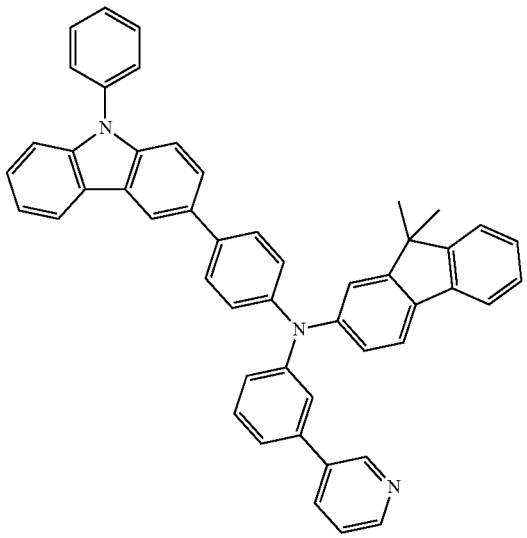
HT15
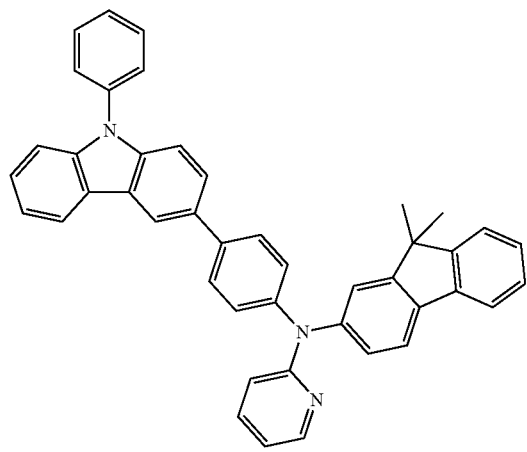
HT16
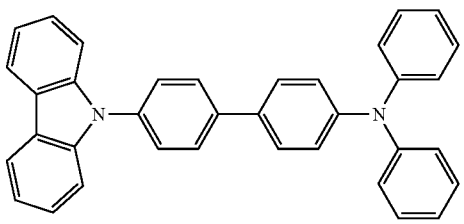
HT17
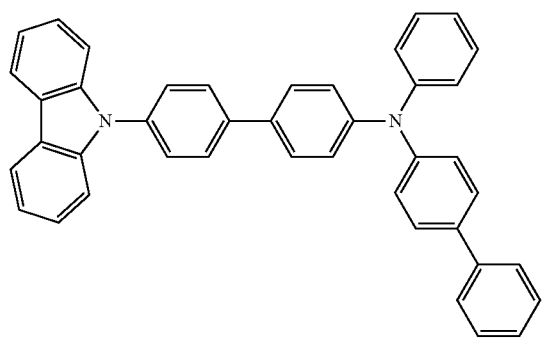
HT18
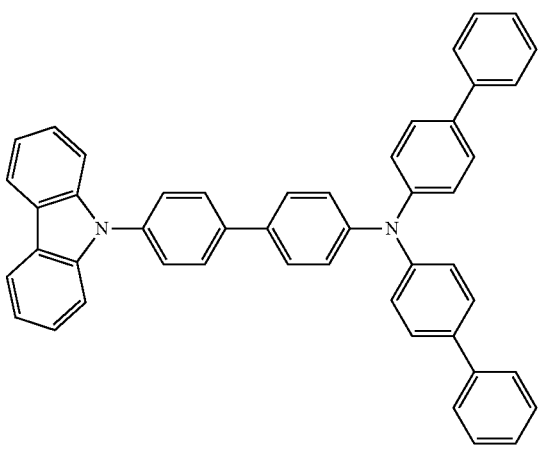

-continued
HT19
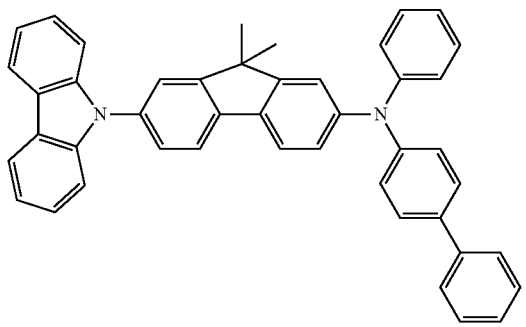
HT20
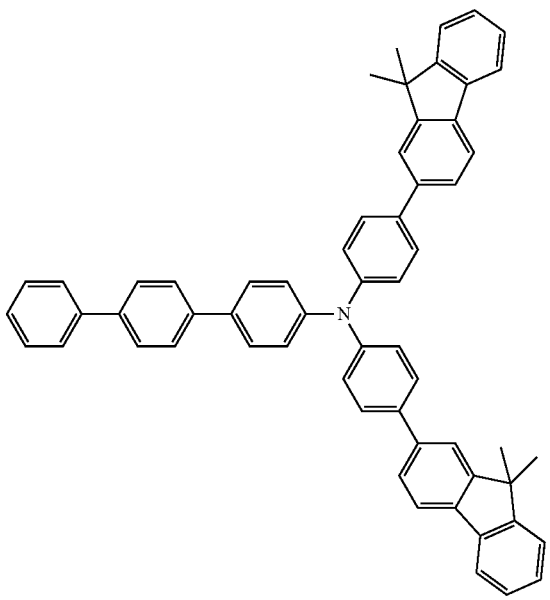
HT21
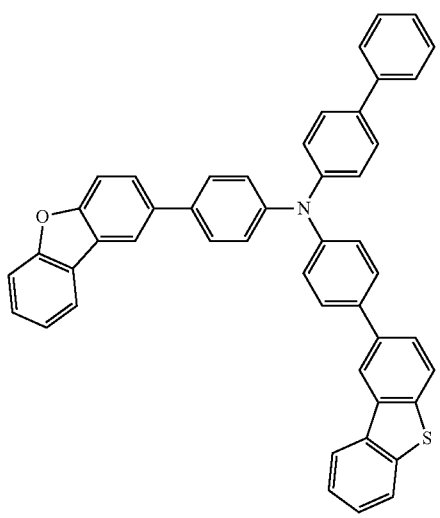
HT22
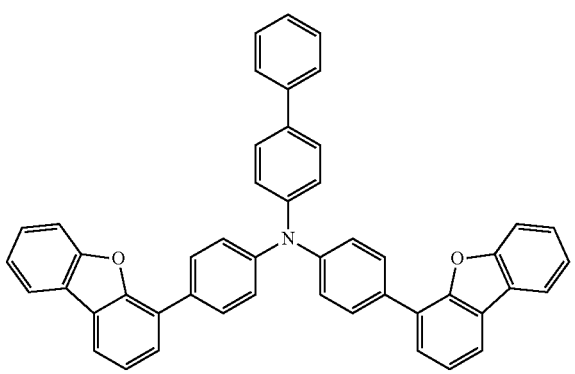
HT23
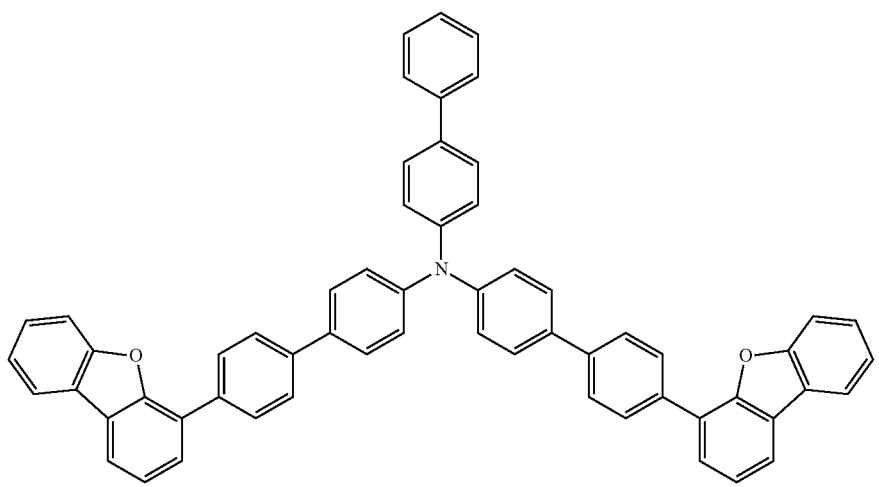

-continued
HT24
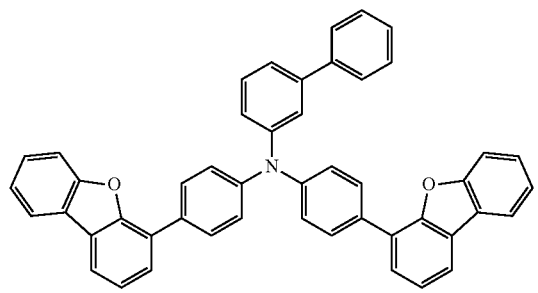
HT25
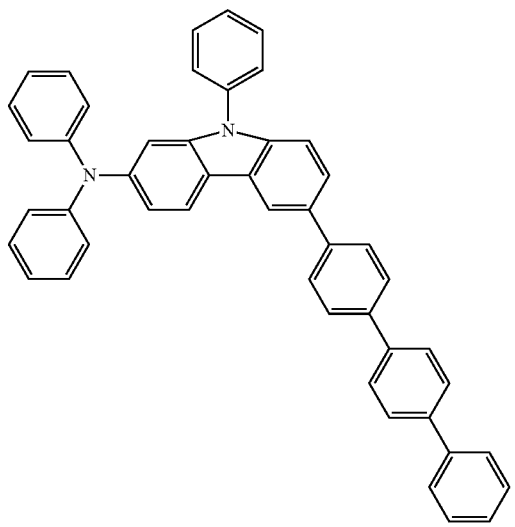
HT26
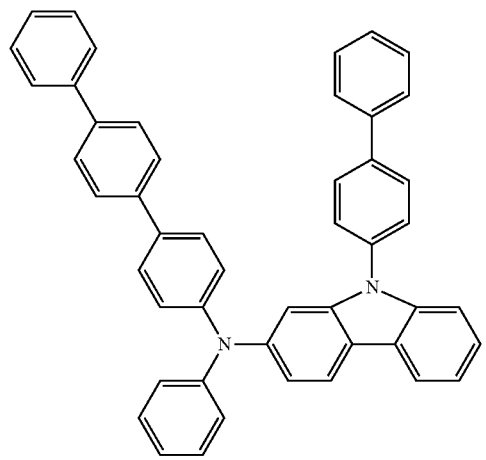
HT27
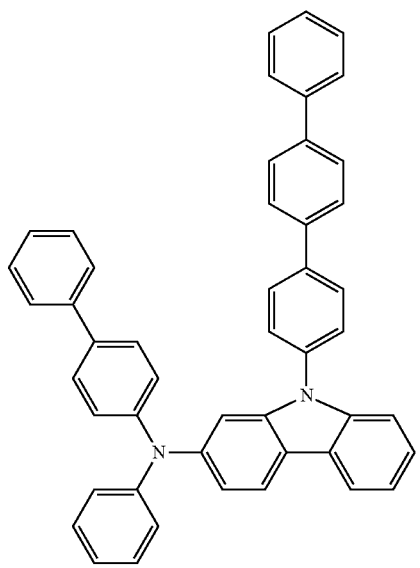
HT28
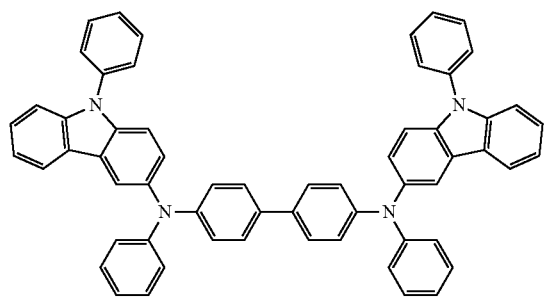
HT29
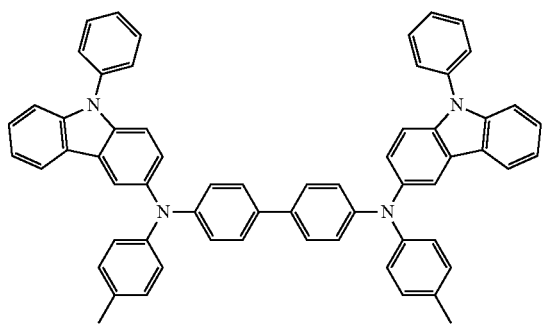

-continued
HT30
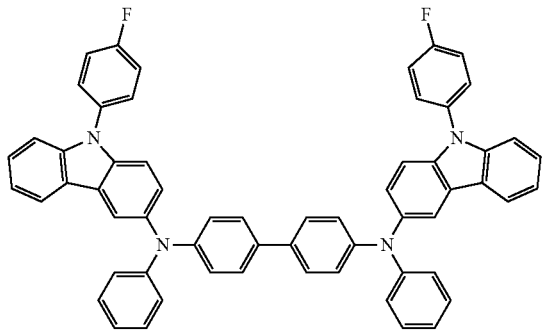
HT31
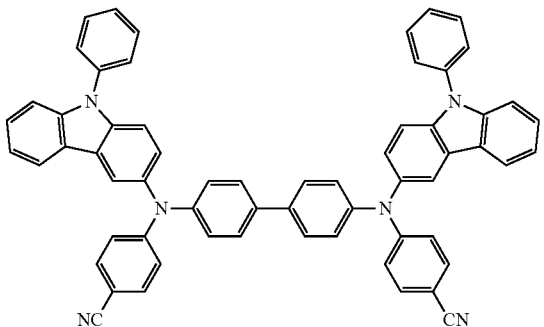
HT32
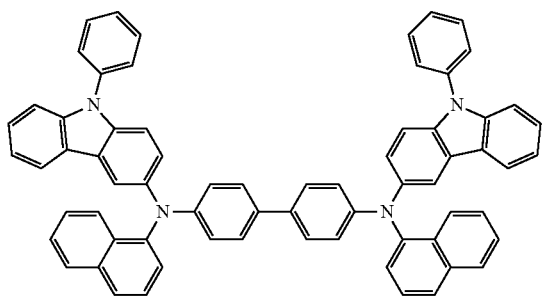
HT33
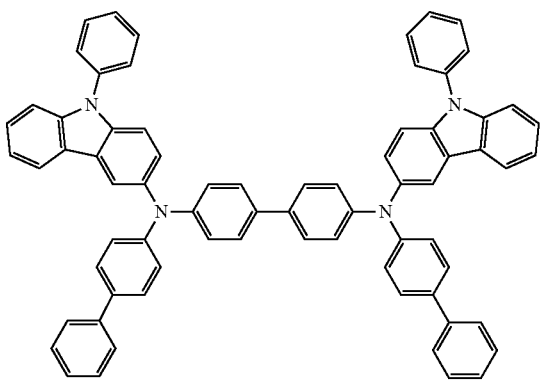
HT34
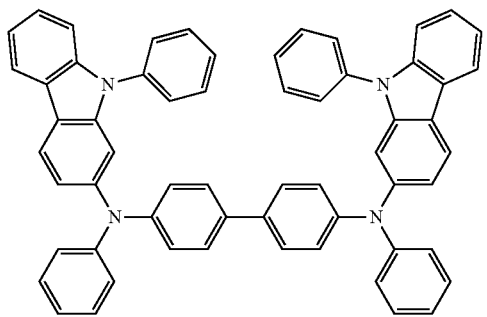
HT35
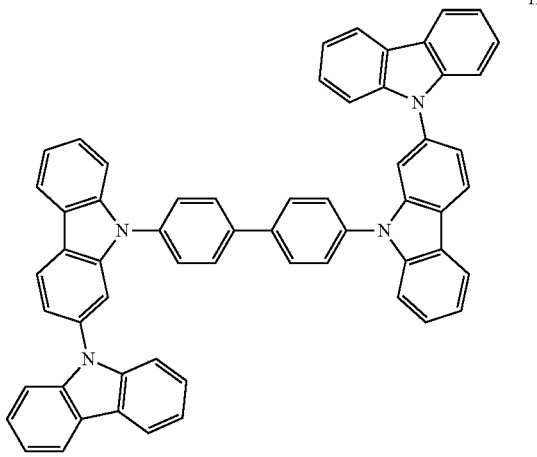
HT36
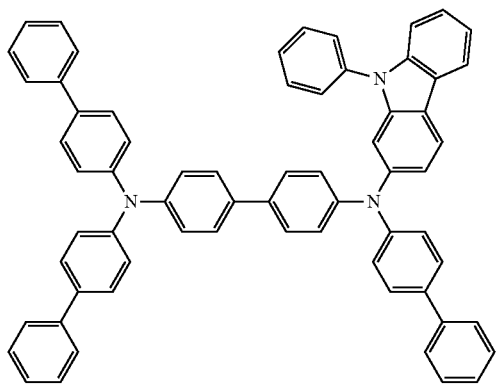
HT37
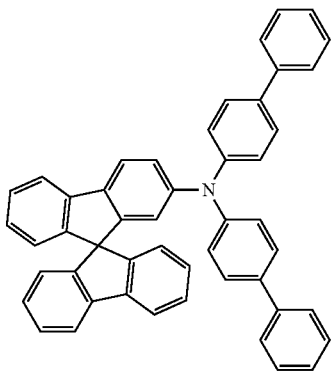

-continued
HT38
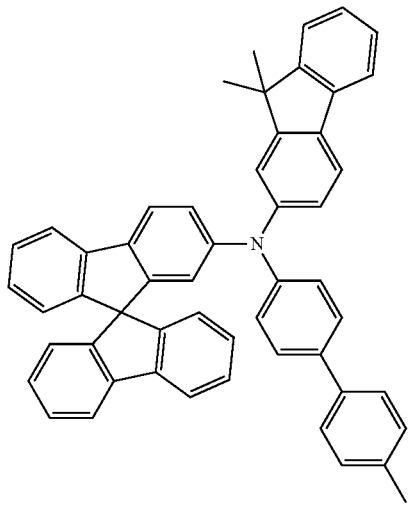
HT39
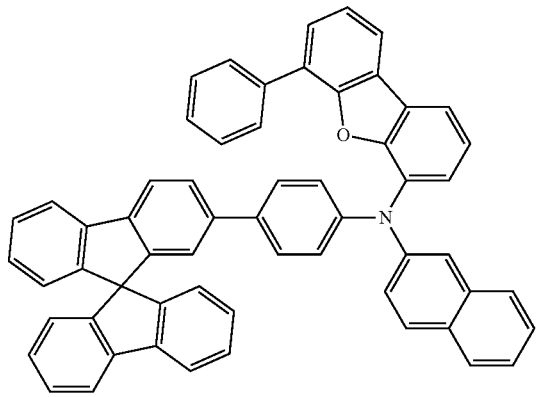
HT40
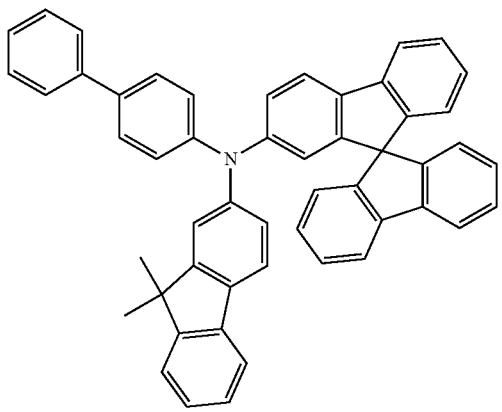
HT41
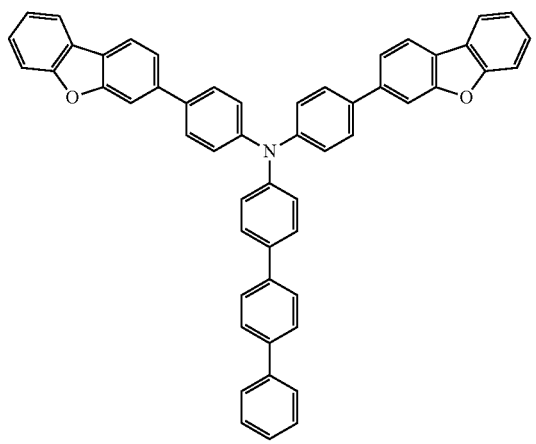
HT42
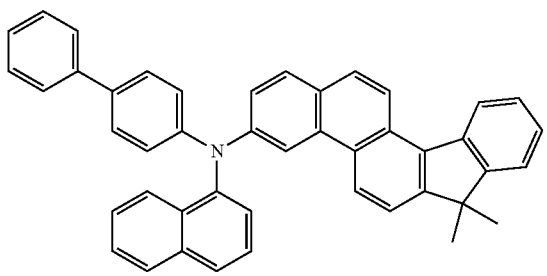
HT43
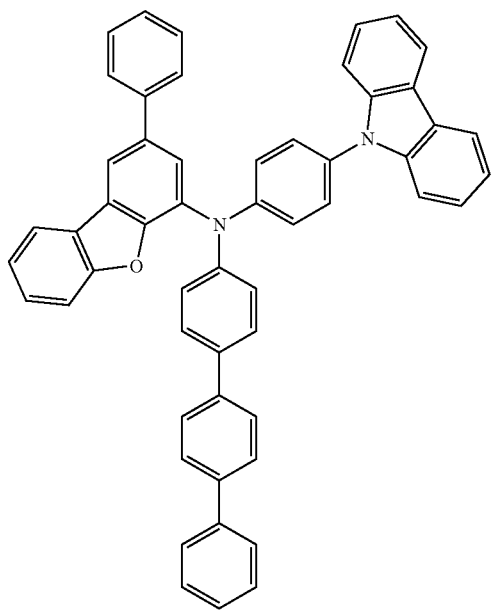

HT44
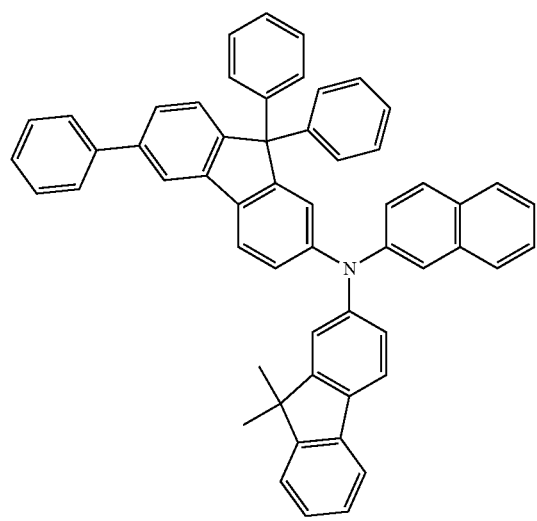
HT45
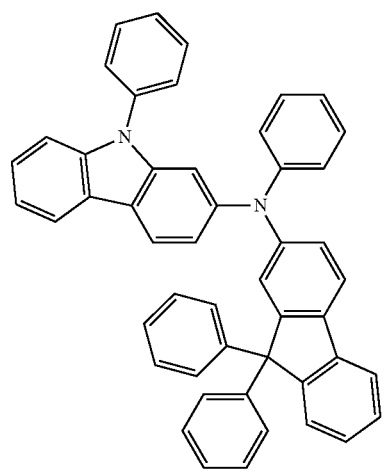
HT46
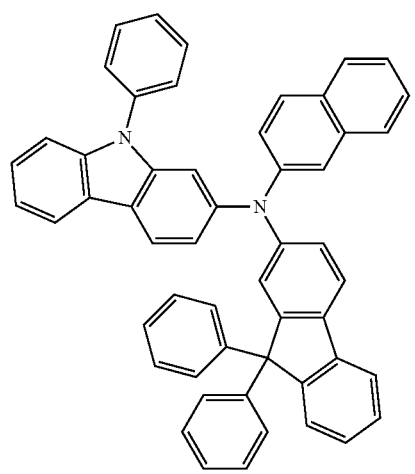
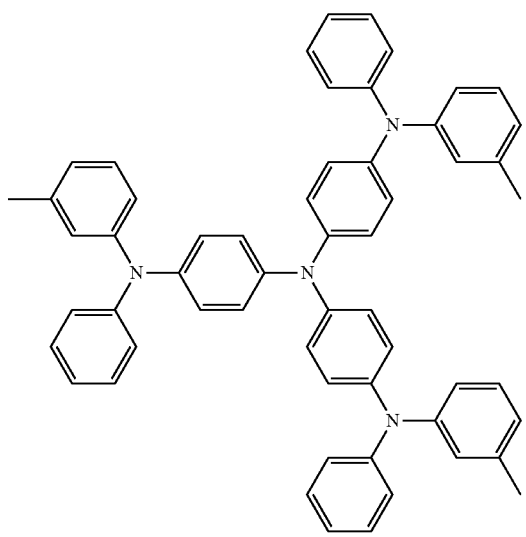
m-MTDATA

-continued
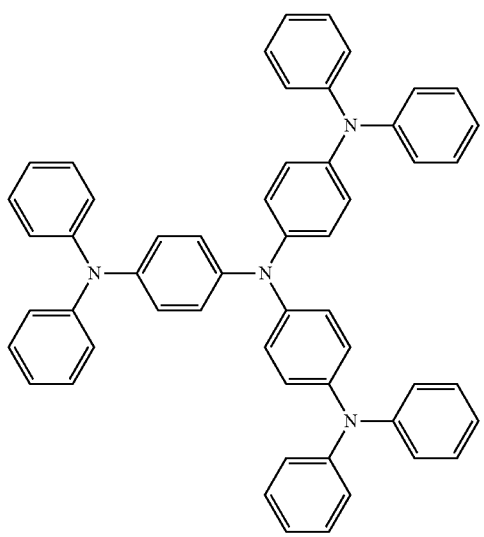
TDATA
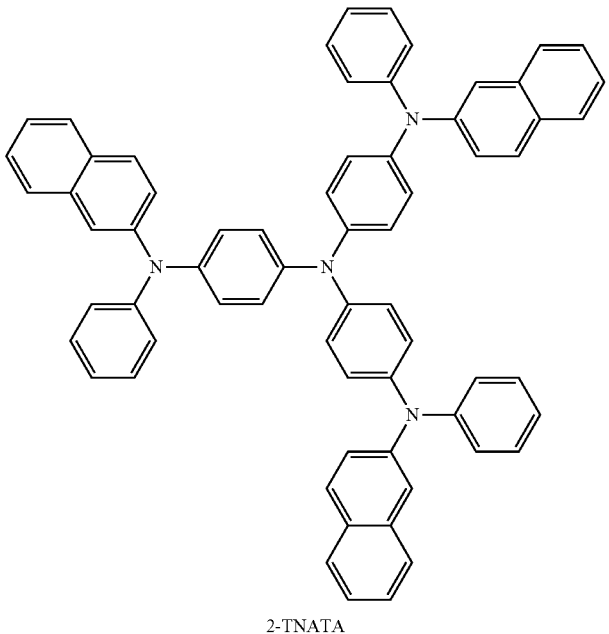
2-TNATA
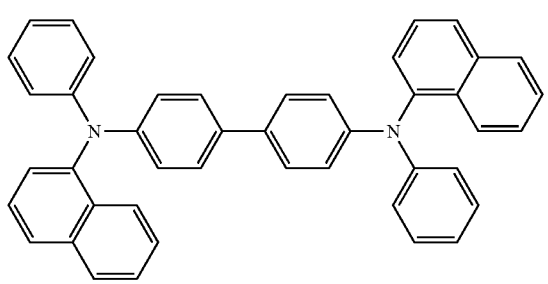
NPB
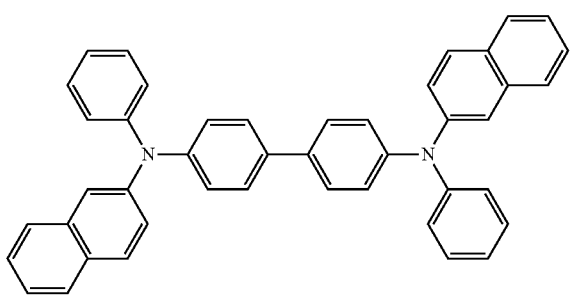
β-NPB
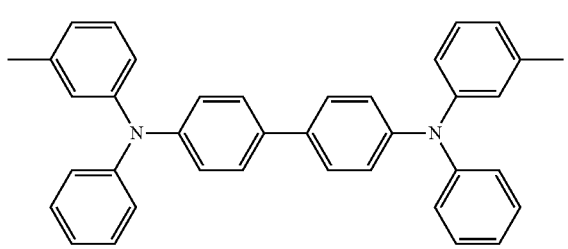
TPD
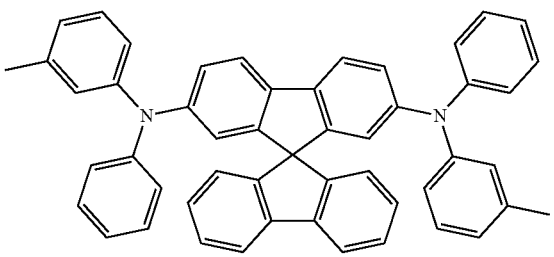
Spiro-TPD
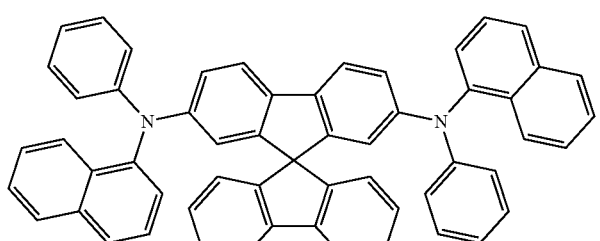
Spiro-NPB
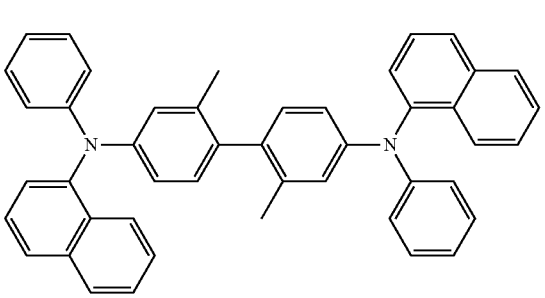
methylated-NPB

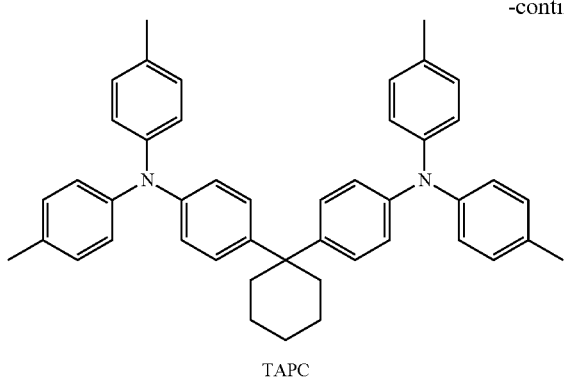

TAPC

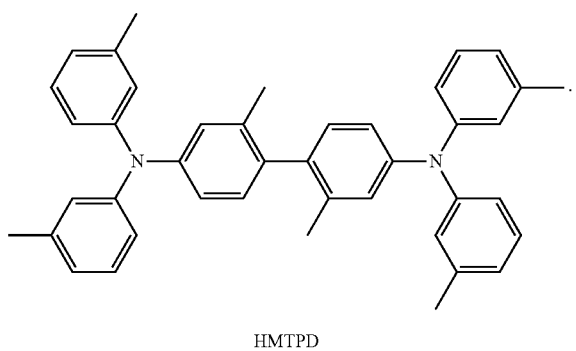

HMTPD

A thickness of the hole transport region 120 may be in a range of about 50 Å to about 10,000 Å, for example, about 100 Å to about 4,000 Å. When the hole transport region 120 includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region 120, the hole injection layer and the hole transport layer are within these ranges, satisfactory hole-transporting characteristics may be obtained without a substantial increase in driving voltage.

The emission auxiliary layer may increase light-emission efficiency by compensating for an optical resonance distance according to the wavelength of light emitted by the emission layer, and the electron blocking layer may block the leakage of electrons from the emission layer to the hole transport region. Materials that may be included in the hole transport region 120 may be included in the emission auxiliary layer and the electron blocking layer.

p-Dopant

The hole transport region may further include, in addition to these materials, a charge-generation material for the improvement of conductive properties. The charge-generation material may be uniformly or non-uniformly dispersed in the hole transport region (for example, in the form of a single layer including (e.g., consisting of) a charge-generation material).

The charge-generation material may be, for example, a p-dopant.

In an embodiment, a lowest unoccupied molecular orbital (LUMO) energy level of the p-dopant may be about −3.5 eV or less.

In an embodiment, the p-dopant may include a quinone derivative, a cyano group-containing compound, a compound containing element EL1 and element EL2 (to be described in more detail below), or any combination thereof.

Examples of the quinone derivative may include TCNQ, F4-TCNQ, and the like.

Examples of the cyano group-containing compound may include HAT-CN, a compound represented by Formula 221 below, and the like

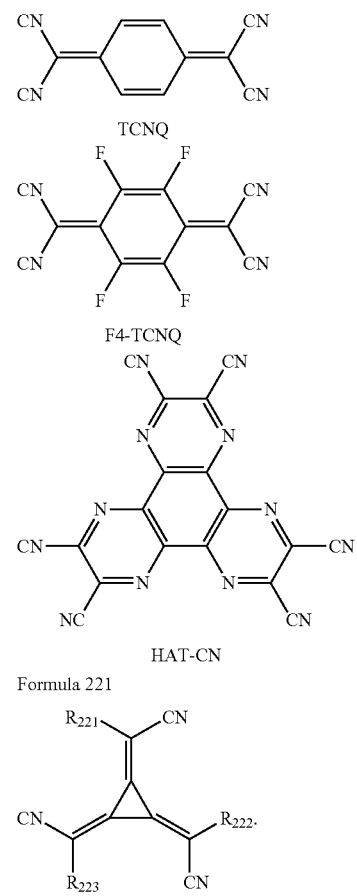

TCNQ

F4-TCNQ

HAT-CN

Formula 221

In Formula 221,
$R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and
at least one of $R_{221}$ to $R_{223}$ may each independently be a $C_3$-$C_{60}$ carbocyclic group or a $C_1$-$C_{60}$ heterocyclic group, each substituted with: a cyano group; —F; —Cl; —Br; —I; a $C_1$-$C_{20}$ alkyl group substituted with a cyano group, —F, —Cl, —Br, —I, or any combination thereof; or any combination thereof.
In the compound containing element EL1 and element EL2, element EL1 may be a metal, a metalloid, or a combination thereof, and element EL2 may be a non-metal, a metalloid, or a combination thereof.

Examples of the metal may include: an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid may include silicon (Si), antimony (Sb), and tellurium (Te).

Examples of the non-metal may include oxygen (O) and halogen (for example, F, Cl, Br, I, etc.).

In an embodiment, examples of the compound containing element EL1 and element EL2 may include a metal oxide, a metal halide (for example, metal fluoride, metal chloride, metal bromide, and/or metal iodide), a metalloid halide (for example, metalloid fluoride, metalloid chloride, metalloid bromide, and/or metalloid iodide), a metal telluride, or any combination thereof.

Examples of the metal oxide may include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide may include alkali metal halide, alkaline earth metal halide, transition metal halide, post-transition metal halide, and lanthanide metal halide.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide may include $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, CuF, CuCl, CuBr, CuI, etc.), silver halide (for example, AgF, AgCl, AgBr, AgI, etc.), and gold halide (for example, AuF, AuCl, AuBr, AuI, etc.).

Examples of the post-transition metal halide may include zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide may include YbF, $YbF_2$, $YbF_3$, $SmF_3$, YbCl, $YbCl_2$, $YbCl_3$ $SmCl_3$, YbBr, $YbBr_2$, $YbBr_3$, $SmBr_3$, YbI, $YbI_2$, $YbI_3$, and $SmI_3$.

Examples of the metalloid halide may include antimony halide (for example, $SbCl_5$, etc.).

Examples of the metal telluride may include alkali metal telluride (for example, $Li_2Te$, $Na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), and lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device, the emission layer may be patterned into a red emission layer, a green emission layer, and/or a blue emission layer, according to a sub-pixel. In an embodiment, the emission layer may have a stacked structure of two or more layers of a red emission layer, a green emission layer, and a blue emission layer, in which the two or more layers contact each other or are separated from each other. In one or more embodiments, the emission layer may include two or more materials of a red light-emitting material, a green light-emitting material, and a blue light-emitting material, in which the two or more materials are mixed with each other in a single layer to emit white light.

The emission layer may include a host and a dopant. The dopant may include a phosphorescent dopant, a fluorescent dopant, or any combination thereof.

An amount of the dopant in the emission layer may be from about 0.01 parts by weight to about 15 parts by weight based on 100 parts by weight of the host.

In an embodiment, the emission layer may include a quantum dot.

In an embodiment, the emission layer may include a delayed fluorescence material. The delayed fluorescence material may act (e.g., serve) as a host or a dopant in the emission layer.

A thickness of the emission layer may be in a range of about 100 Å to about 1,000 Å, for example, about 200 Å to about 600 Å. When the thickness of the emission layer is within these ranges, suitable (e.g., excellent) light-emission characteristics may be obtained without a substantial increase in driving voltage.

Host

The host may include a compound represented by Formula 301 below:

$$[Ar_{301}]_{xb11}-[(L_{301})_{xb1}-R_{301}]_{xb21} \quad \text{Formula 301}$$

wherein, in Formula 301, $Ar_{301}$ and $L_{301}$ may each independently be a $C_3$-$C_{60}$ carbocyclic group unsubstituted or substituted with at least one $R_{10a}$ or a $C_1$-$C_6$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{301})(Q_{302})(Q_{303})$, $-N(Q_{301})(Q_{302})$, $-B(Q_{301})(Q_{302})$, $-C(=O)(Q_{301})$, $-S(=O)_2(Q_{301})$, or $-P(=O)(Q_{301})(Q_{302})$, xb21 may be an integer from 1 to 5, and $Q_{301}$ to $Q_{303}$ are each the same as described in connection with $Q_1$.

In an embodiment, when xb11 in Formula 301 is 2 or more, two or more of $Ar_{301}(s)$ may be linked to each other via a single bond.

In an embodiment, the host may include a compound represented by Formula 301-1, a compound represented by Formula 301-2, or any combination thereof:

Formula 301-1

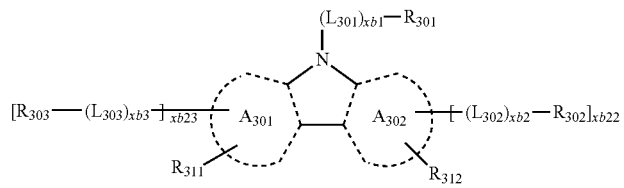

Formula 301-2

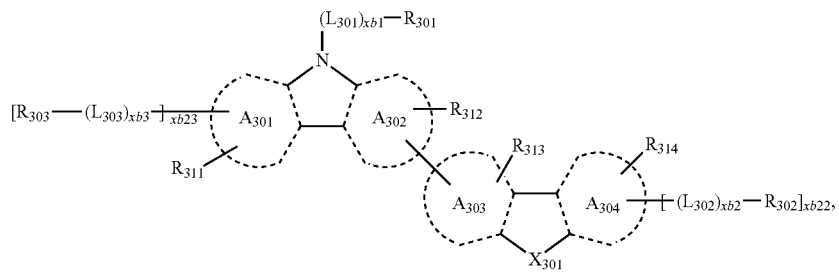

wherein, in Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N—[($L_{304}$)xb4-$R_{304}$], $C(R_{304})(R_{305})$, or $Si(R_{304})(R_{305})$, xb22 and xb23 may each independently be 0, 1, or 2, $L_{301}$, xb1, and $R_{301}$ are each the same as described in the present specification, $L_{302}$ to $L_{304}$ are each the same as described in connection with $L_{301}$, xb2 to xb4 are each independently the same as described in connection with xb1, and $R_{302}$ to $R_{305}$ and $R_{311}$ to $R_{314}$ are each the same as described in connection with $R_{301}$.

In an embodiment, the host may include an alkaline earth metal complex, a post-transition metal complex, or a combination thereof. In an embodiment, the host may include a Be complex (for example, Compound H55), an Mg complex, a Zn complex, or a combination thereof.

In an embodiment, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolyl-benzene (mCP), 1,3,5-tri(carbazol-9-yl)benzene (TCP), or any combination thereof:

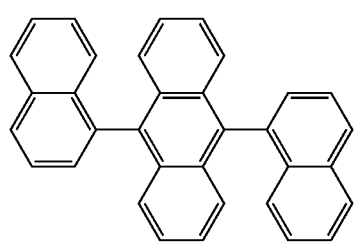

H1

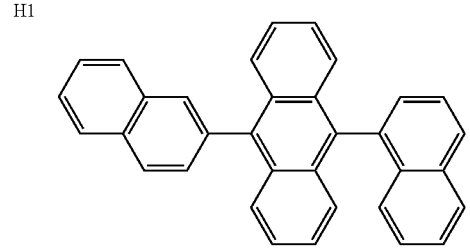

H2

H3
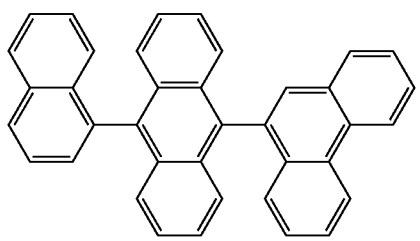
H4
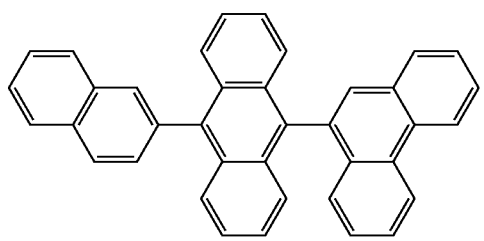
H5
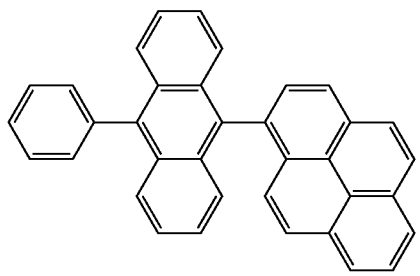
H6
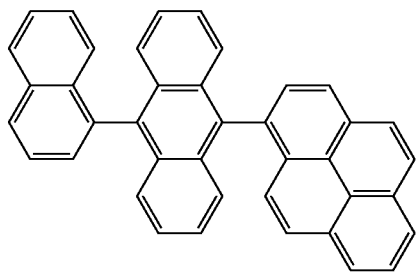
H7
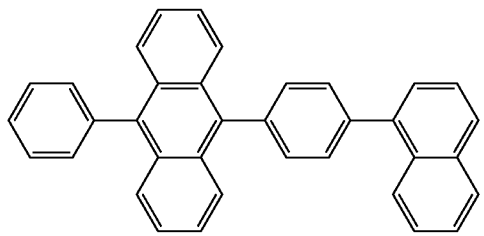
H8
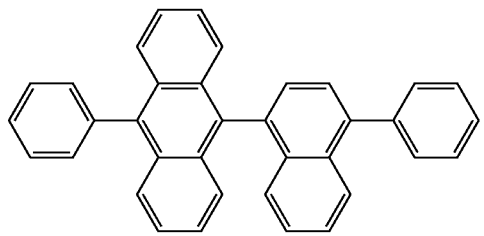
H9
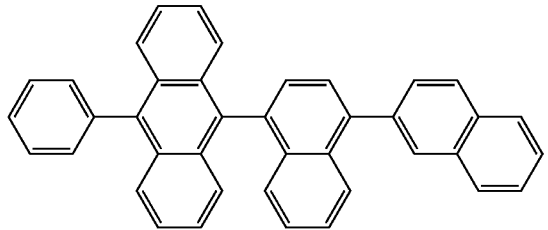
H10
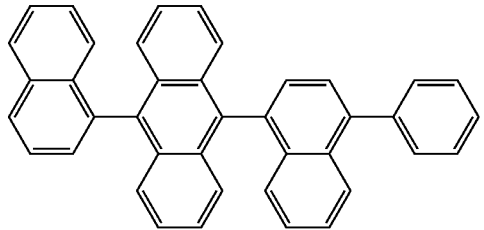
H11
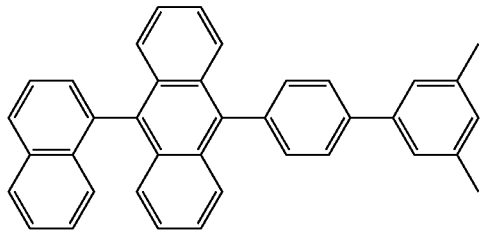
H12
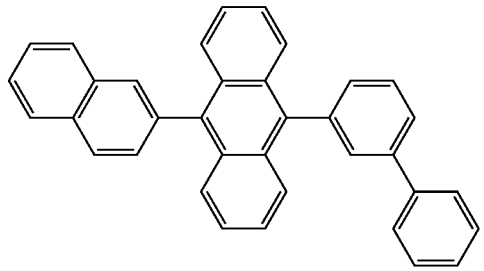

-continued
H13
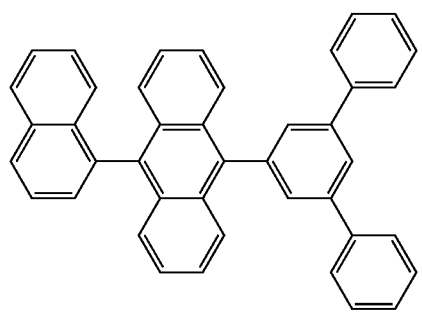
H14
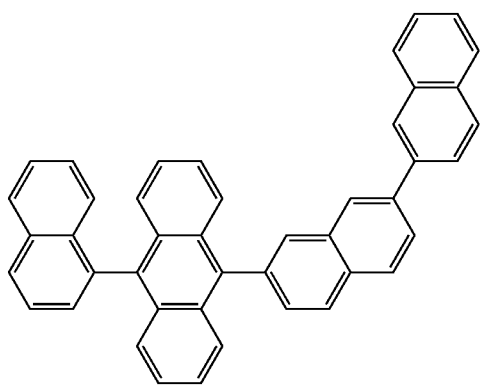
H15
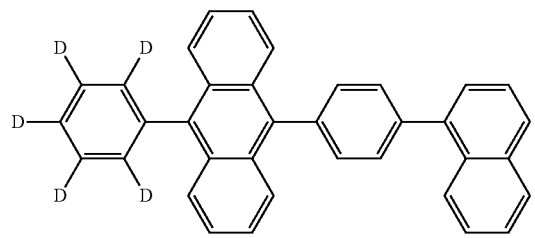
H16
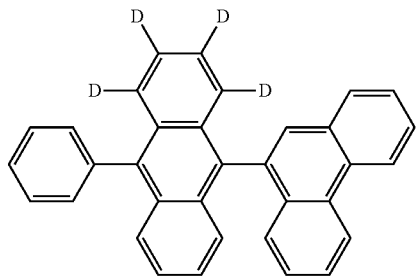
H17
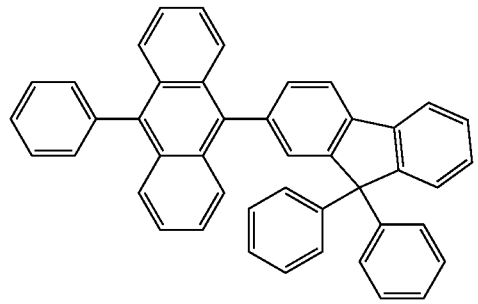
H18
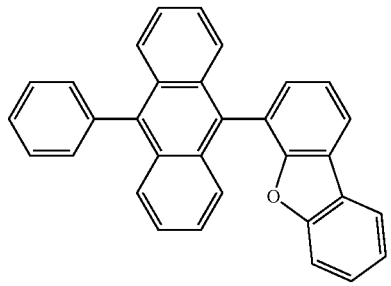
H19
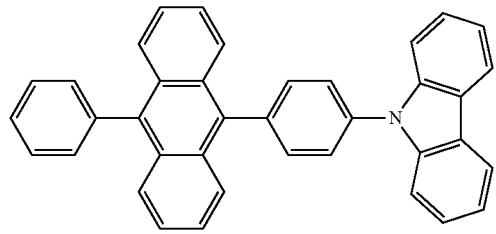
H20
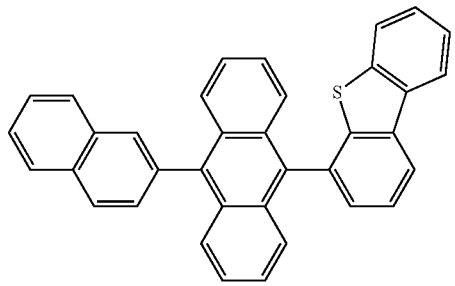

-continued
H21
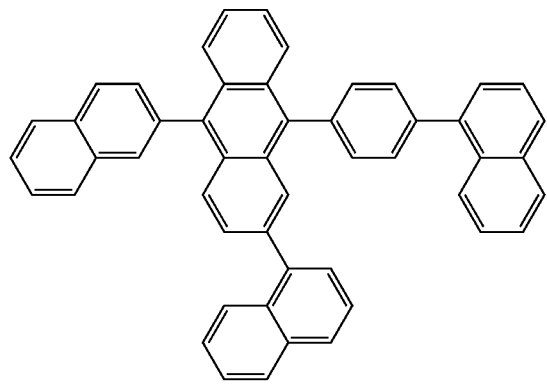
H22
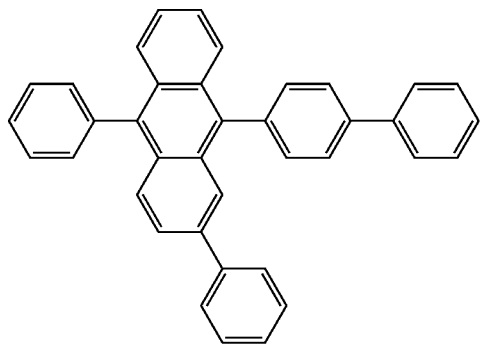
H23
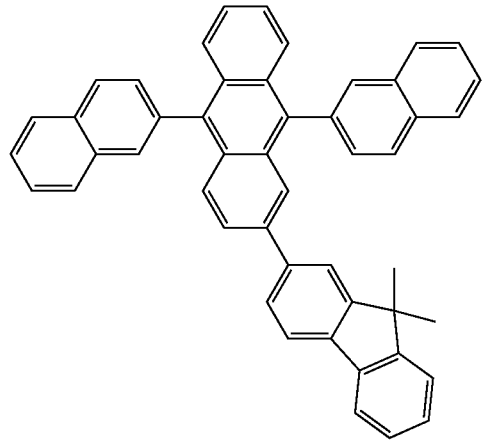
H24
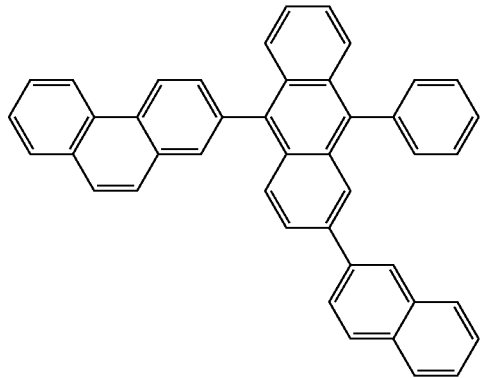
H25
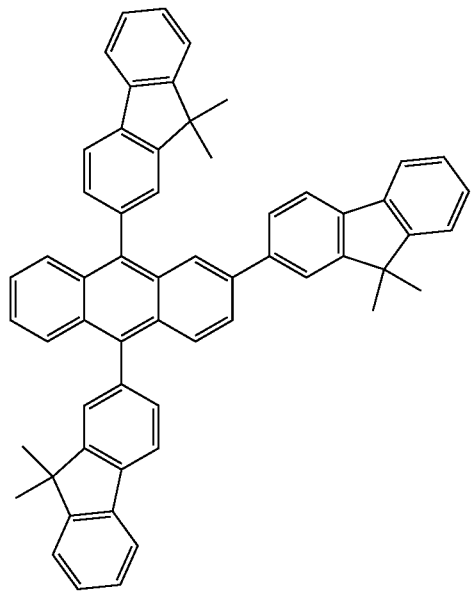
H26
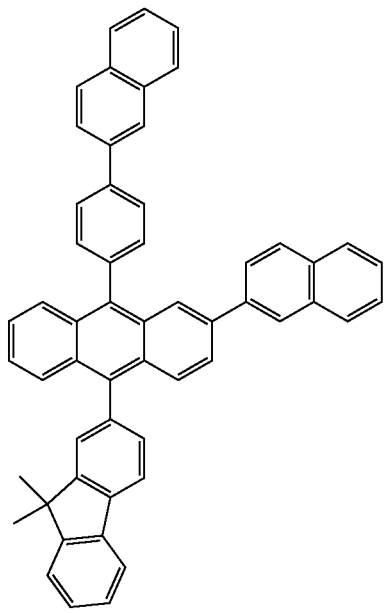

-continued
H27
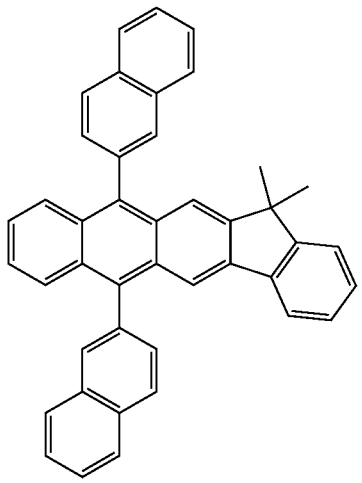
H28
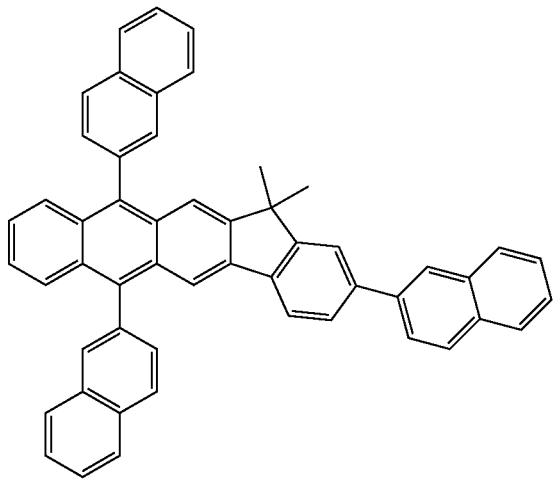
H29
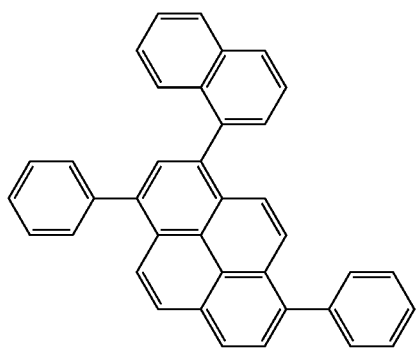
H30
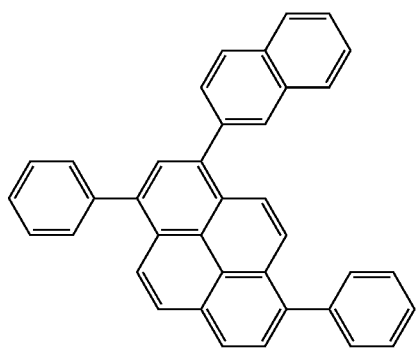
H31
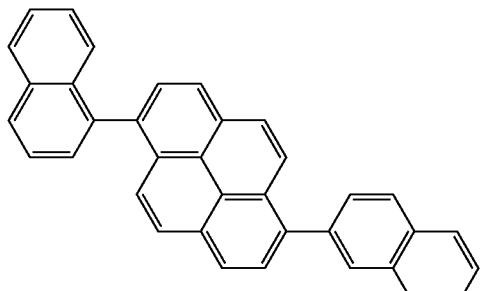
H32
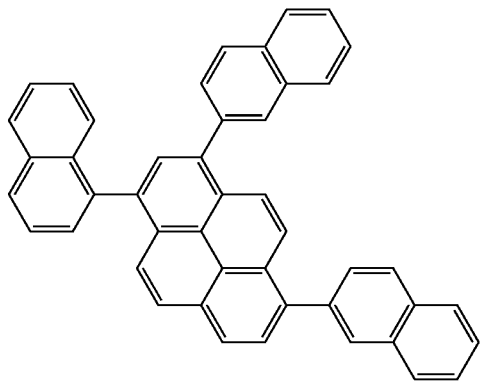
H33
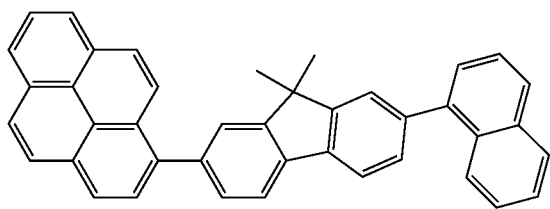
H34
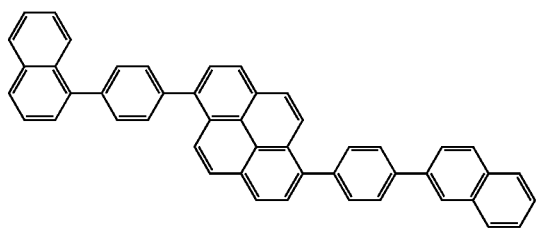

H35
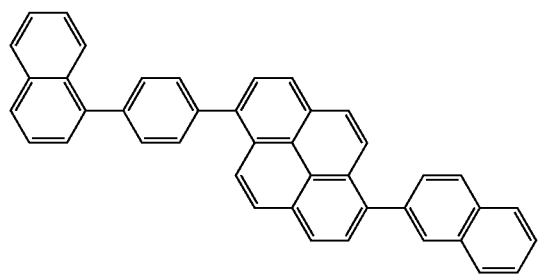
H36
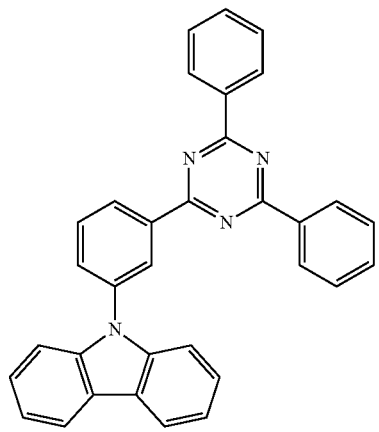
H37
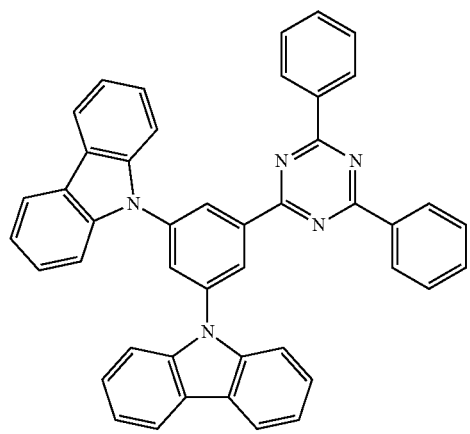
H38
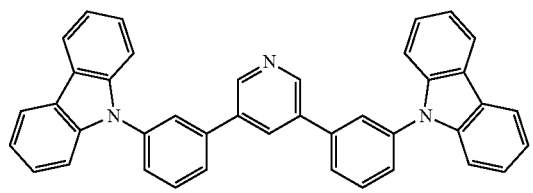
H39
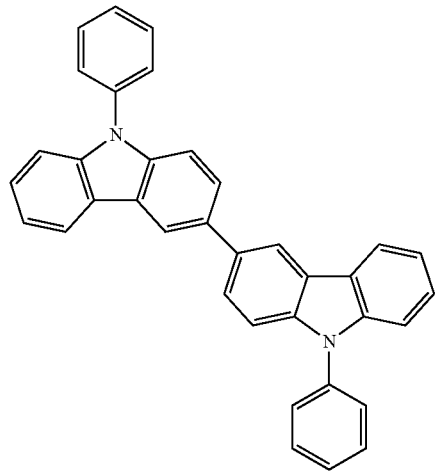
H40
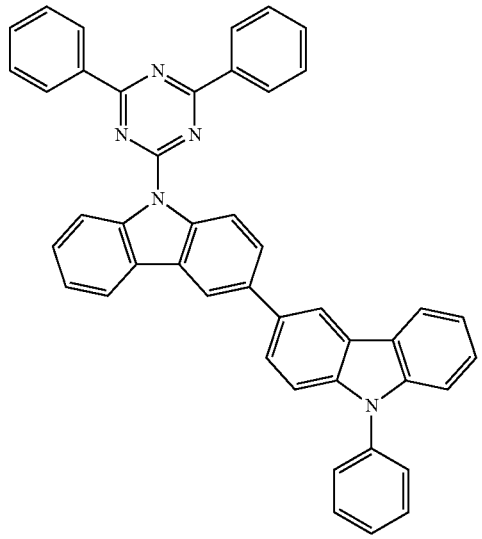

-continued
H41
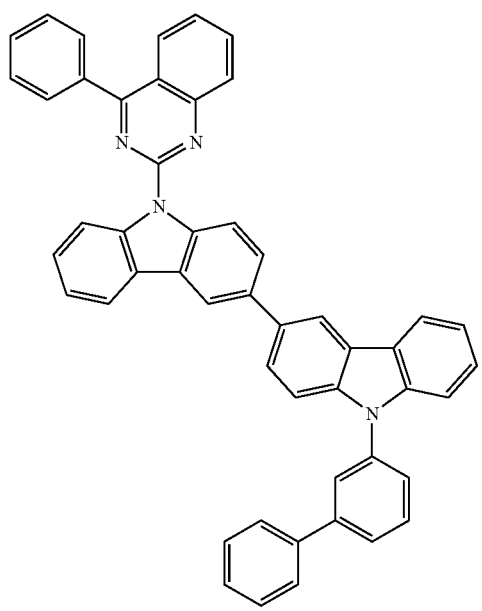
H42
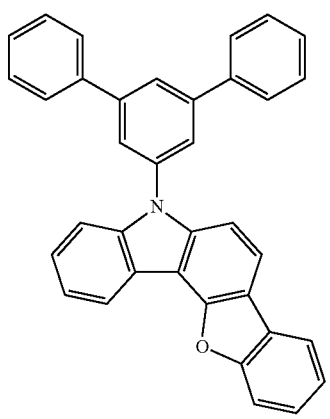
H43
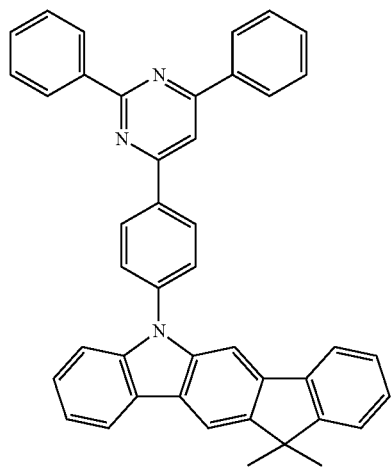
H44
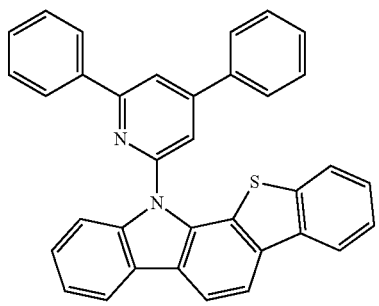
H45
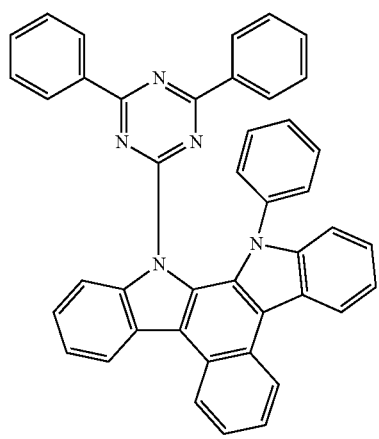
H46
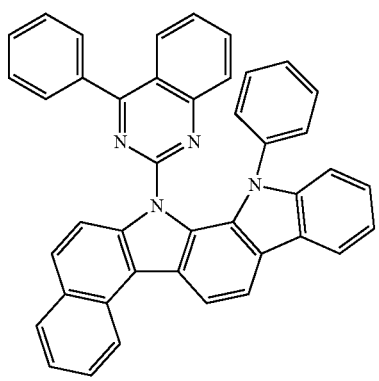

-continued
H47
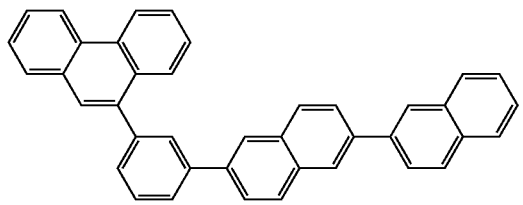
H48
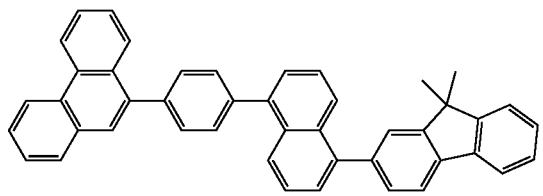
H49
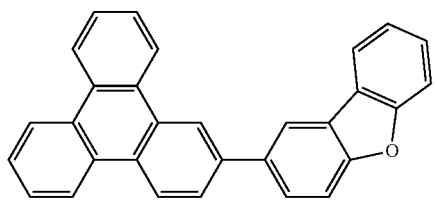
H50
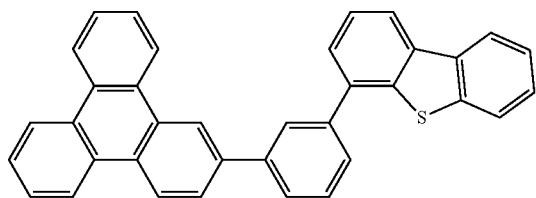
H51
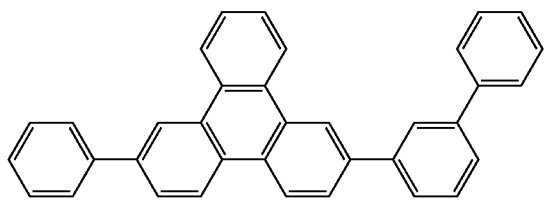
H52
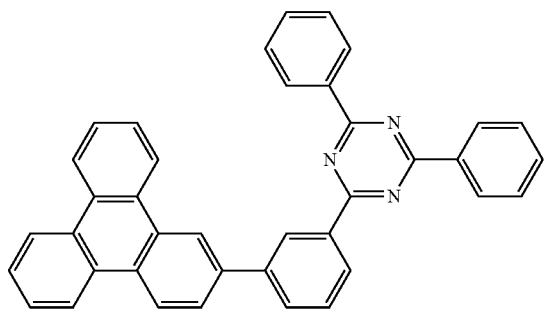
H53
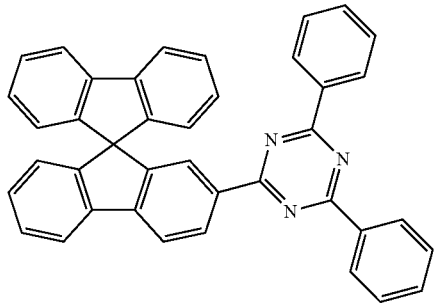
H54
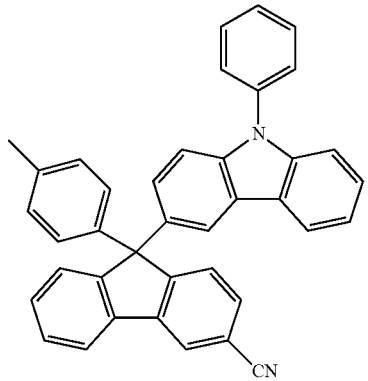
H55
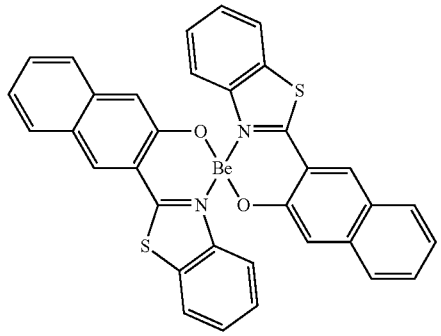
H56
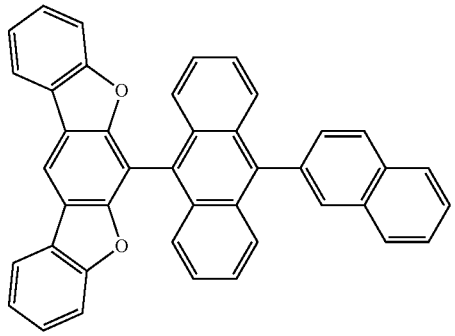

-continued
H57
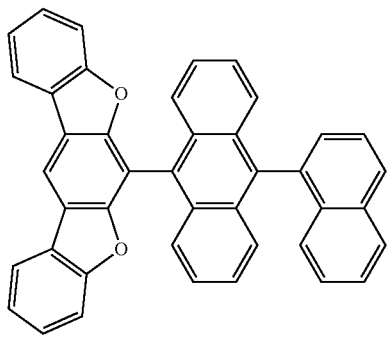
H58
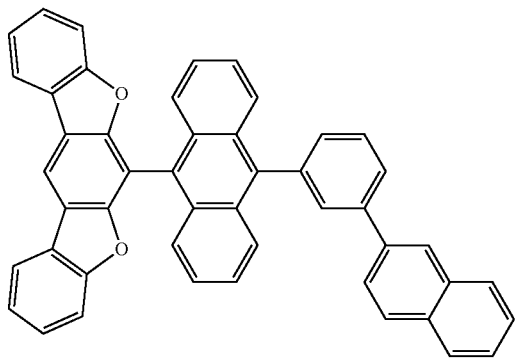
H59
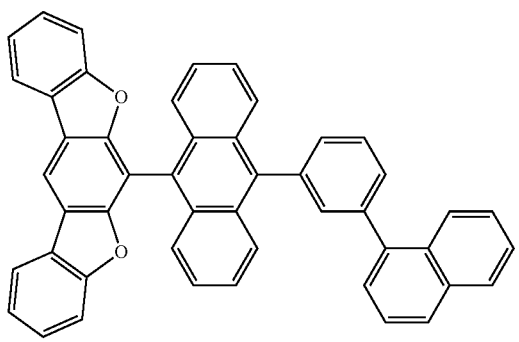
H60
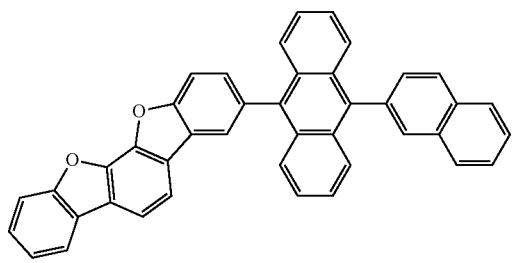
H61
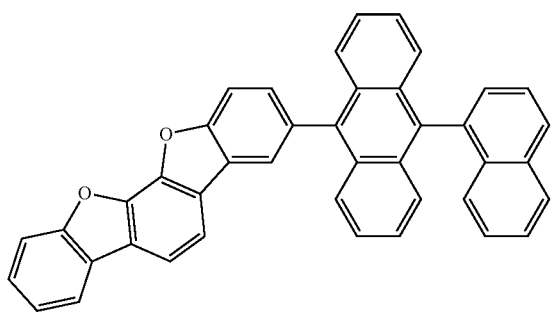
H62
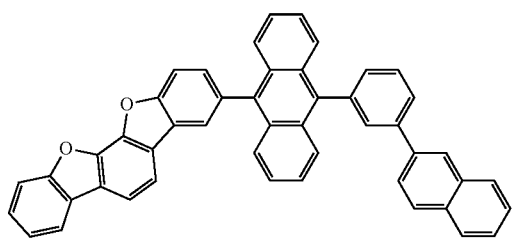
H63
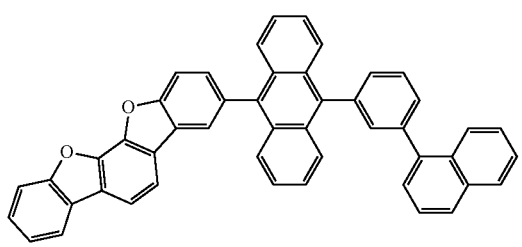
H64
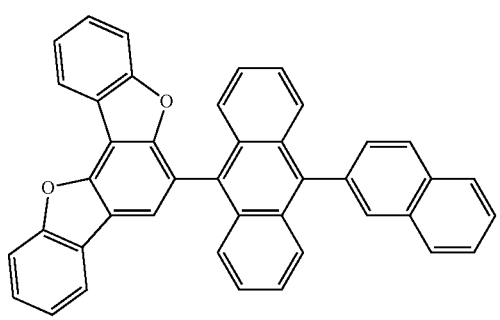

-continued
H65
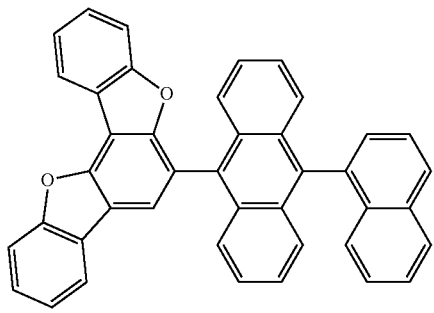
H66
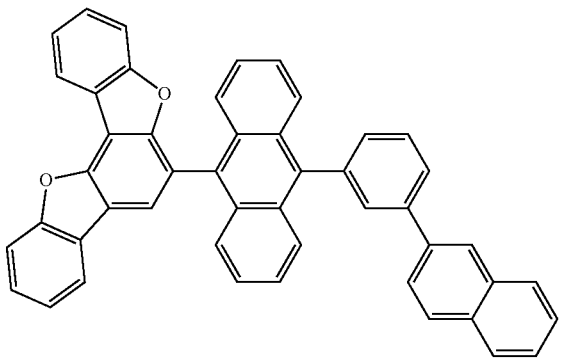
H67
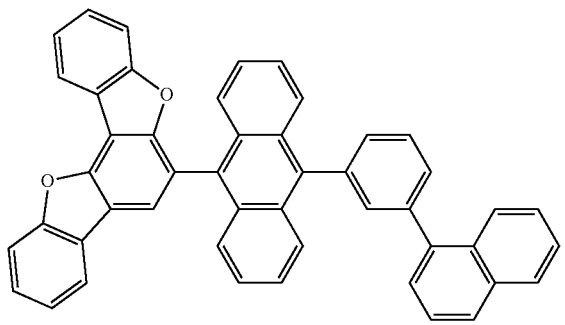
H68
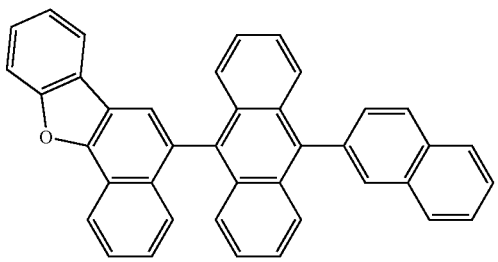
H69
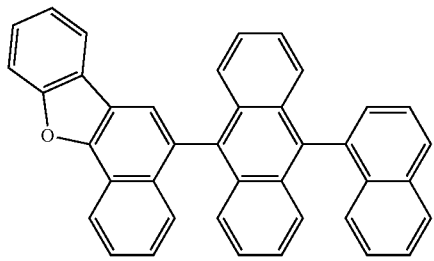
H70
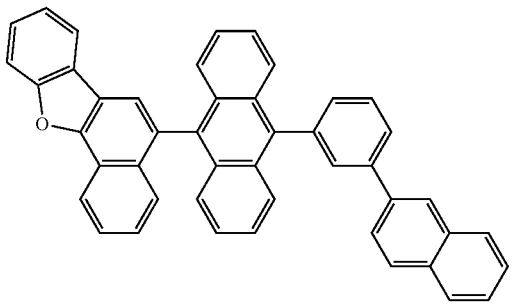
H71
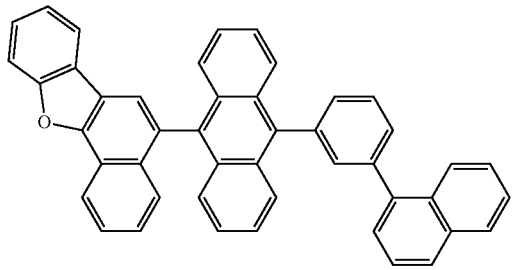
H72
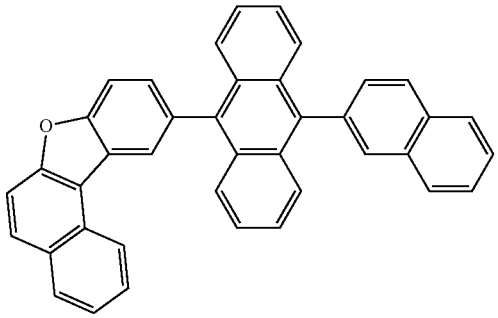

-continued
H73
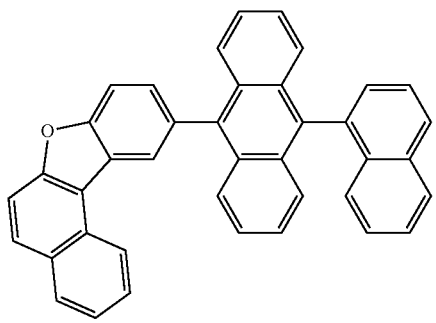
H74
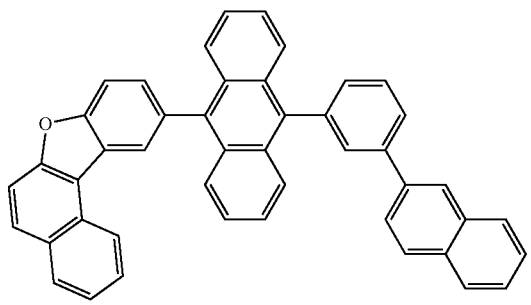
H75
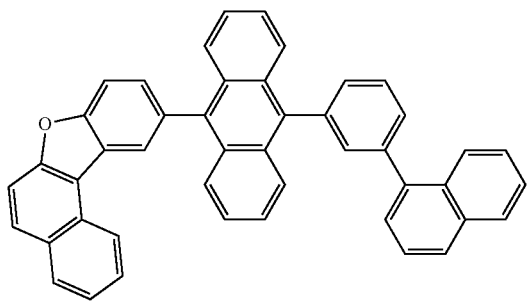
H76
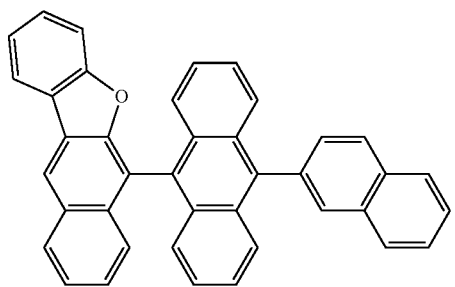
H77
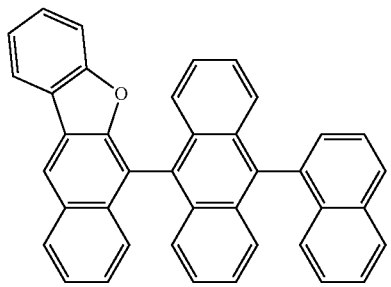
H78
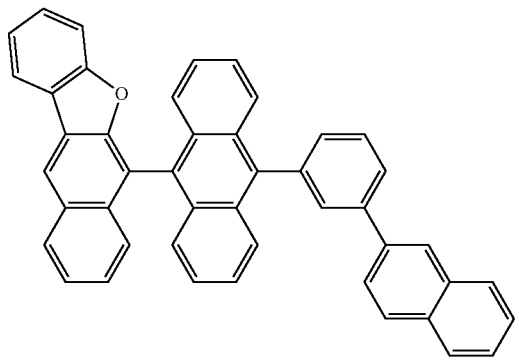
H79
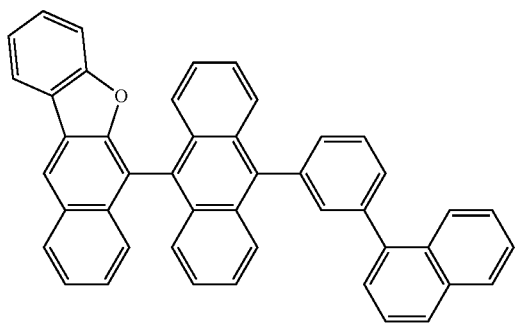
H80
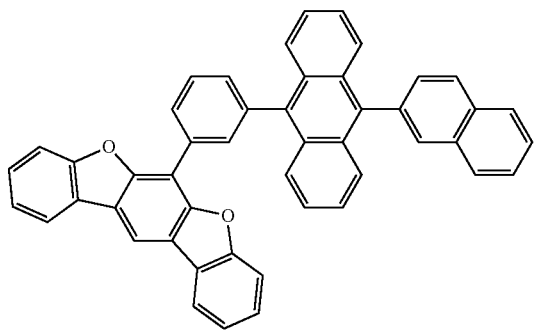

-continued
H81
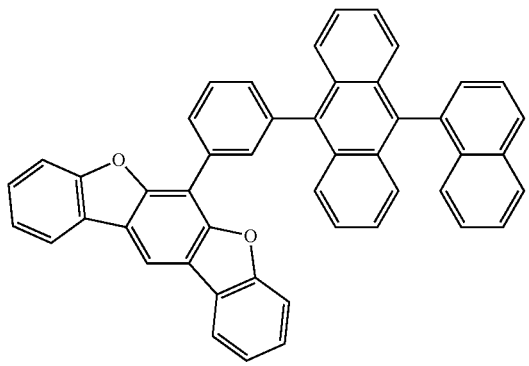
H82
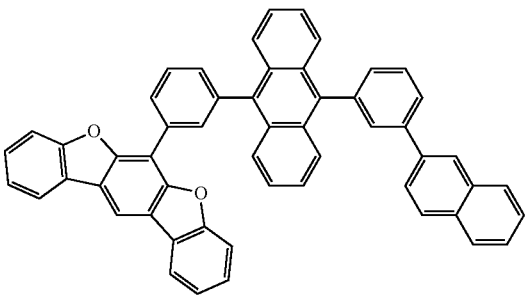
H83
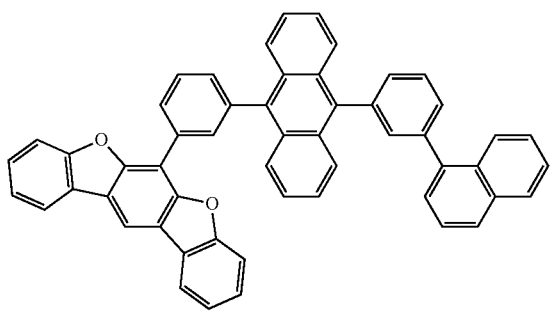
H84
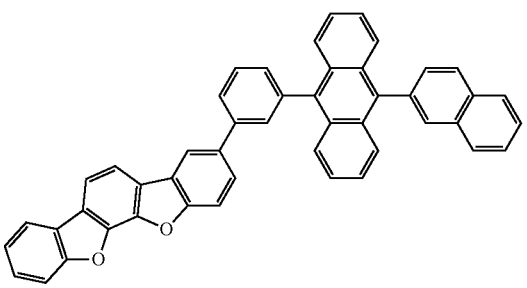
H85
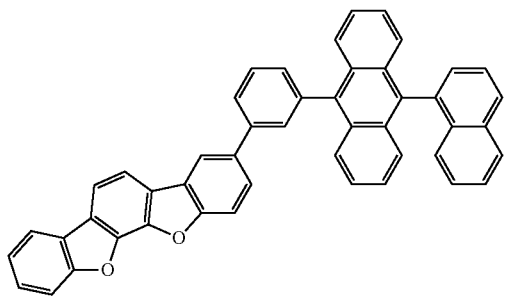
H86
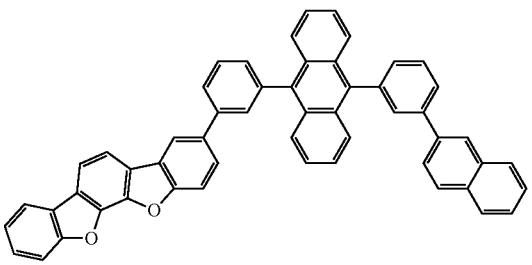
H87
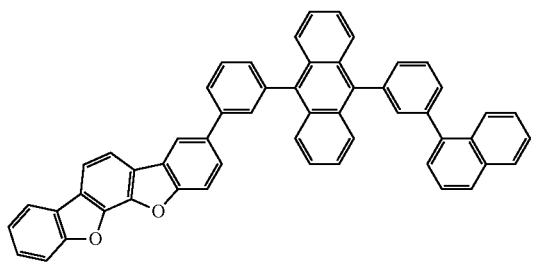
H88
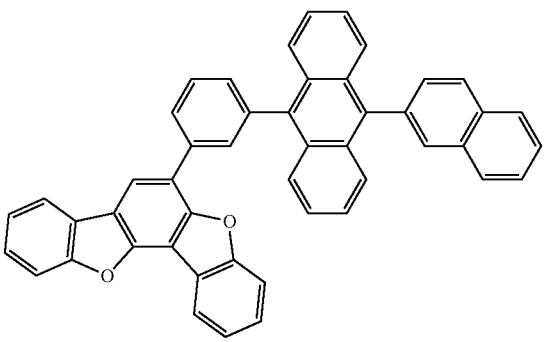

-continued
H89
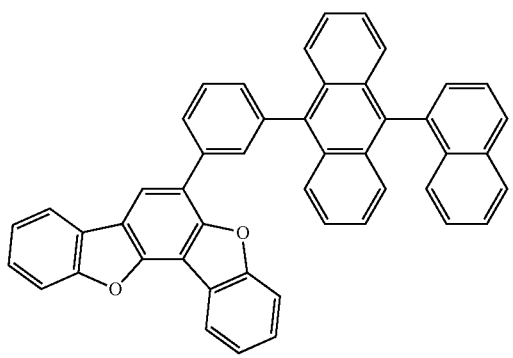
H90
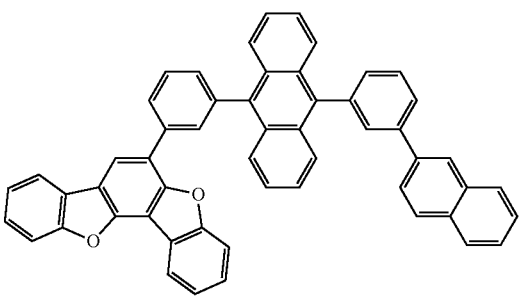
H91
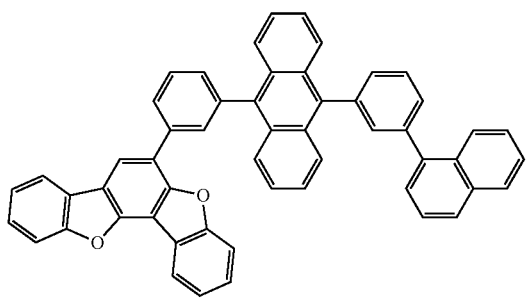
H92
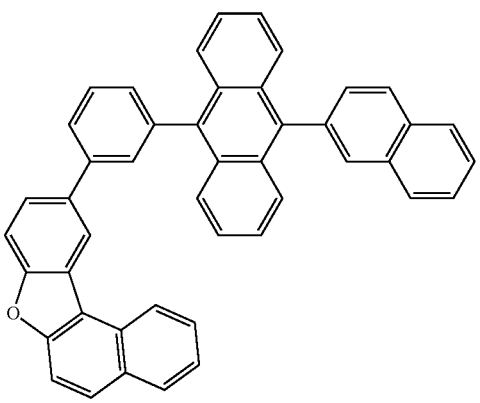
H93
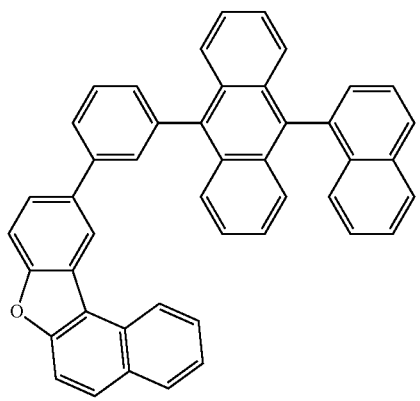
H94
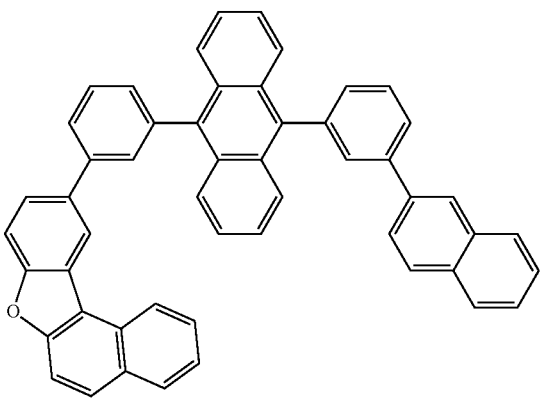
H95
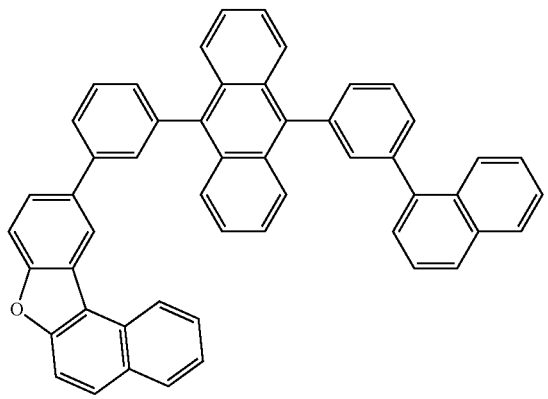
H96
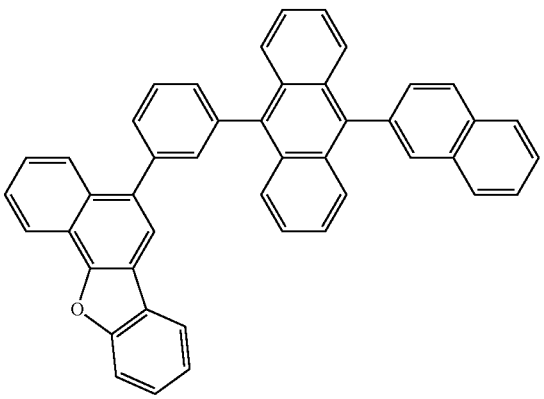

-continued
H97
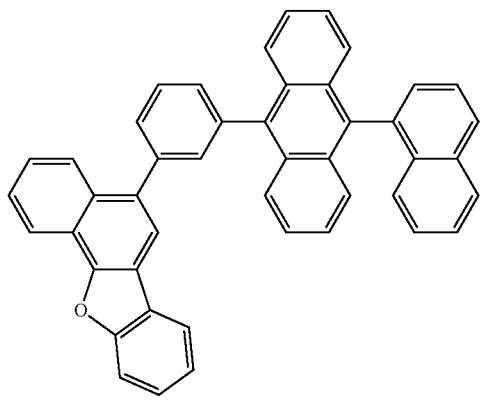
H98
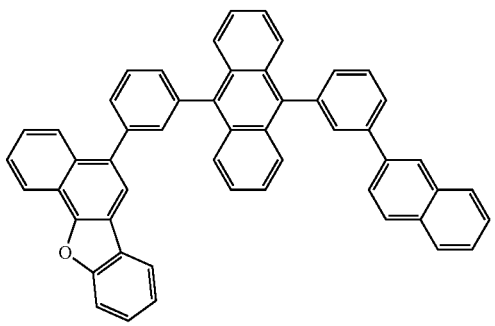
H99
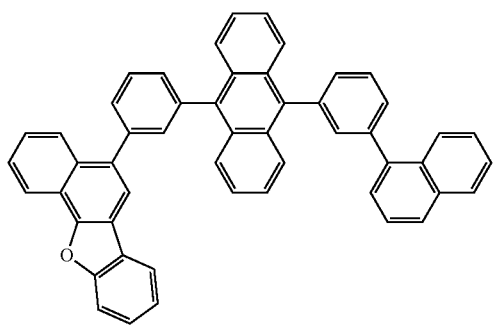
H100
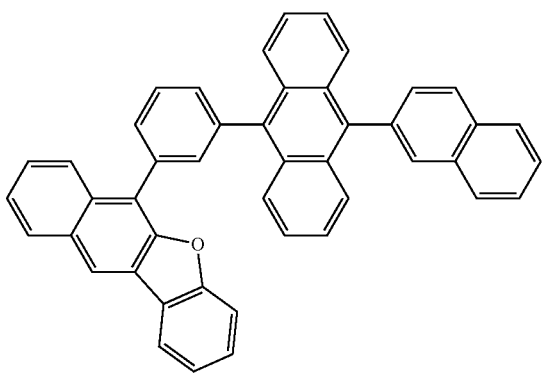
H101
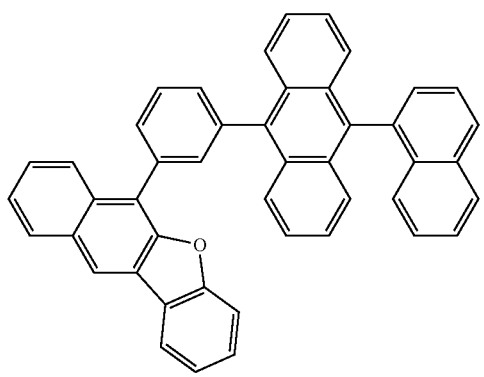
H102
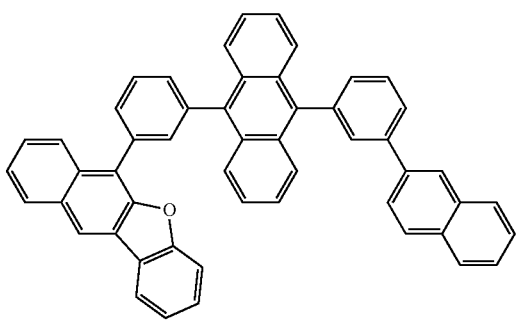
H103
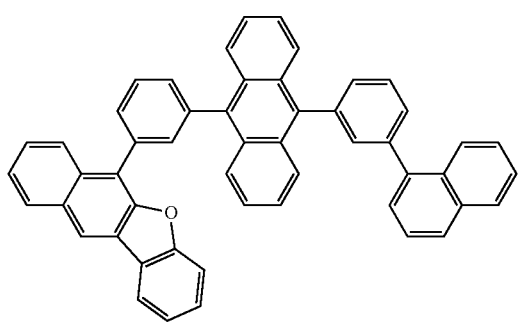
H104
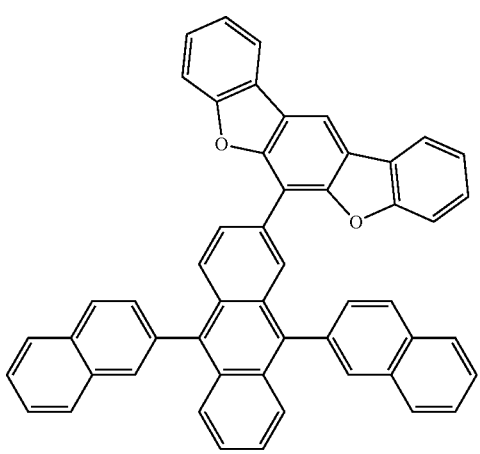

-continued
H105
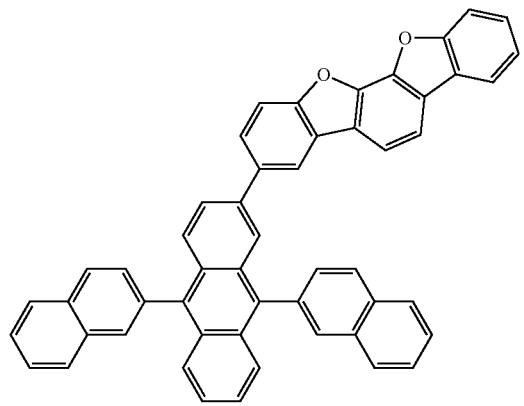
H106
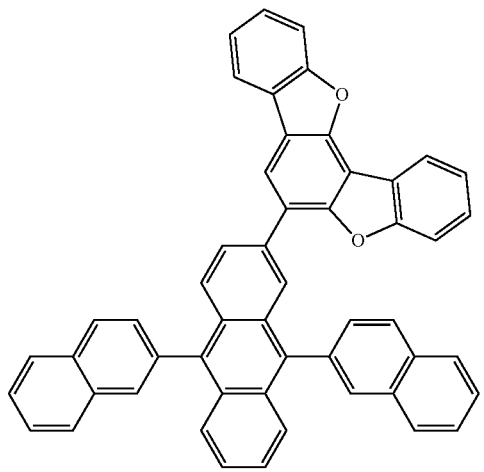
H107
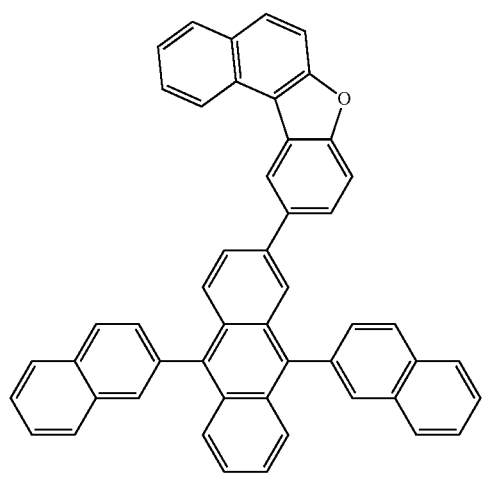
H108
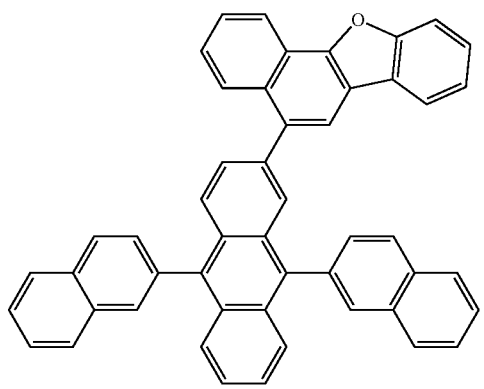
H109
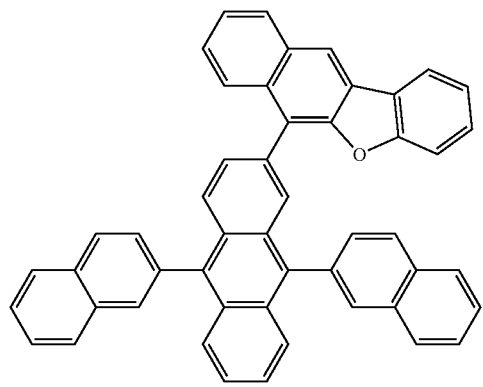
H110
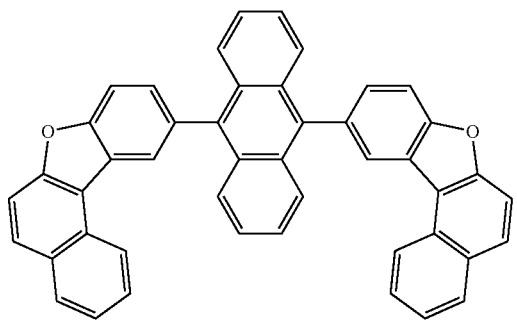
H111
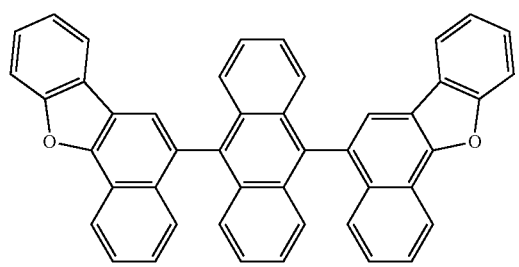
H112
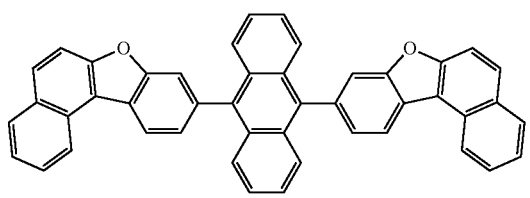

-continued
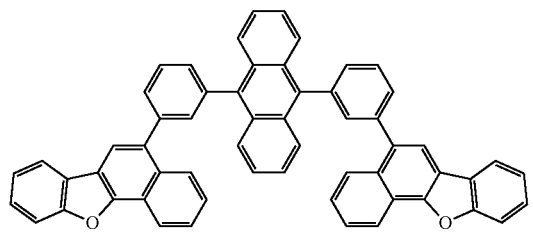
H113
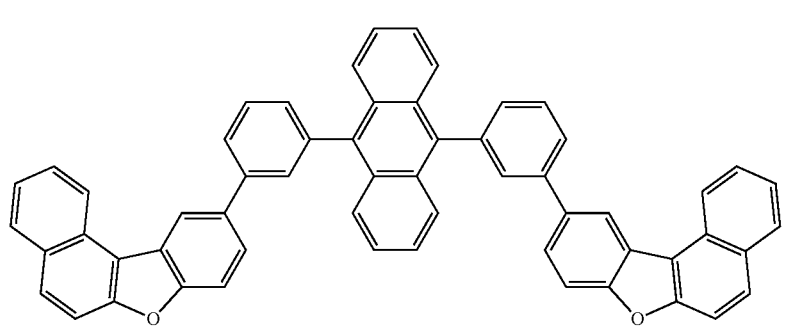
H114
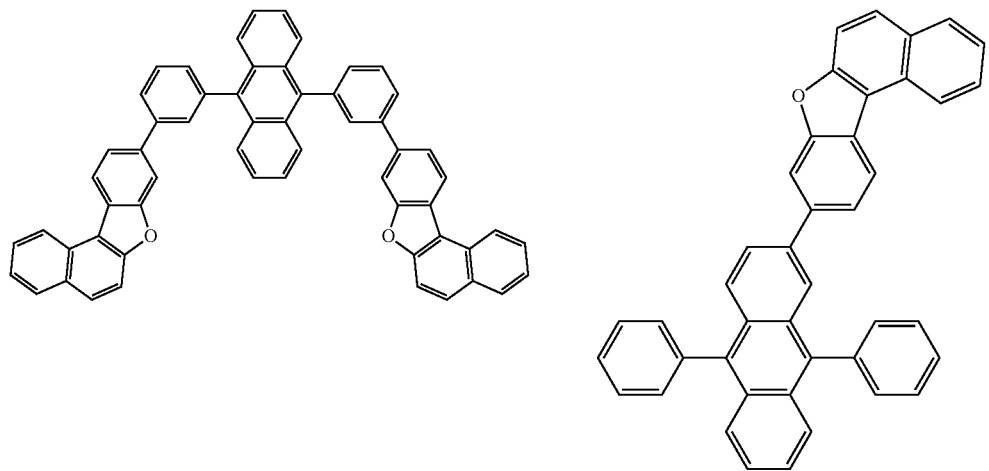
H115
H116
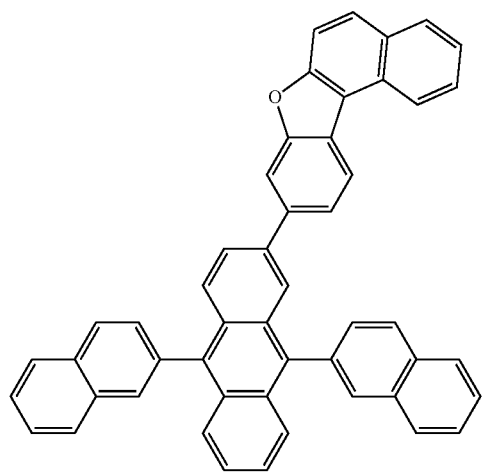
H117
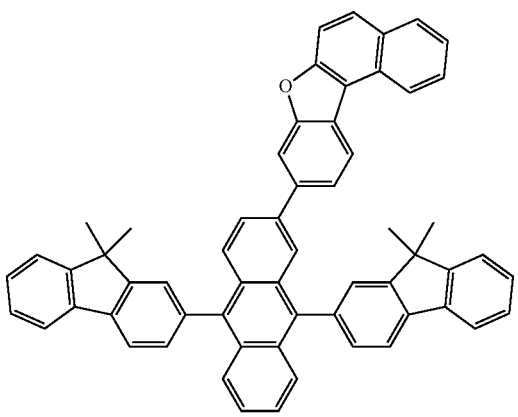
H118

-continued
H119
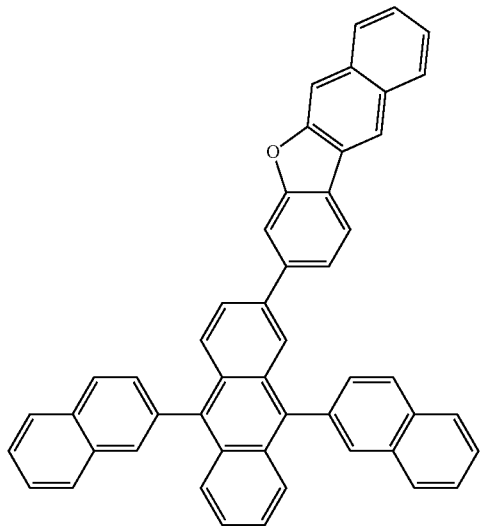
H120
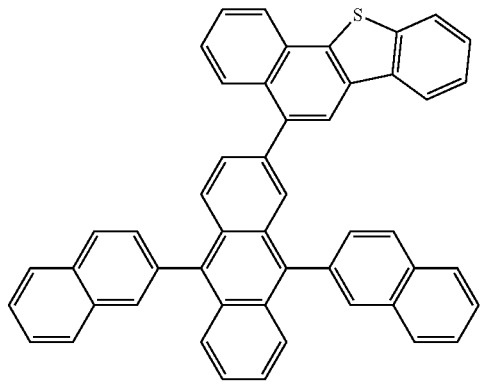
H121
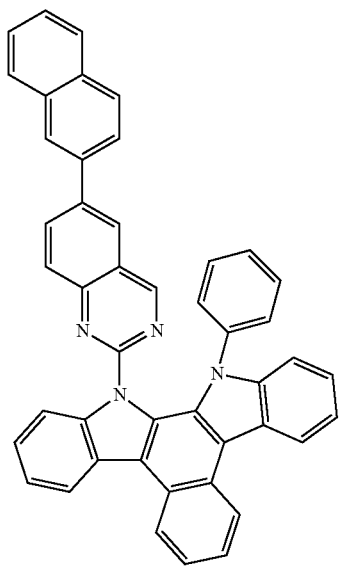
H122
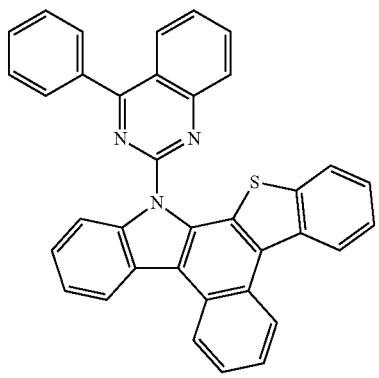
H123
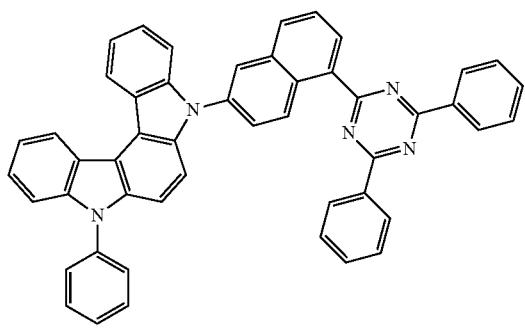
H124
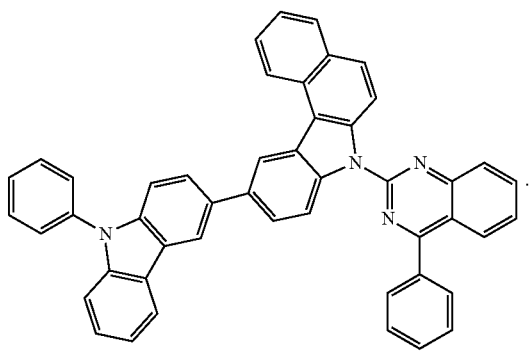

Phosphorescent Dopant

The phosphorescent dopant may include at least one transition metal as a central metal (e.g., a central metal atom).

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In an embodiment, the phosphorescent dopant may include an organometallic compound represented by Formula 401:

Formula 401

$M(L_{401})_{xc1}(L_{402})_{xc2}$

Formula 402

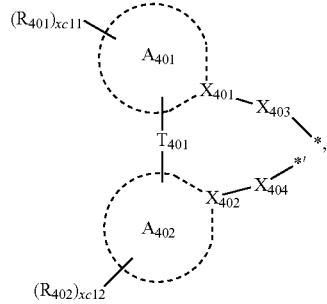

wherein, in Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein, when xc1 is two or more, two or more of $L_{401}$(s) may be identical to or different from each other, $L_{402}$ may be an organic ligand, and xc2 may be 0, 1, 2, 3, or 4, wherein, when xc2 is 2 or more, two or more of $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(=O)—*', *—N($Q_{411}$)—*'*—C($Q_{411}$)($Q_{412}$)-*', *—C($Q_{411}$)=C($Q_{412}$)-*', *—C($Q_{411}$)=*', or *=C=*', $X_{403}$ and $X_{404}$ may each independently be a chemical bond (for example, a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are each the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ are each the same as described in connection with $Q_1$, xc11 and xc12 may each independently be an integer from 0 to 10, and

* and *' in Formula 402 each indicate a binding site to M in Formula 401.

In an embodiment, in Formula 402, i) $X_{401}$ may be nitrogen, and $X_{402}$ may be carbon, or ii) each of $X_{401}$ and $X_{402}$ may be nitrogen.

In an embodiment, when xc1 in Formula 401 is 2 or more, two $A_{401}$(s) in two or more of $L_{401}$(s) may be optionally linked to each other via $T_{402}$, which is a linking group, and/or two $A_{402}$(s) in two or more of $L_{401}$(s) may optionally be linked to each other via $T_{403}$, which is a linking group (see Compounds PD1 to PD4 and PD7). $T_{402}$ and $T_{403}$ are each the same as described in connection with $T_{401}$.

$L_{402}$ in Formula 401 may be an organic ligand. In an embodiment, $L_{402}$ may include a halogen group, a diketone group (for example, an acetylacetonate group), a carboxylic acid group (for example, a picolinate group), —C(=O), an isonitrile group, a —CN group, a phosphorus group (for example, a phosphine group, a phosphite group, etc.), or any combination thereof.

The phosphorescent dopant may include, for example, one of Compounds PD1 to PD25, or any combination thereof:

PD1

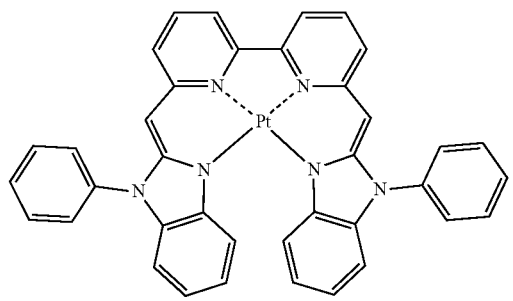

PD2

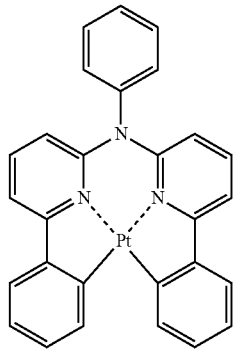

PD3

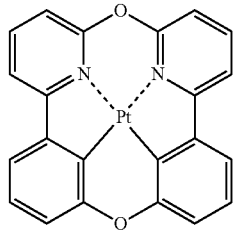

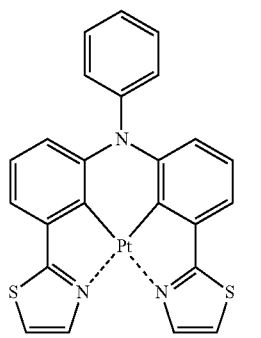
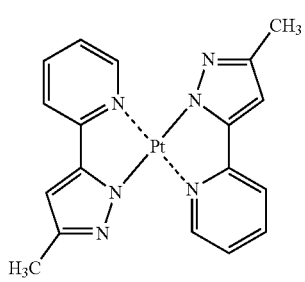
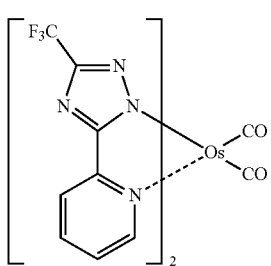
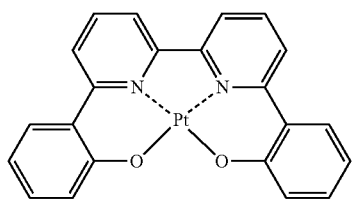
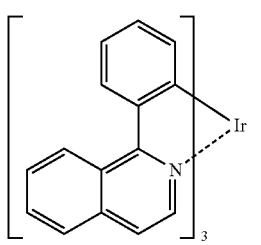
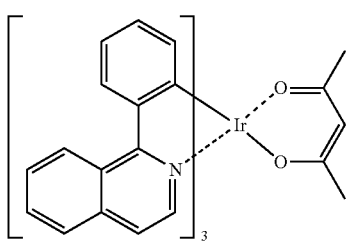
PD4
PD5
PD6
PD7
PD8
PD9
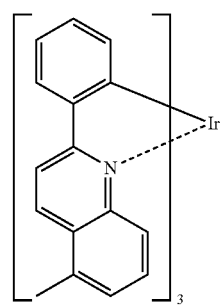
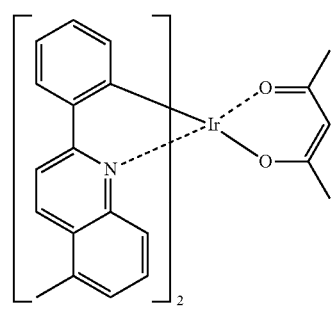
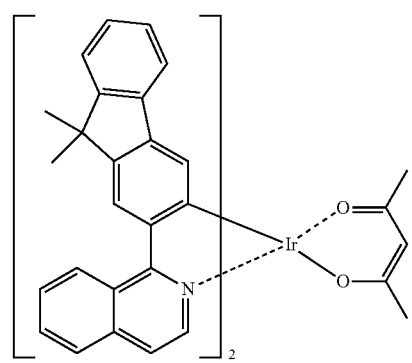
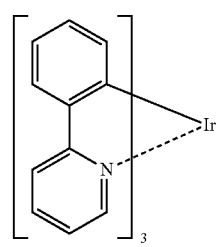
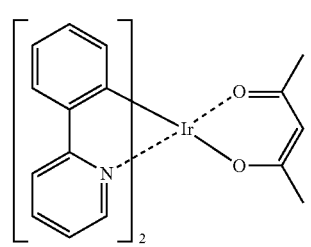
PD10
PD11
PD12
PD13
PD14

-continued
PD15 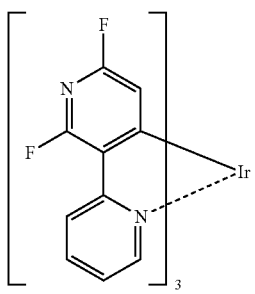
PD16 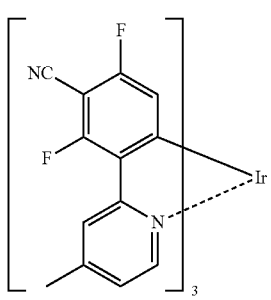
PD17 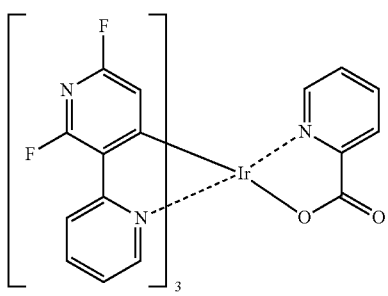
PD18 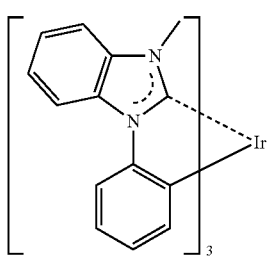
PD19 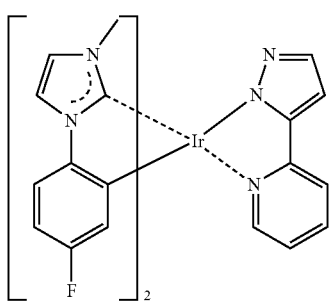
-continued
PD20 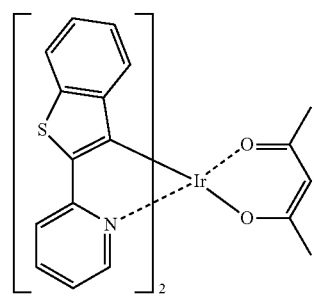
PD21 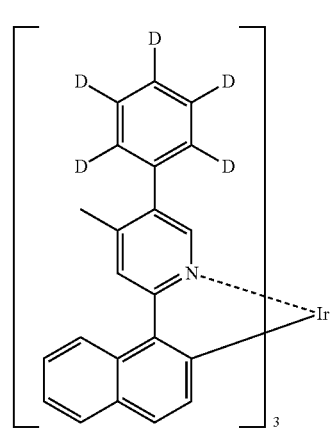
PD22 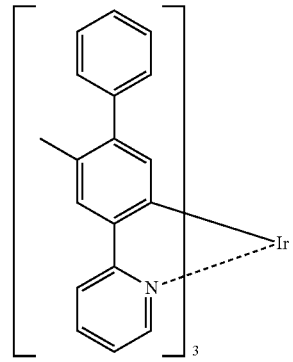
PD23 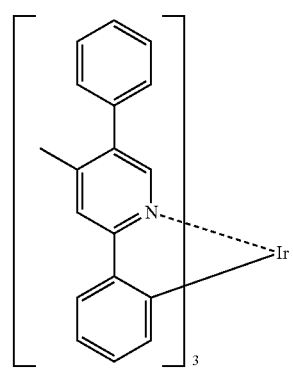

PD24

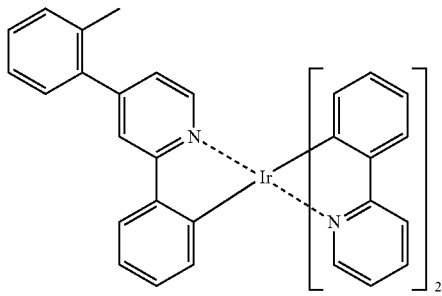

PD25

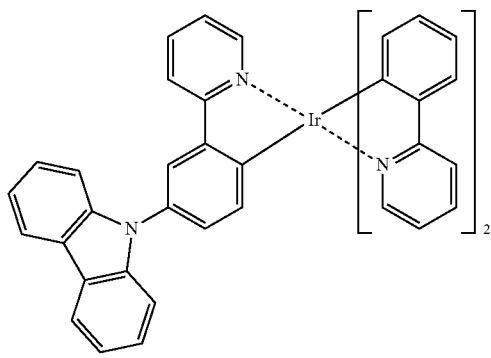

Fluorescent Dopant

The fluorescent dopant may include an amine group-containing compound, a styryl group-containing compound, or any combination thereof.

In an embodiment, the fluorescent dopant may include a compound represented by Formula 501:

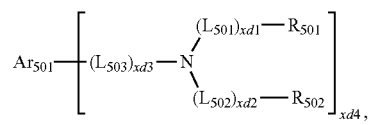

Formula 501 wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, $Ar_{501}$ in Formula 501 may be a condensed cyclic group (for example, an anthracene group, a chrysene group, and/or a pyrene group) in which three or more monocyclic groups are condensed together.

In an embodiment, xd4 in Formula 501 may be 2.

In an embodiment, the fluorescent dopant may include one of Compounds FD1 to FD37, DPVBi, DPAVBi, or any combination thereof:

FD1

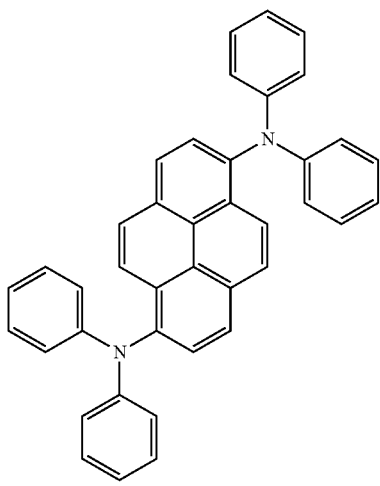

FD2

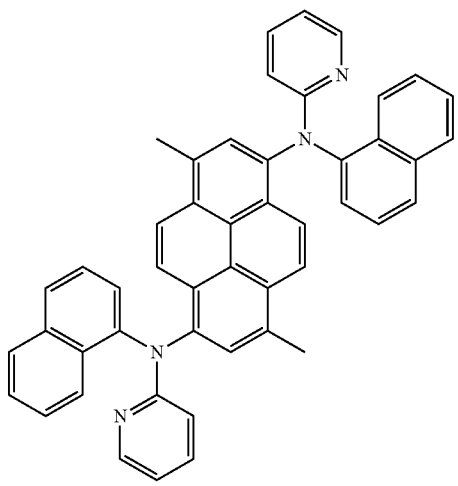

-continued
FD3
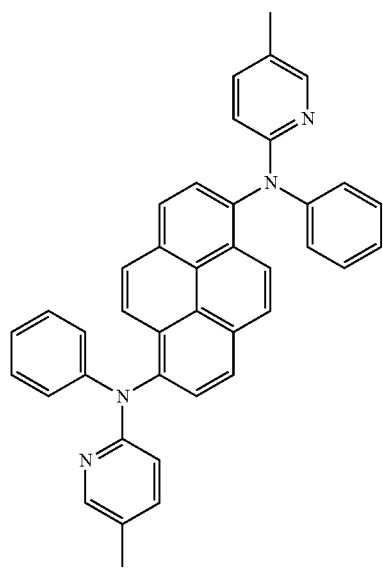
FD4
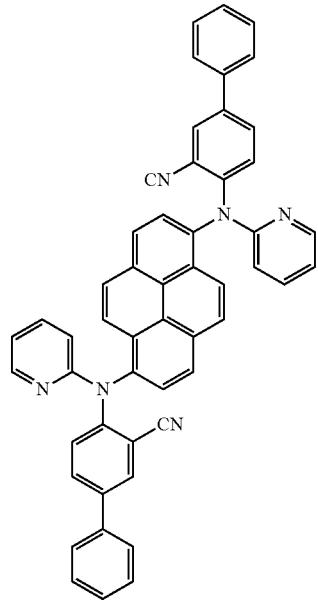
FD5
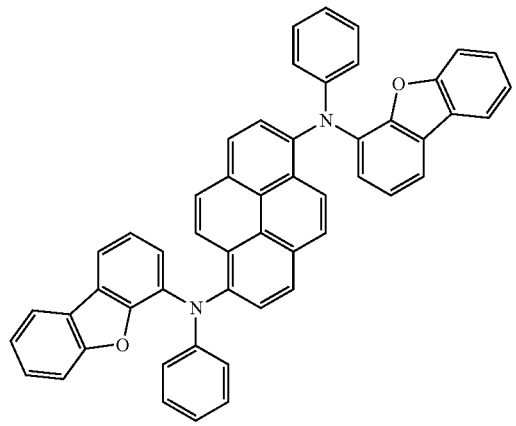
FD6
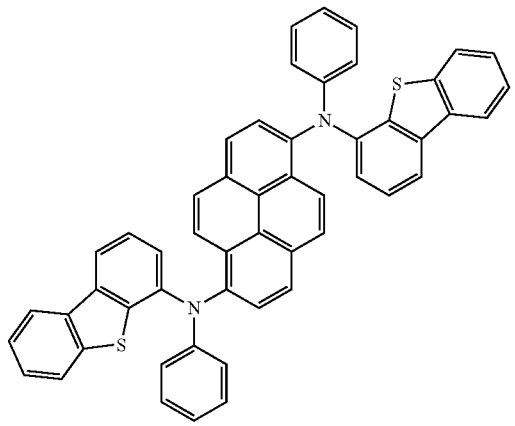
FD7
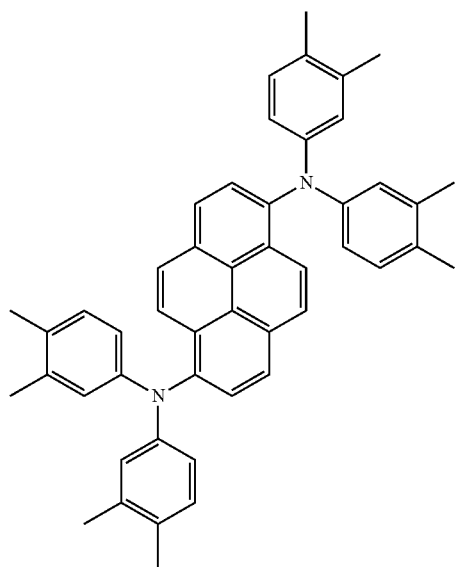
FD8
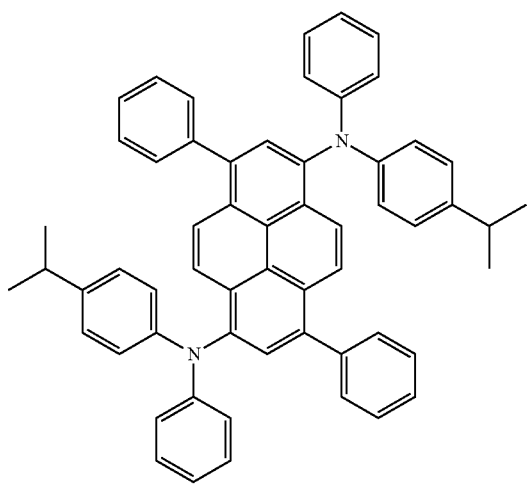

-continued
FD9
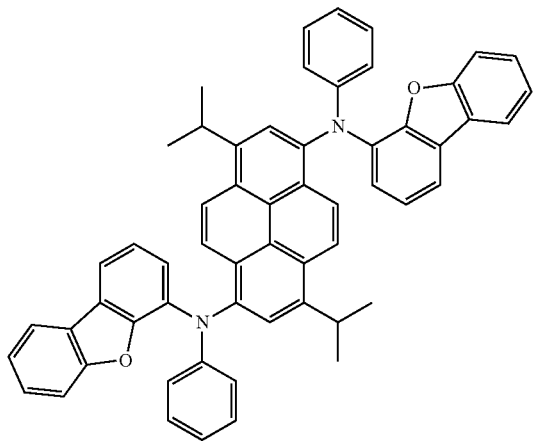
FD10
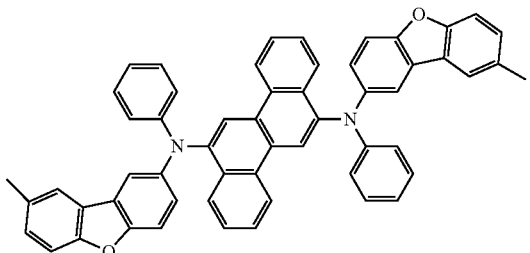
FD11
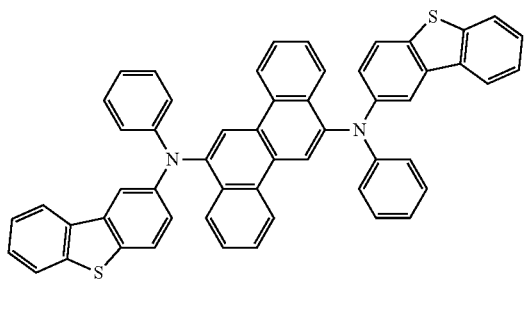
FD12
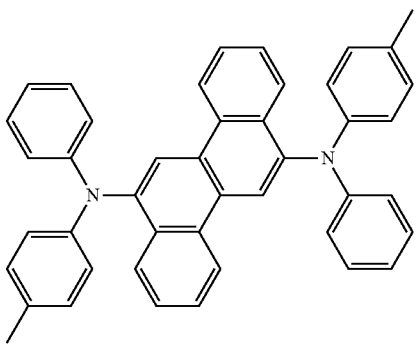
FD13
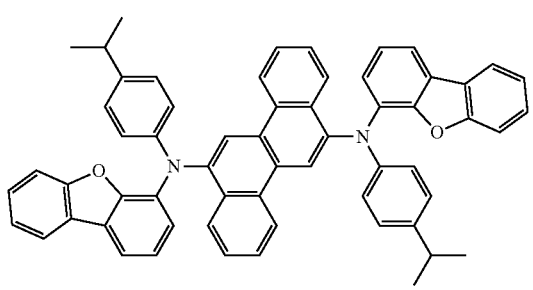
FD14
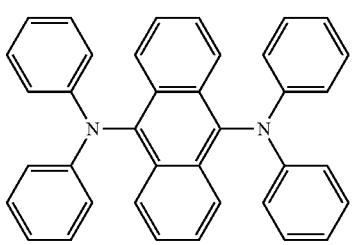
FD15
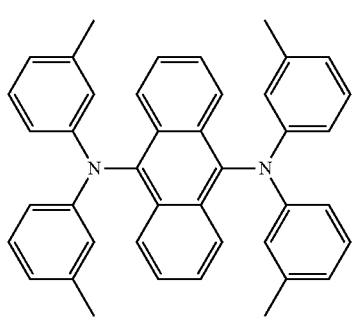
FD16
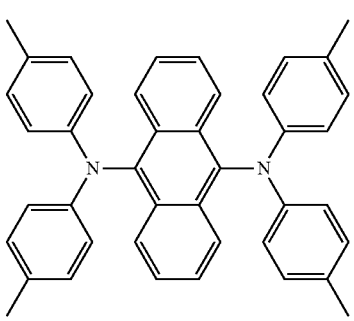

-continued
FD17
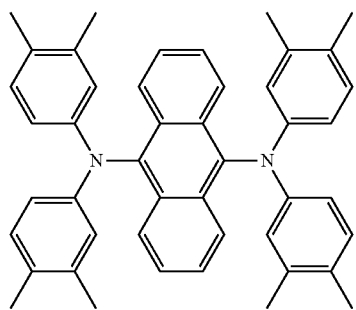
FD18
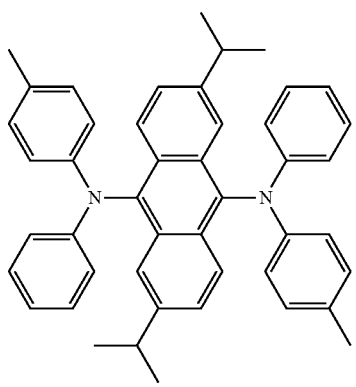
FD19
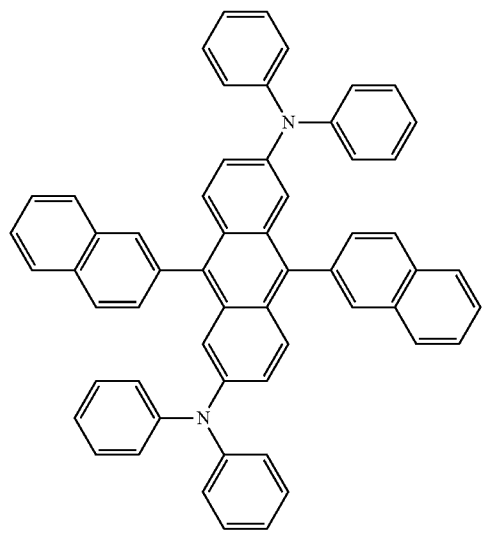
FD20
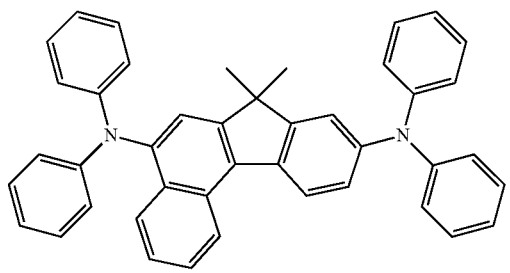
FD21
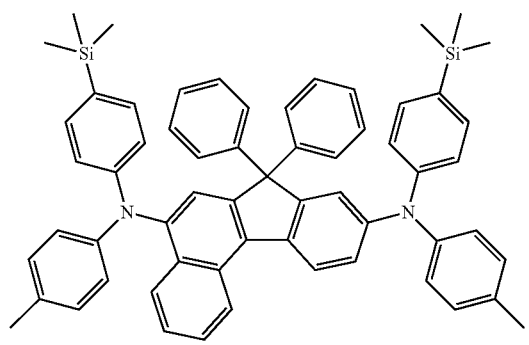
FD22
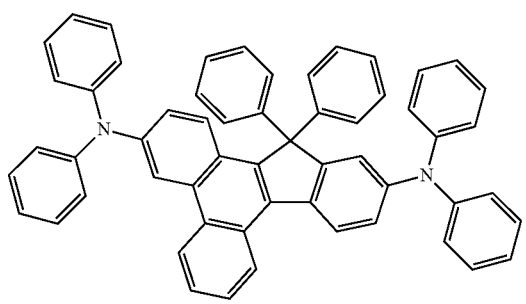
FD23
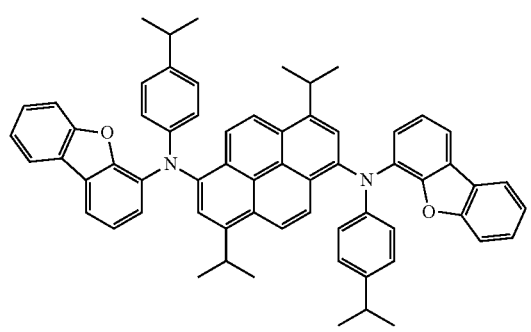
FD24
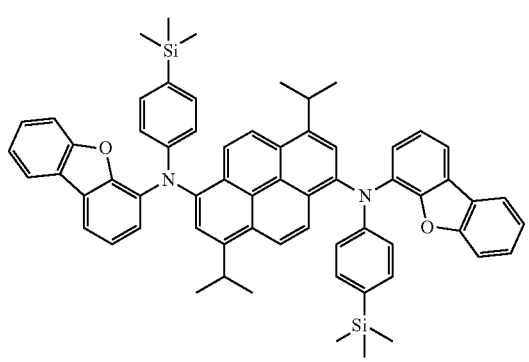

-continued
FD25
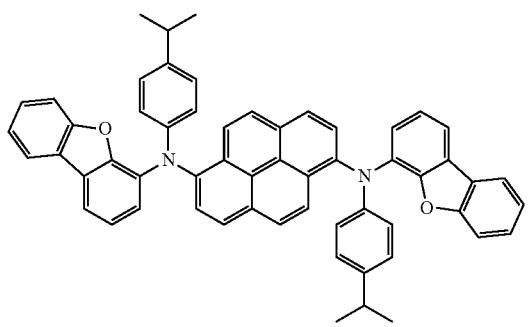
FD26
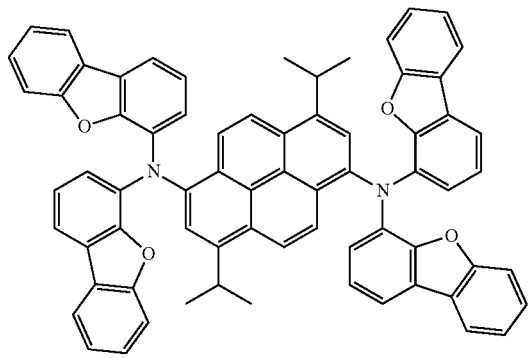
FD27
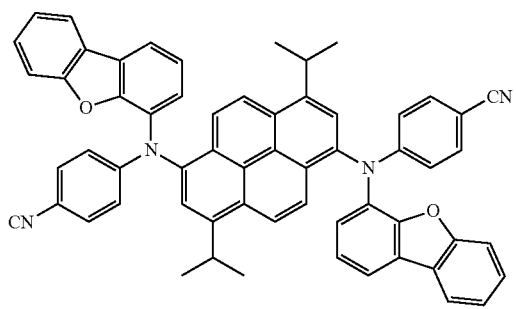
FD28
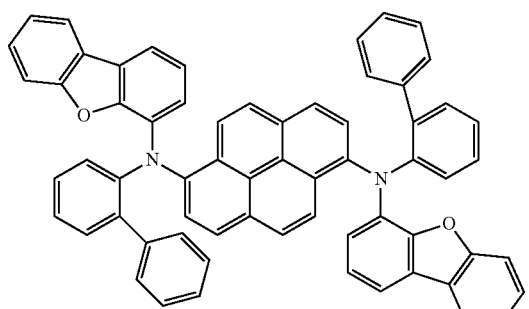
FD29
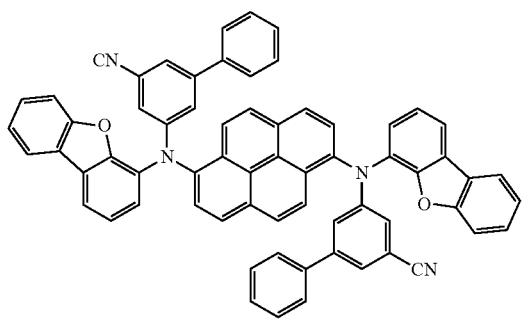
FD30
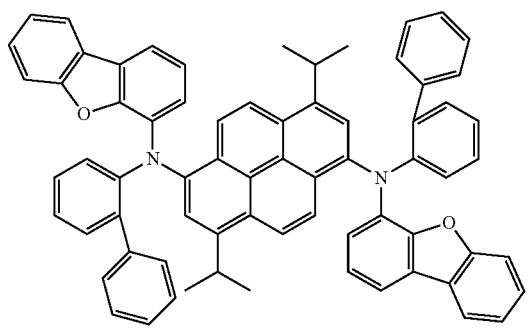
FD31
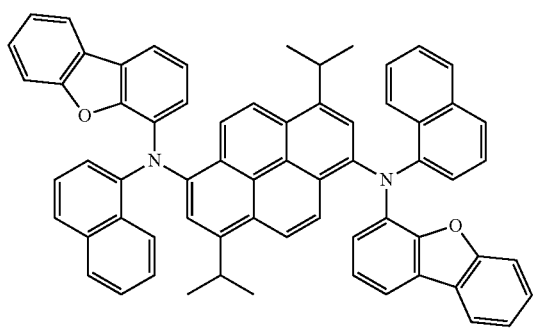
FD32
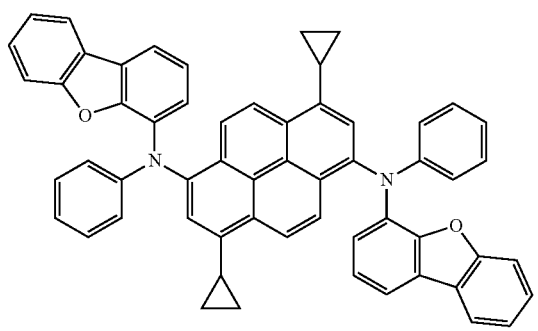

-continued
FD33
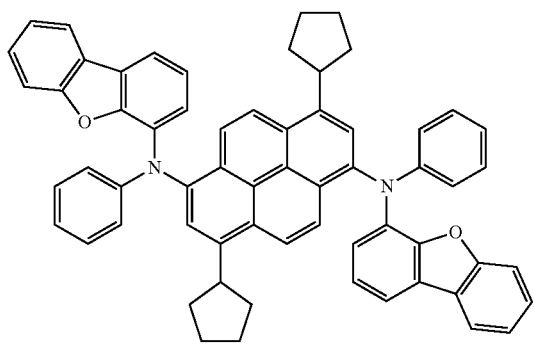
FD34
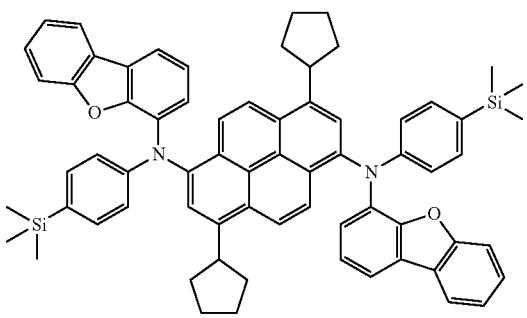
FD35
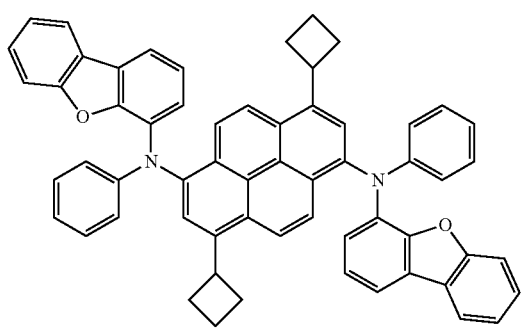
FD36
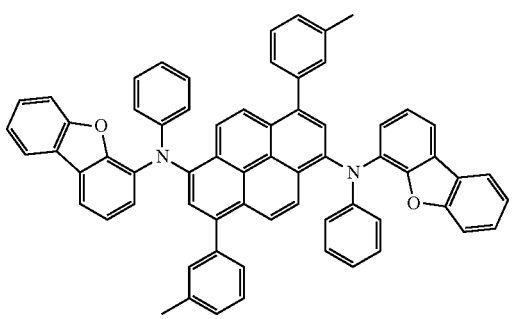
FD37
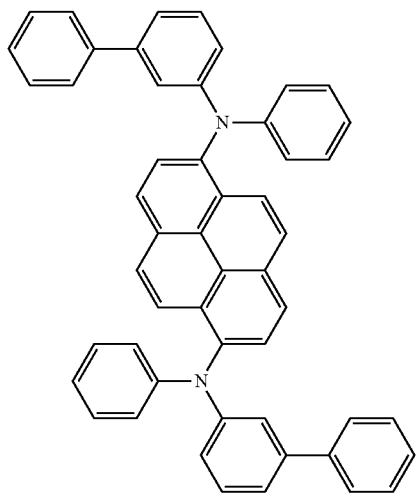
DPVBi
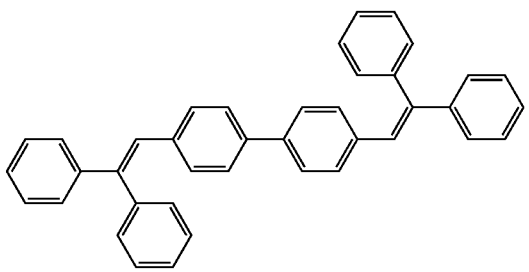
DPAVBi
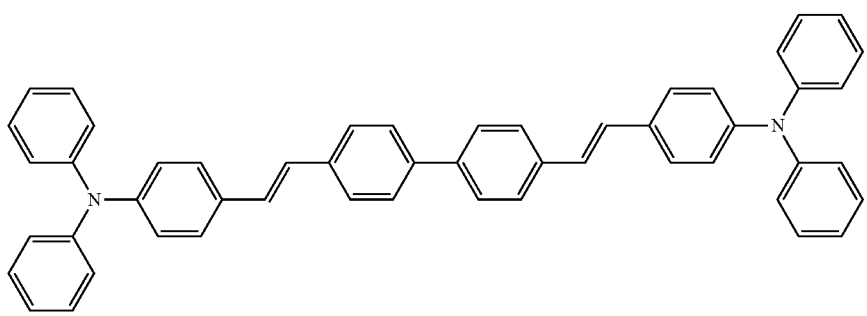

Delayed Fluorescence Material

The emission layer may include a delayed fluorescence material.

In the present specification, the delayed fluorescence material may be selected from compounds capable of emitting delayed fluorescence based on a delayed fluorescence emission mechanism.

The delayed fluorescence material included in the emission layer may serve as a host or a dopant depending on the kind (e.g., type) of other materials included in the emission layer.

In an embodiment, the difference between the triplet energy level in electron volt (eV) of the delayed fluorescence material and the singlet energy level in electron volt (eV) of the delayed fluorescence material may be greater than or equal to about 0 eV and less than or equal to about 0.5 eV. When the difference between the triplet energy level (eV) of the delayed fluorescence material and the singlet energy level in electron volt (eV) of the delayed fluorescence material satisfies the above-described range, the up-conversion from the triplet state to the singlet state of the delayed fluorescence materials may effectively occur, and thus, the luminescence efficiency of the light-emitting device 10 may be improved.

In an embodiment, the delayed fluorescence material may include i) a material including at least one electron donor (for example, a π electron-rich $C_3$-$C_{60}$ cyclic group, such as a carbazole group) and at least one electron acceptor (for example, a sulfoxide group, a cyano group, and/or a π electron-deficient nitrogen-containing $C_1$-$C_{60}$ cyclic group), and/or ii) a material including a $C_8$-$C_{60}$ polycyclic group in which two or more cyclic groups are condensed while sharing boron (B).

Examples of the delayed fluorescence material may include at least one of the following Compounds DF1 to DF9:

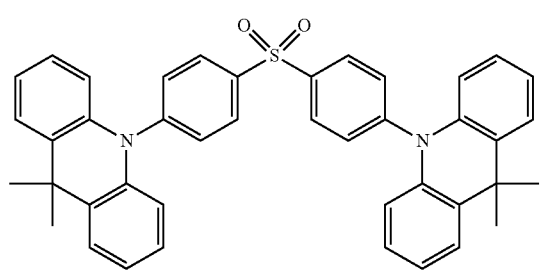

(DMAC-DPS) DF1

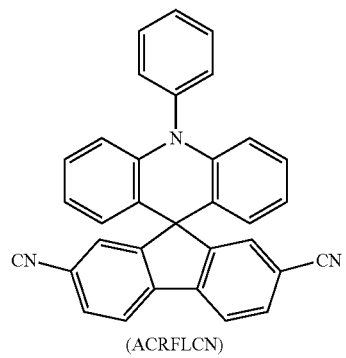

(ACRFLCN) DF2

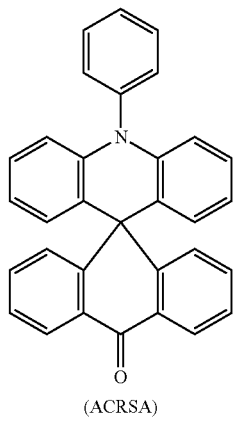

(ACRSA) DF3

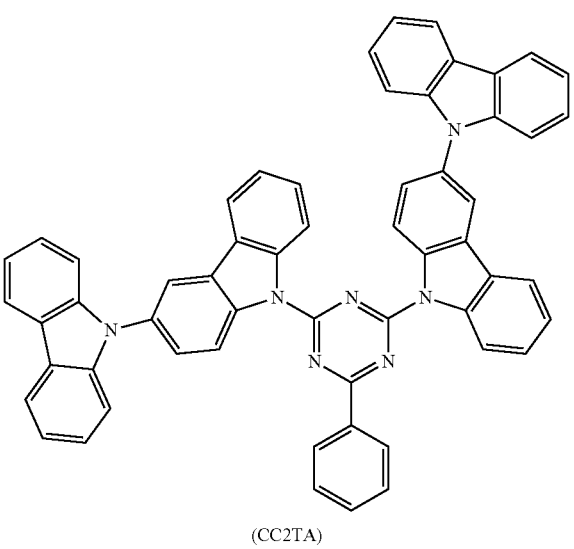

(CC2TA) DF4

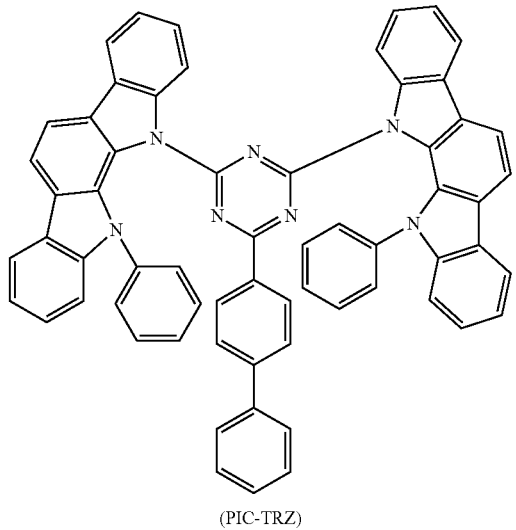

(PIC-TRZ) DF5

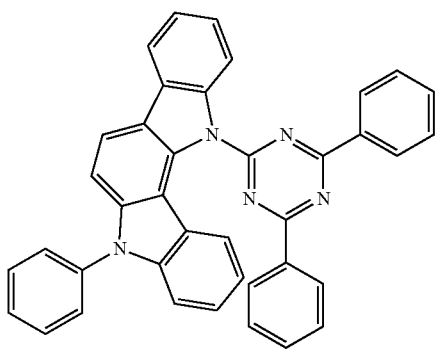

(PIC-TRZ2)

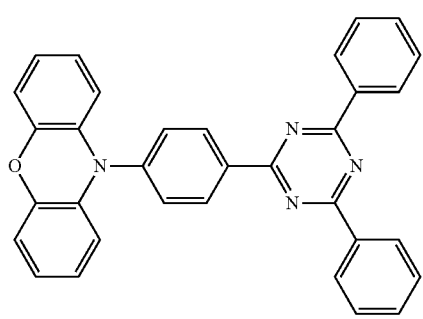

(PXZ-TRZ)

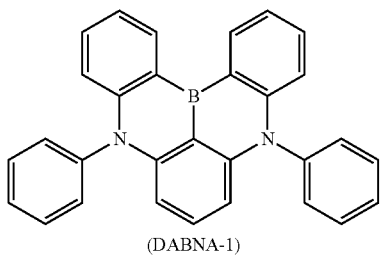

(DABNA-1)

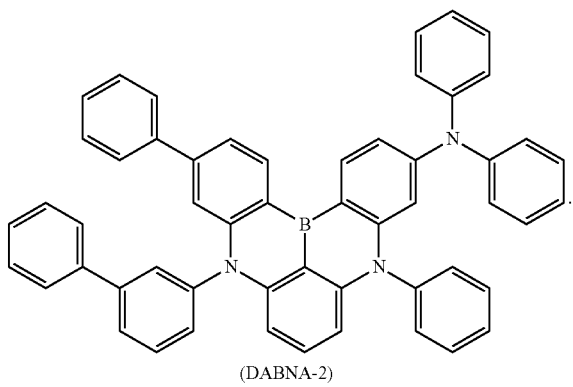

(DABNA-2)

Quantum Dot

The emission layer may include a quantum dot.

In the present specification, a quantum dot refers to a crystal of a semiconductor compound, and may include any material capable of emitting light of various suitable emission wavelengths according to the size of the crystal.

A diameter of the quantum dot may be, for example, in a range of about 1 nm to about 10 nm.

The quantum dot may be synthesized by a wet chemical process, a metal organic (e.g., organometallic) chemical vapor deposition process, a molecular beam epitaxy process, or any suitable process similar thereto.

According to the wet chemical process, a precursor material is mixed with an organic solvent to grow a quantum dot crystal particle. When the crystal grows, the organic solvent naturally acts as a dispersant coordinated on the surface of the quantum dot crystal and controls the growth of the crystal so that the growth of quantum dot particles can be controlled through a process which is more easily performed than vapor deposition methods, such as metal organic chemical vapor deposition (MOCVD) and/or molecular beam epitaxy (MBE), and which requires low costs.

The quantum dot may include: a Group II-VI semiconductor compound; a Group III-V semiconductor compound; a Group III-VI semiconductor compound; a Group I-III-VI semiconductor compound; a Group IV-VI semiconductor compound; a Group IV element or compound; or any combination thereof.

Examples of the Group II-VI semiconductor compound may include: a binary compound, such as CdSe, CdTe, ZnS, ZnSe, ZnTe, ZnO, HgS, HgSe, HgTe, MgSe, and/or MgS; a ternary compound, such as CdSeS, CdSeTe, CdالسTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound, such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Examples of the Group III-V semiconductor compound may include: a binary compound, such as GaN, GaP, GaAs, GaSb, AlN, AlP, AlAs, AlSb, InN, InP, InAs, InSb, and/or the like; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, InPSb, and/or the like; a quaternary compound, such as GaAlNP, GaAlNAs, GaAlNSb, GaAlPAs, GaAlPSb, GaInNP, GaIn-NAs, GaInNSb, GaInPAs, GaInPSb, InAlNP, InAlNAs, InAlNSb, InAlPAs, InAlPSb, and/or the like; or any combination thereof. In an embodiment, the Group III-V semiconductor compound may further include Group II elements. Examples of the Group III-V semiconductor compound further including the Group II elements may include InZnP, InGaZnP, InAlZnP, and the like.

Examples of the Group III-VI semiconductor compound may include: a binary compound, such as GaS, GaSe, $Ga_2Se_3$, GaTe, InS, InSe, $In_2S_3$, $In_2Se_3$, InTe, and/or the like; a ternary compound, such as $InGaS_3$, $InGaSe_3$, and/or the like; or any combination thereof.

Examples of the Group I-III-VI semiconductor compound may include: a ternary compound, such as AgInS, $AgInS_2$, CuInS, $CuInS_2$, $CuGaO_2$, $AgGaO_2$, and/or $AgAlO_2$; or any combination thereof.

Examples of the Group IV-VI semiconductor compound may include: a binary compound, such as SnS, SnSe, SnTe, PbS, PbSe, PbTe, and/or the like; a ternary compound, such as SnSeS, SnSeTe, SnSTe, PbSeS, PbSeTe, PbSTe, SnPbS, SnPbSe, SnPbTe, and/or the like; a quaternary compound, such as SnPbSSe, SnPbSeTe, SnPbSTe, and/or the like; or any combination thereof.

The Group IV element or compound may include: a single element, such as Si and/or Ge; a binary compound, such as SiC and/or SiGe; or any combination thereof.

Each element included in a multi-element compound such as the binary compound, the ternary compound and/or the quaternary compound, may exist (e.g., may be present) in a particle with a uniform concentration or non-uniform concentration.

In an embodiment, the quantum dot may have a single structure or a dual core-shell structure. In the case of the quantum dot having a single structure, the concentration of each element included in the corresponding quantum dot is uniform. In an embodiment, the material contained in the core and the material contained in the shell may be different from each other.

The shell of the quantum dot may act (e.g., serve) as a protective layer to prevent or reduce chemical degeneration of the core to maintain semiconductor characteristics and/or as a charging layer to impart electrophoretic characteristics to the quantum dot. The shell may be a single layer or a multi-layer. The element presented in the interface between the core and the shell of the quantum dot may have a concentration gradient that decreases toward the center of the quantum dot.

Examples of the shell of the quantum dot may be a metal oxide, a metalloid oxide, a non-metal oxide, a semiconductor compound, and any combination thereof. Examples of the metal oxide, the metalloid oxide, or the non-metal oxide may include: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound, such as $MgAl_2O_4$, $CoFe_2O_4$, $NiFe_2O_4$, and/or $CoMn_2O_4$; or any combination thereof. Examples of the semiconductor compound may include, as described herein, a Group II-VI semiconductor compound, a Group III-V semiconductor compound, a Group III-VI semiconductor compound, a Group I-III-VI semiconductor compound, a Group IV-VI semiconductor compound, or any combination thereof. In addition, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be about 45 nm or less, for example, about 40 nm or less, for example, about 30 nm or less, and within these ranges, color purity or color reproducibility may be increased (e.g., improved). In addition, because the light emitted through the quantum dot is emitted in all directions, the wide viewing angle can be improved.

In addition, the quantum dot may be a spherical particle, a pyramidal particle, a multi-arm particle, a cubic nanoparticle, a nanotube, a nanowire, a nanofiber, or a nanoplate.

Because the energy band gap can be adjusted by controlling the size of the quantum dot, light having various suitable wavelength bands can be obtained from the quantum dot emission layer. Therefore, by utilizing quantum dots of different sizes, a light-emitting device that emits light of various suitable wavelengths may be implemented. In an embodiment, the size of the quantum dot may be selected to emit red, green and/or blue light. In addition, the size of the quantum dot may be configured to emit white light by combining light of various suitable colors.

Electron Transport Region in Interlayer 130

The electron transport region may have: i) a single-layered structure consisting of a single layer consisting of a single material, ii) a single-layered structure consisting of a single layer consisting of a plurality of different materials, or iii) a multi-layered structure including a plurality of layers including different materials.

The electron transport region may include a buffer layer, a hole blocking layer, an electron control layer, an electron transport layer, an electron injection layer, or any combination thereof.

In an embodiment, the electron transport region may have a structure including an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, in each structure, constituting layers are sequentially stacked from the emission layer in the respective stated order.

The electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601 below:

$$[Ar_{601}]_{xe11}\text{-}[(L_{601})_{xe1}\text{-}R_{601}]_{xe21} \qquad \text{Formula 601}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_6$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{601})(Q_{602})(Q_{603})$, $-C(=O)(Q_{601})$, $-S(=O)_2(Q_{601})$, or $-P(=O)(Q_{601})(Q_{602})$, $Q_{601}$ to $Q_{603}$ are each the same as described in connection with $Q_1$, xe21 may be 1, 2, 3, 4, or 5, and $Ar_{601}$, $L_{601}$, and/or $R_{601}$ may (e.g., may each) independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}(s)$ may be linked to each other via a single bond.

In an embodiment, $Ar_{601}$ in Formula 601 may be a substituted or unsubstituted anthracene group.

In an embodiment, the electron transport region may include a compound represented by Formula 601-1:

Formula 601-1

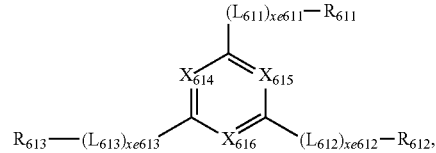

wherein, in Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ are each the same as described in connection with $L_{601}$, xe611 to xe613 are each the same as described in connection with xe1, $R_{611}$ to $R_{613}$ are each the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, xe1 and xe611 to xe613 in Formulae 601 and 601-1 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), Alq$_3$, BAlq, TAZ, NTAZ, or any combination thereof:

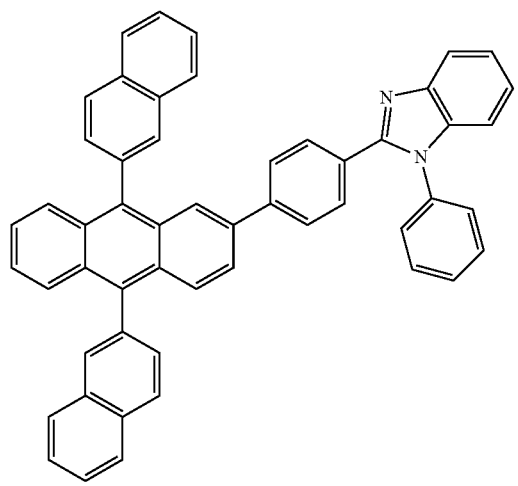

ET1

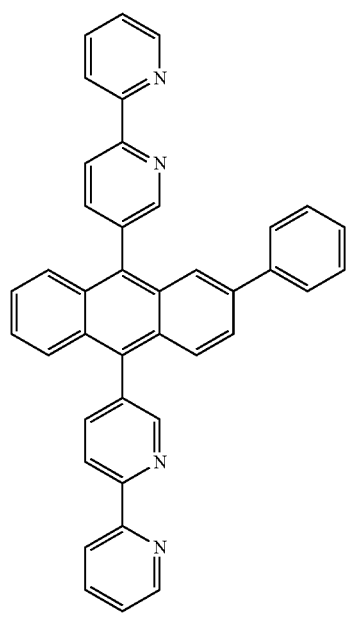

ET2

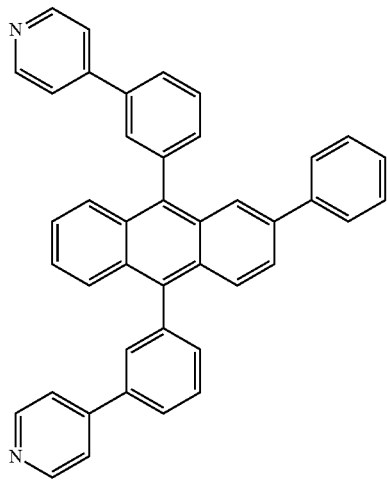

ET3

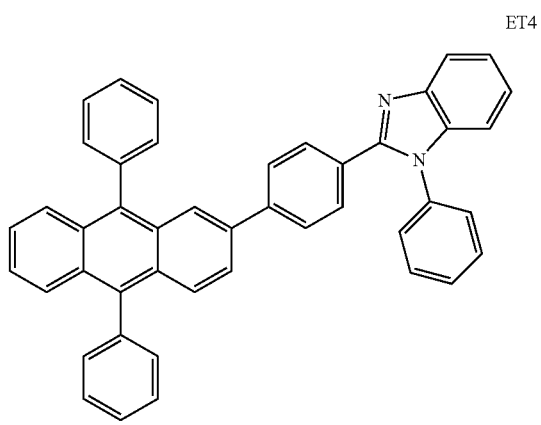

ET4

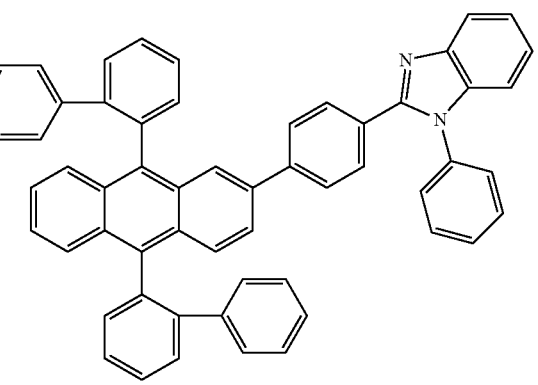

ET5

ET6
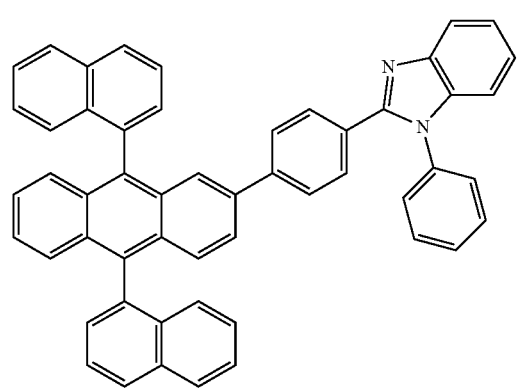
ET7
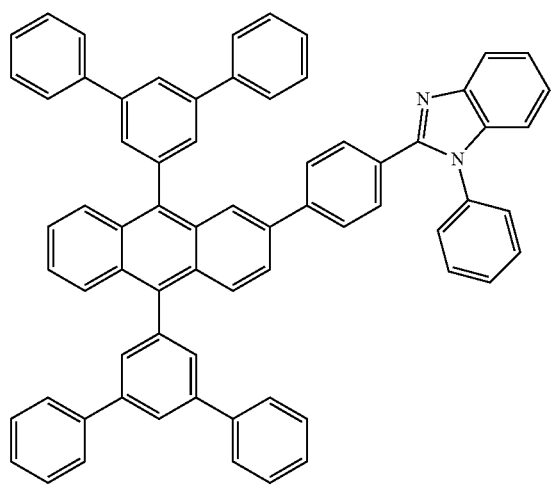
ET8
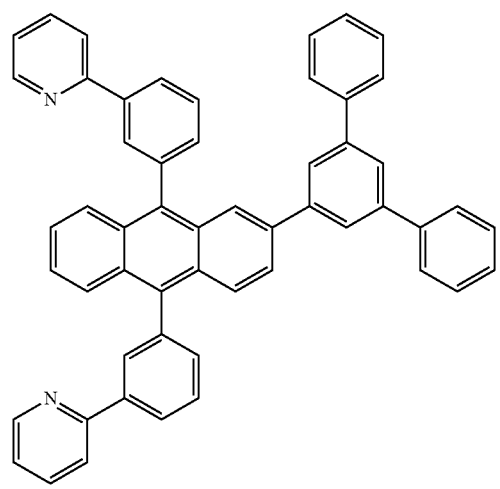
ET9
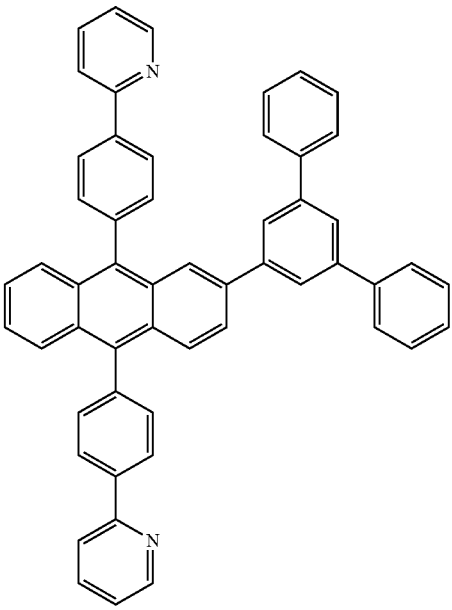
ET10
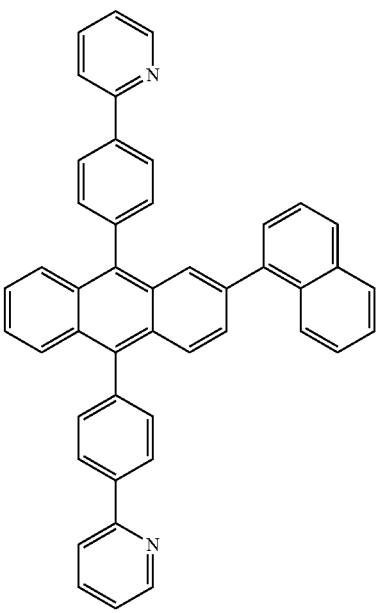

ET11
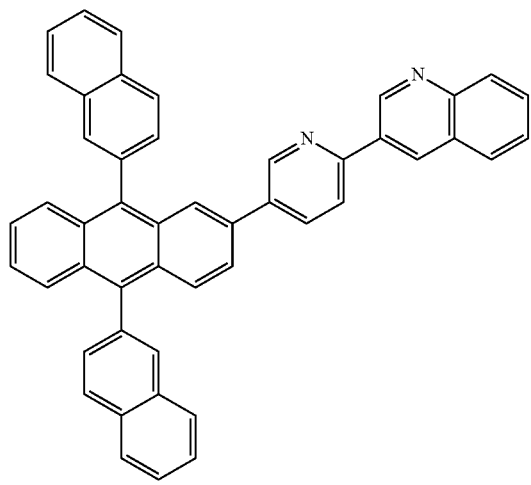
ET12
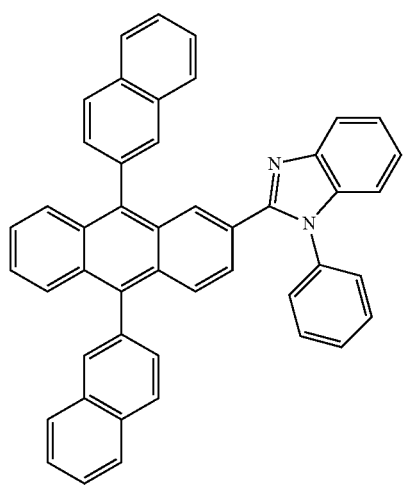
ET13
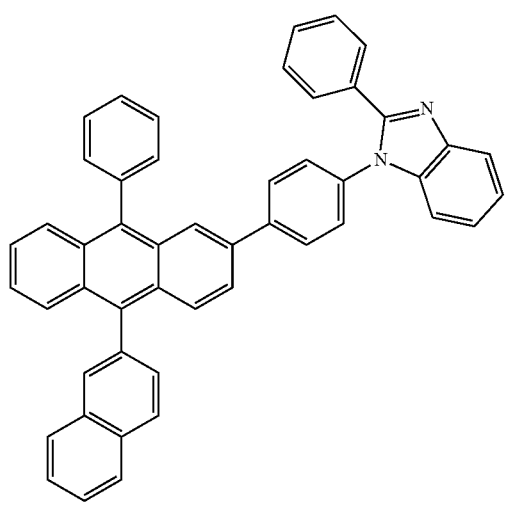
ET14
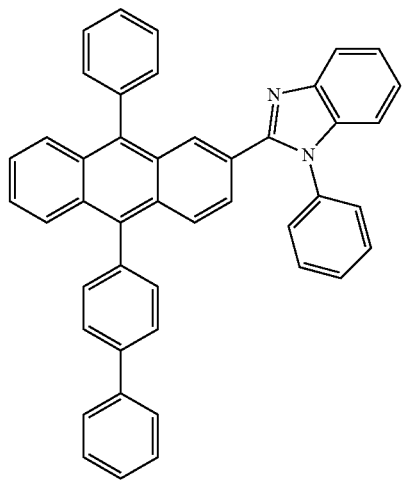
ET15
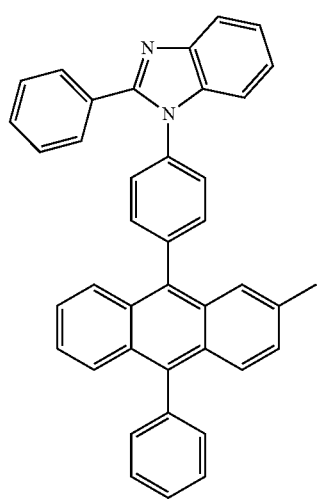
ET16
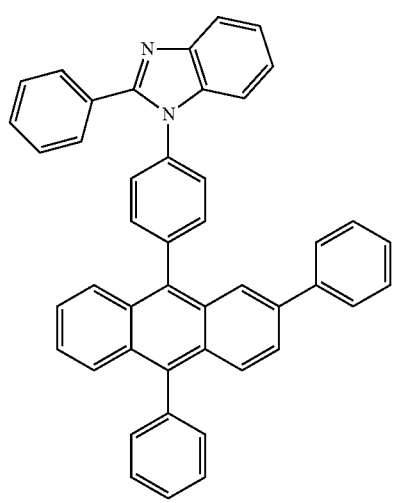

-continued
ET17
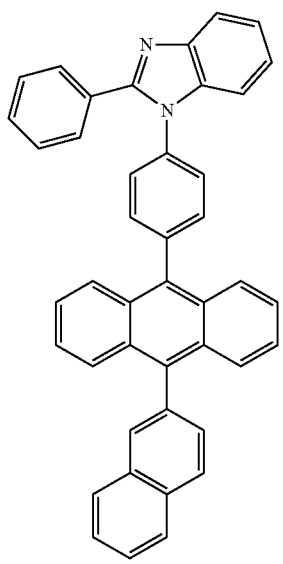
ET18
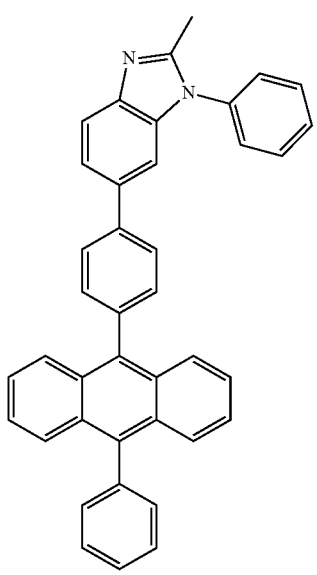
ET19
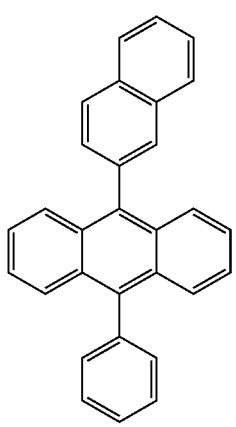
-continued
ET20
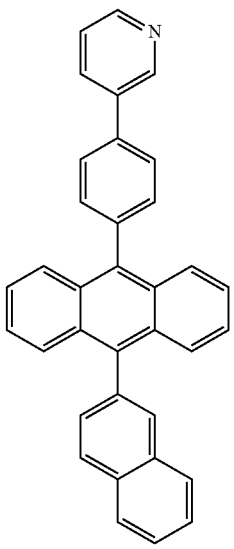
ET21
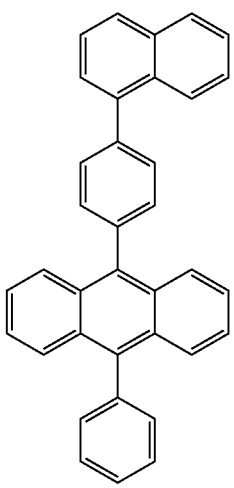
ET22
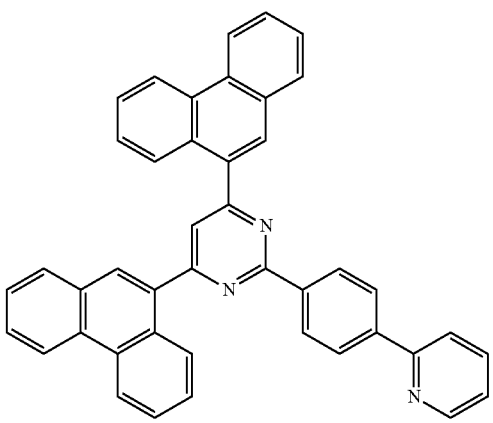

-continued
ET23
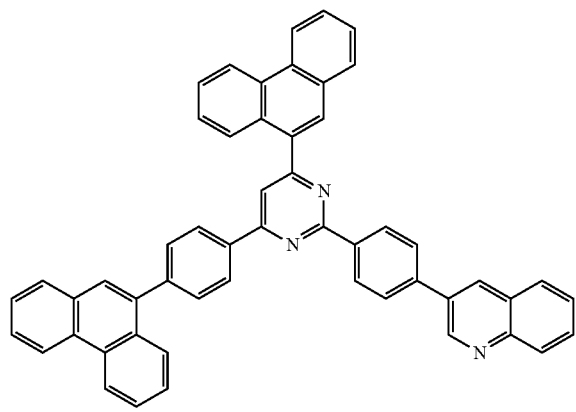
ET24
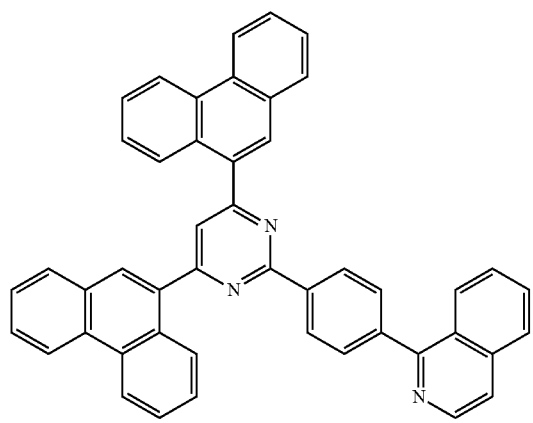
ET25
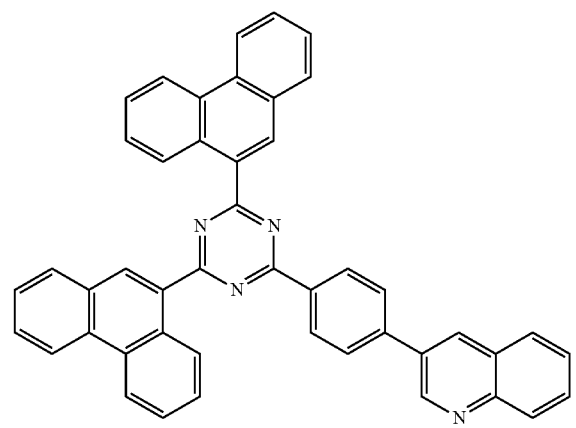
ET26
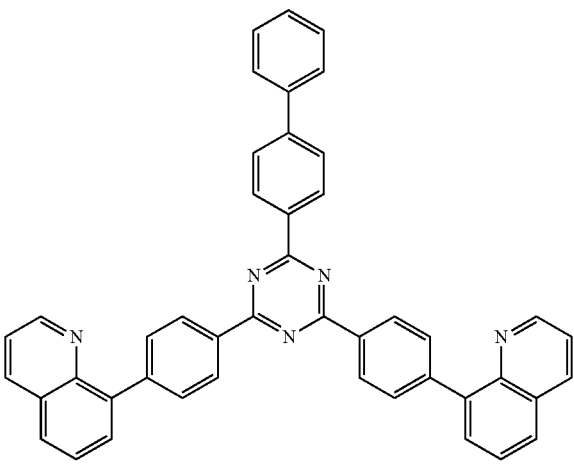
ET27
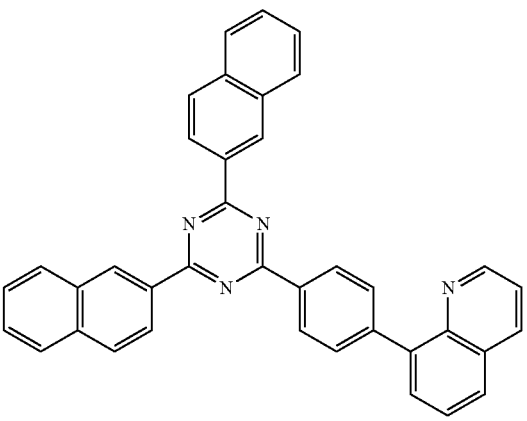
ET28
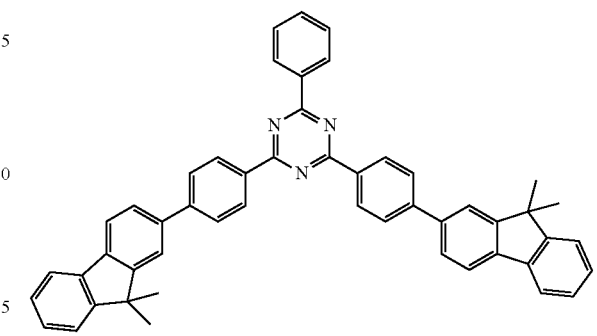

ET29
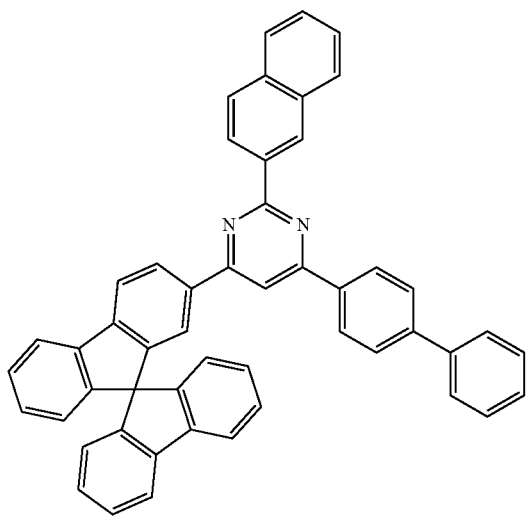
ET30
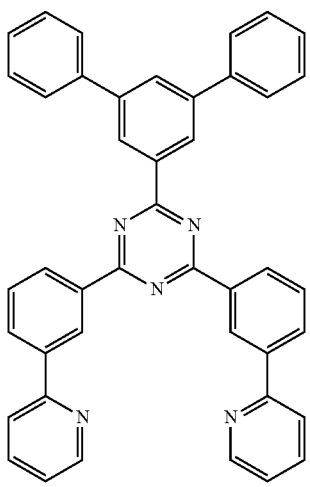
ET31
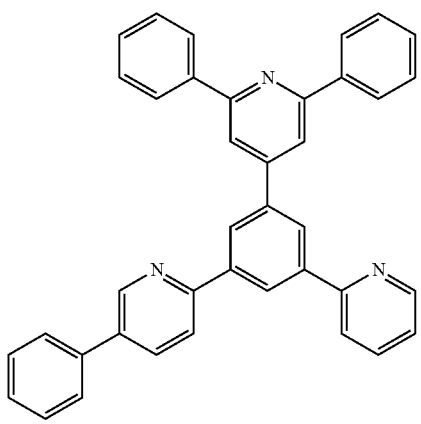
ET32
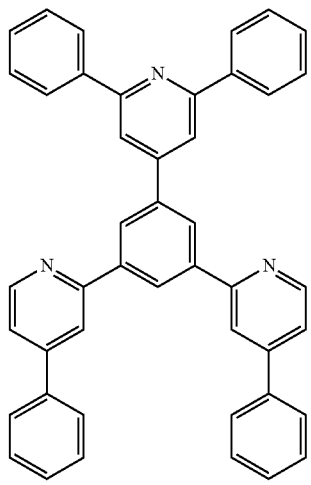
ET33
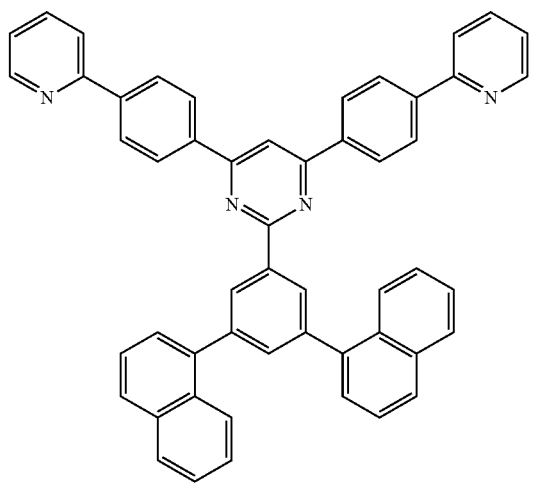
ET34
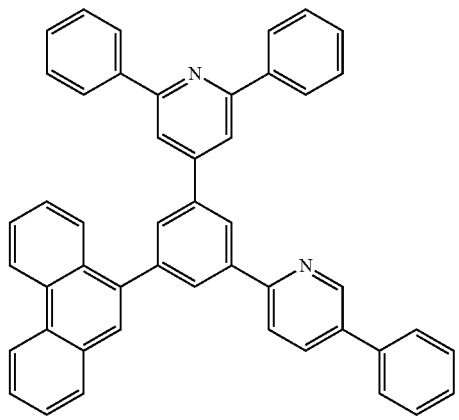

ET35
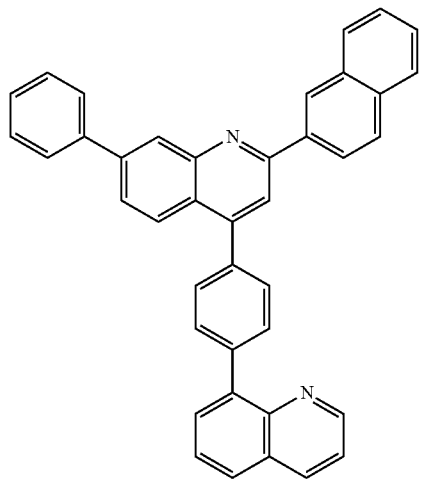
ET36
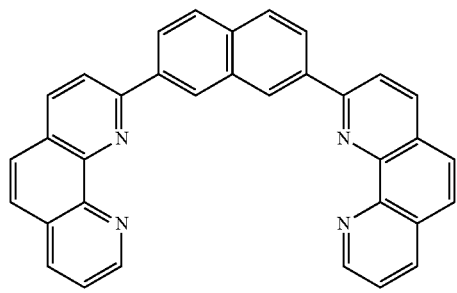
ET37
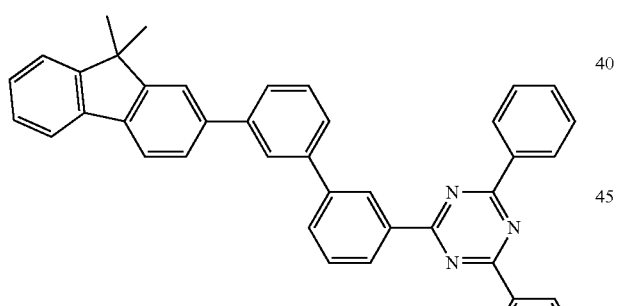
ET38
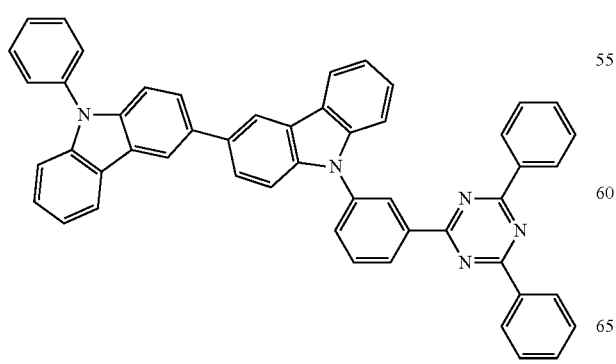
ET39
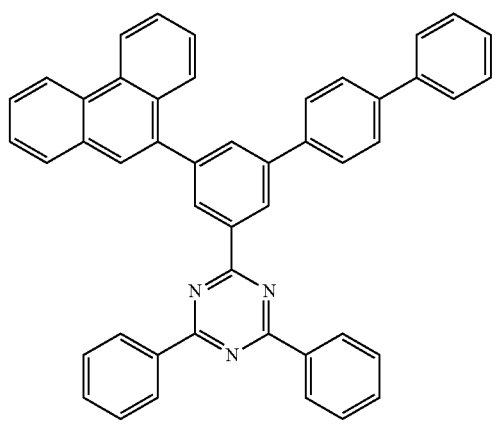
ET40
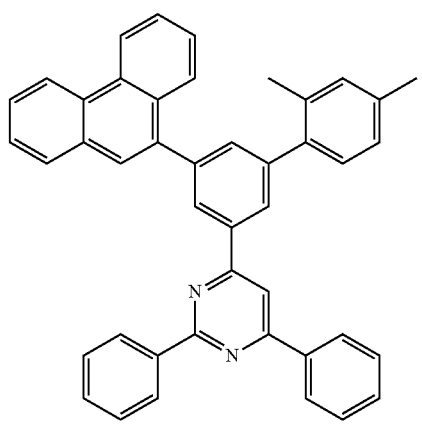
ET41
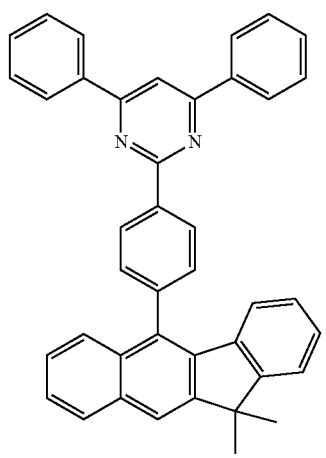

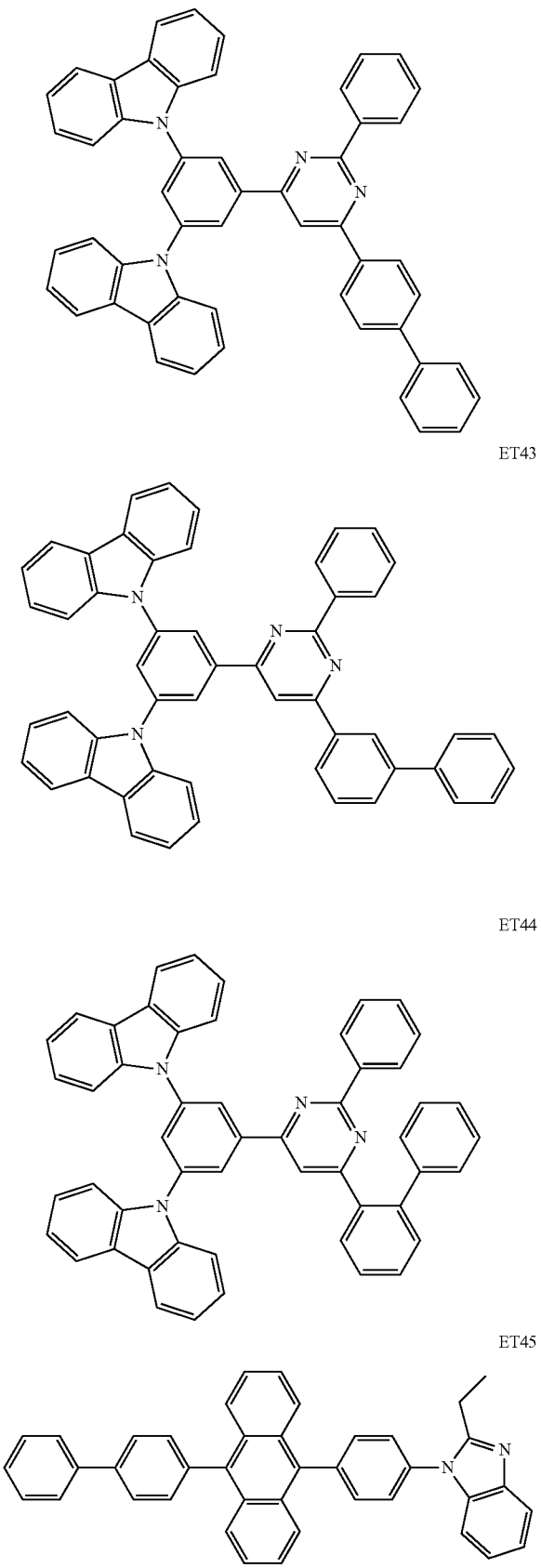

A thickness of the electron transport region may be from about 100 Å to about 5,000 Å, for example, from about 100 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be from about 20 Å to about 1,000 Å, for example, from about 30 Å to about 300 Å, and a thickness of the electron transport layer may be from about 100 Å to about 1,000 Å, for example, from about 150 Å to about 500 Å. When the thicknesses of the buffer layer, the hole blocking layer, the electron control layer, and/or the electron transport layer are within these ranges as described above, satisfactory electron-transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a Li ion, a Na ion, a K ion, a Rb ion, or a Cs ion, and a metal ion of the alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

In an embodiment, the metal-containing material may include a Li complex. The Li complex may include, for example, Compound ET-D1 (LiQ) or ET-D2:

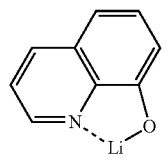

ET-D1

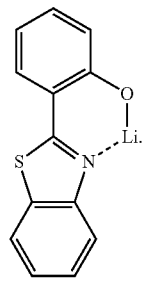

ET-D2

The electron transport region may include an electron injection layer that facilitates the injection of electrons from the second electrode 150. The electron injection layer may be in direct contact with the second electrode 150.

The electron injection layer may have: i) a single-layered structure consisting of a single layer consisting of a single material, ii) a single-layered structure consisting of a single layer consisting of a plurality of different materials, or iii) a multi-layered structure including a plurality of layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may include oxides, halides (for example, fluorides, chlorides, bromides, and/or iodides), and/or tellurides of the alkali metal, the alkaline earth metal, and the rare earth metal.

The alkali metal-containing compound may include alkali metal oxides (such as $Li_2O$, $Cs_2O$, and/or $K_2O$), alkali metal halides (such as LiF, NaF, CsF, KF, LiI, NaI, CsI, and/or KI), or any combination thereof. The alkaline earth metal-containing compound may include an alkaline earth metal oxides, such as BaO, SrO, CaO, $Ba_xSr_{1-x}O$ (x is a real number satisfying the condition of 0<x<1), $Ba_xCa_{1-x}O$ (x is a real number satisfying the condition of 0<x<1), and/or the like. The rare earth metal-containing compound may include $YbF_3$, $ScF_3$, $Sc_2O_3$, $Y_2O_3$, $Ce_2O_3$, $GdF_3$, $TbF_3$, $YbO_3$, $ScI_3$, $TbI_3$, or any combination thereof. In an embodiment, the rare earth metal-containing compound may include lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), a ligand bonded to the metal ion, for example, a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In an embodiment, the electron injection layer may further include an organic material (for example, a compound represented by Formula 601).

In an embodiment, the electron injection layer may include (e.g., consist of) i) an alkali metal-containing compound (for example, an alkali metal halide), or ii) a) an alkali metal-containing compound (for example, an alkali metal halide); and b) an alkali metal, an alkaline earth metal, a rare earth metal, or any combination thereof. In an embodiment, the electron injection layer may be a KI:Yb co-deposited layer, an RbI:Yb co-deposited layer, and/or the like.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth-metal complex, the rare earth metal complex, or any combination thereof may be homogeneously or non-homogeneously dispersed in a matrix including the organic material.

A thickness of the electron injection layer may be in a range of about 1 Å to about 100 Å, and, for example, about 3 Å to about 90 Å. When the thickness of the electron injection layer is within the ranges described above, satisfactory electron injection characteristics may be obtained without a substantial increase in driving voltage.

Second Electrode 150

The second electrode 150 may be located on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be utilized.

In an embodiment, the second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including two or more layers.

Capping Layer

A first capping layer may be located outside the first electrode 110 (e.g., on the side of the first electrode 110 facing oppositely away from the second electrode 150), and/or a second capping layer may be located outside the second electrode 150 (e.g., on the side of the second electrode 150 facing oppositely away from the first electrode 110). In one embodiment, the light-emitting device 10 may have a structure in which the first capping layer, the first electrode 110, the interlayer 130, and the second electrode 150 are sequentially stacked in this stated order, a structure in which the first electrode 110, the interlayer 130, the second electrode 150, and the second capping layer are sequentially stacked in this stated order, or a structure in which the first capping layer, the first electrode 110, the interlayer 130, the second electrode 150, and the second capping layer are sequentially stacked in this stated order.

Light generated in an emission layer of the interlayer 130 of the light-emitting device 10 may be directed or extracted toward the outside through the first electrode 110 (which may be a semi-transmissive electrode or a transmissive electrode) and the first capping layer (which may be a semi-transmissive layer or a transmissive layer), or light generated in an emission layer of the interlayer 130 of the light-emitting device 10 may be directed or extracted toward the outside through the second electrode 150 (which may be a semi-transmissive electrode or a transmissive electrode) and the second capping layer (which may be a semi-transmissive layer or a transmissive layer).

The first capping layer and the second capping layer may increase external emission efficiency according to the principle of constructive interference. Accordingly, the light extraction efficiency of the light-emitting device 10 may be increased, so that the emission efficiency of the light-emitting device 10 may be improved.

Each of the first capping layer and second capping layer may include a material having a refractive index (at 589 nm) of 1.6 or more.

The first capping layer and the second capping layer may each independently be an organic capping layer including an organic material, an inorganic capping layer including an inorganic material, or an organic-inorganic composite capping layer including an organic material and an inorganic material.

The first capping layer and/or the second capping layer may (e.g., may each) independently include a carbocyclic compound, a heterocyclic compound, an amine group-containing compound, a porphyrin derivative, a phthalocyanine derivative, a naphthalocyanine derivative, an alkali metal complex, an alkaline earth metal complex, or any combination thereof. The carbocyclic compound, the heterocyclic compound, and the amine group-containing compound may be optionally substituted with a substituent containing O, N, S, Se, Si, F, Cl, Br, I, or any combination thereof. In an embodiment, the first capping layer and/or the second capping layer may (e.g., may each) independently include an amine group-containing compound.

In an embodiment, the first capping layer and/or the second capping layer may (e.g., may each) independently include a compound represented by Formula 201, a compound represented by Formula 202, or any combination thereof.

In an embodiment, the first capping layer and/or the second capping layer may (e.g., may each) independently include one of Compounds HT28 to HT33, Compounds CP1 to CP6, β-NPB, or any combination thereof:

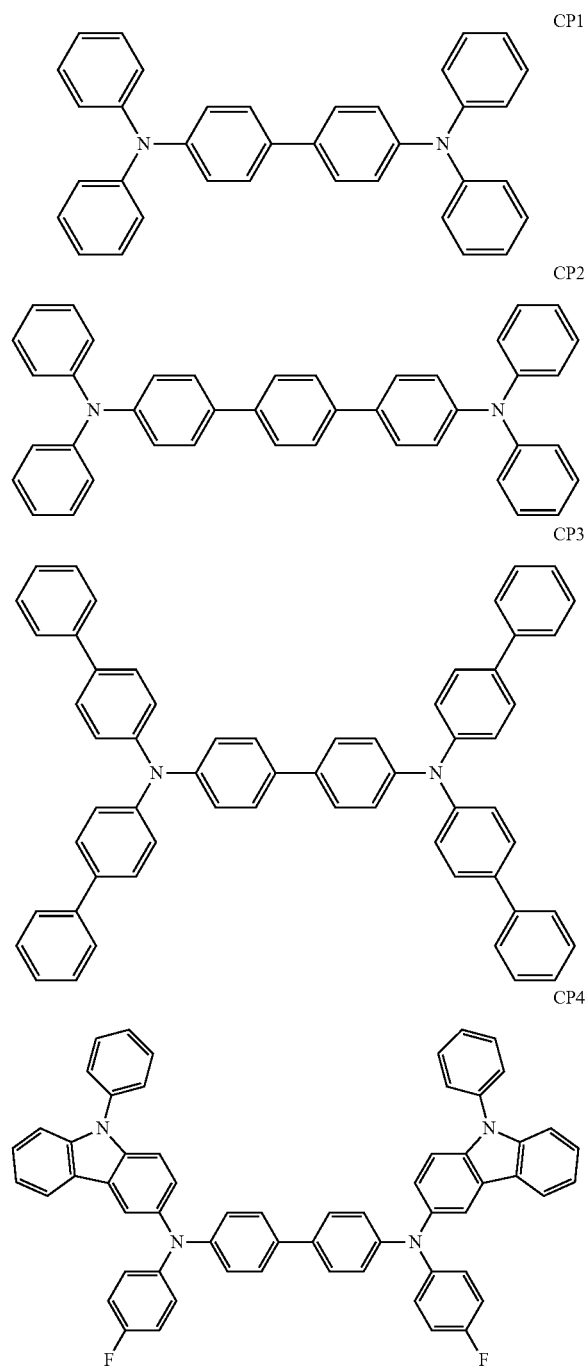

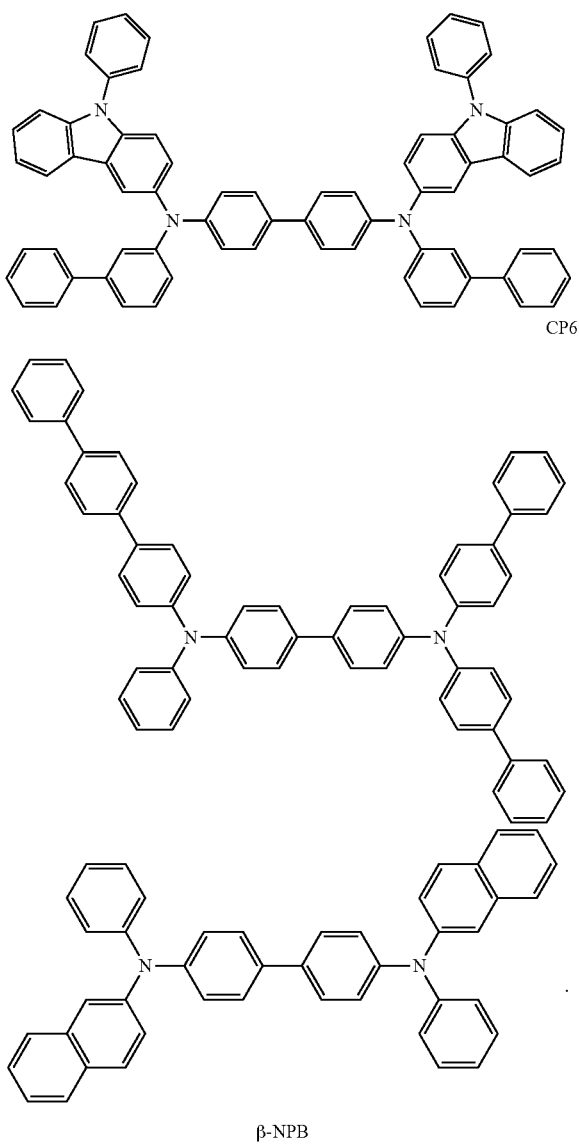

β-NPB

Film

At least one of the first to third compounds may be included in various suitable films (e.g., layers). Accordingly, according to another embodiment of the disclosure, a film including at least one of the first to third compounds may be provided. The film may be, for example, an optical member (or a light control means) (for example, a color filter, a color conversion member, a capping layer, a light extraction efficiency improving layer, a selective light absorption layer, a polarizing layer, a quantum dot-containing layer, etc.), a light-blocking member (for example, a light-reflecting layer, a light-absorbing layer, etc.), a protective layer (for example, an insulating layer, a dielectric layer, etc.), and/or the like.

Electronic Apparatus

The light-emitting device may be included in various suitable electronic apparatuses. In an embodiment, the electronic apparatus including the light-emitting device may be a light-emitting apparatus, an authentication apparatus, and/or the like.

The electronic apparatus (for example, a light-emitting apparatus) may further include, in addition to the light-emitting device, i) a color filter, ii) a color conversion layer, or iii) a color filter and a color conversion layer. The color filter and/or the color conversion layer may be located in at least one traveling direction of light emitted from the light-emitting device. In an embodiment, the light emitted from the light-emitting device may be blue light or white light. The light-emitting device may be the same as described above. In an embodiment, the color conversion layer may include quantum dots. The quantum dots may be the same as described herein.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the plurality of subpixel areas.

A pixel-defining film may be located between the subpixel areas to define each of the subpixel areas.

The color filter may include a plurality of color filter areas and may further include light-shielding patterns located between the plurality of color filter areas, and the color conversion layer may include a plurality of color conversion areas and may further include light-shielding patterns located between the plurality of color conversion areas.

The plurality of color filter areas (or the plurality of color conversion areas) may include a first area emitting a first color light, a second area emitting a second color light, and/or a third area emitting a third color light, and the first color light, the second color light, and/or the third color light may have different maximum emission wavelengths from one another. In an embodiment, the first color light may be red light, the second color light may be green light, and the third color light may be blue light. In an embodiment, the plurality of color filter areas (or the plurality of color conversion areas) may include quantum dots. In more detail, the first area may include a red quantum dot, the second area may include a green quantum dot, and the third area may not include a quantum dot. The quantum dot may be the same as described in the present specification. The first area, the second area, and/or the third area may each further include a scatterer.

In an embodiment, the light-emitting device may emit a first light, the first area may absorb the first light to emit a first first-color light, the second area may absorb the first light to emit a second first-color light, and the third area may absorb the first light to emit a third first-color light. In this regard, the first first-color light, the second first-color light, and the third first-color light may have different maximum emission wavelengths. In more detail, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an activation layer (e.g., an active layer), wherein the source electrode or the drain electrode may be electrically connected to the first electrode or the second electrode of the light-emitting device.

The thin-film transistor may further include a gate electrode, a gate insulating film, etc.

The activation layer may include crystalline silicon, amorphous silicon, an organic semiconductor, an oxide semiconductor, and/or the like.

The electronic apparatus may further include a sealing portion for sealing the light-emitting device. The sealing portion and/or the color conversion layer may be located between the color filter and the light-emitting device. The sealing portion allows light from the light-emitting device to be extracted to the outside, while concurrently (or simultaneously) preventing or substantially preventing ambient air and moisture from penetrating into the light-emitting device. The sealing portion may be a sealing substrate including a transparent glass substrate or a plastic substrate. The sealing portion may be a thin-film encapsulation layer including at least one layer of an organic layer and/or an inorganic layer. When the sealing portion is a thin film encapsulation layer, the electronic apparatus may be flexible.

Various suitable functional layers may be additionally located on the sealing portion, in addition to the color filter and/or the color conversion layer, according to the usage of the electronic apparatus. The functional layers may include a touch screen layer, a polarizing layer, and/or the like. The touch screen layer may be a pressure-sensitive touch screen layer, a capacitive touch screen layer, or an infrared touch screen layer. The authentication apparatus may be, for example, a biometric authentication apparatus that authenticates an individual by utilizing biometric information of a living body (for example, fingertips, pupils, etc.).

The authentication apparatus may further include, in addition to the light-emitting device, a biometric information collector.

The electronic apparatus may be applied to various suitable displays, light sources, lighting apparatuses, personal computers (for example, a mobile personal computer), mobile phones, digital cameras, electronic diaries (or organizers), electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, and/or endoscope displays), fish finders, various suitable measuring instruments, meters (for example, meters for a vehicle, an aircraft, and a vessel), projectors, and/or the like.

Figure 2:
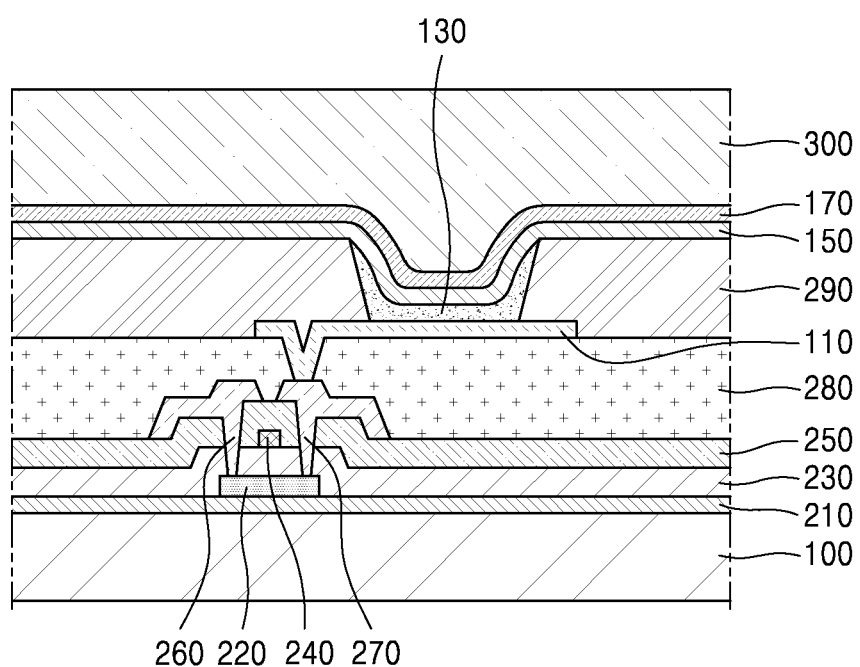
FIG. 2 is a cross-sectional view of a light-emitting apparatus according to an embodiment.
Figure 3:
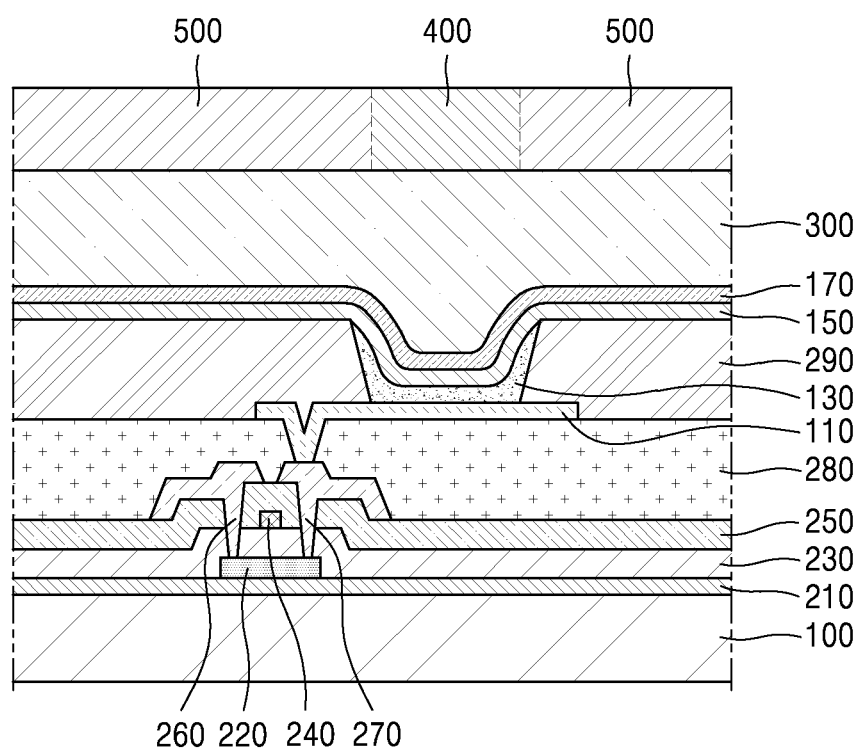
FIG. 3 is a cross-sectional view of a light-emitting apparatus according to an embodiment.
Figure 4:
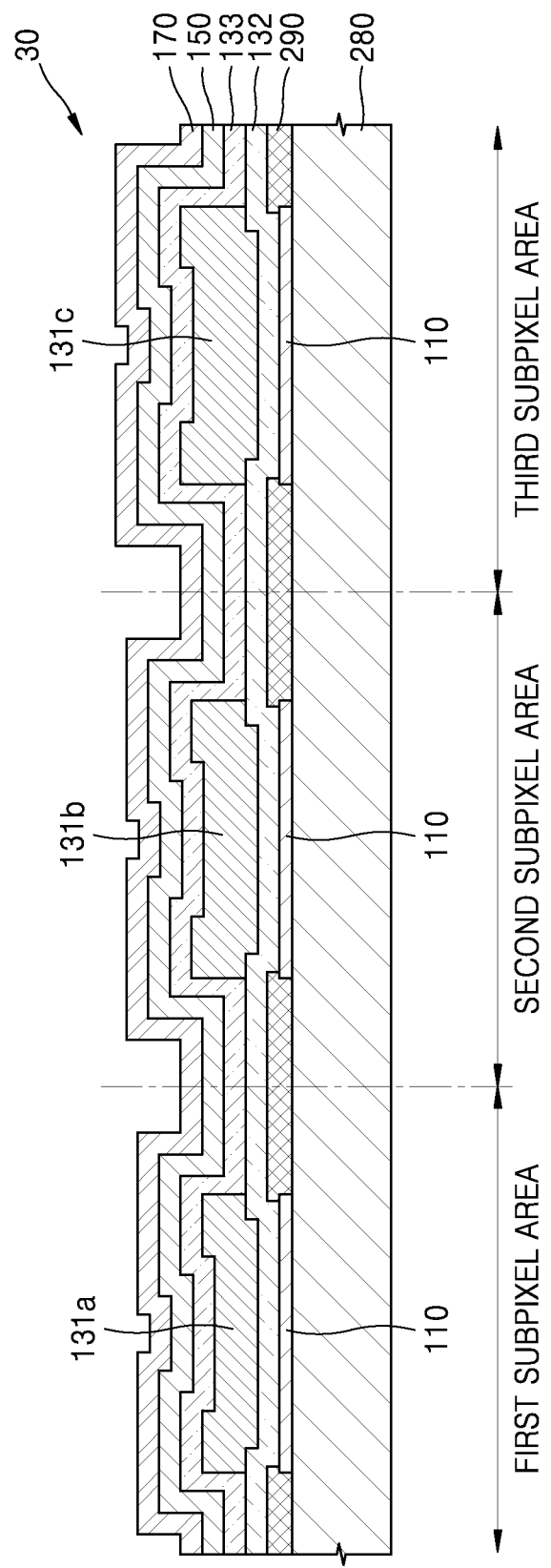
FIG. 4 is a cross-sectional view of a light-emitting apparatus according to an embodiment.

Description of FIGS. 2 to 4

FIG. 2 is a cross-sectional view of a light-emitting apparatus according to an embodiment of the disclosure.

The light-emitting apparatus of FIG. 2 includes a substrate 100, a thin-film transistor (TFT), a light-emitting device, and an encapsulation portion (or an encapsulation layer) 300 that seals the light-emitting device.

The substrate 100 may be a flexible substrate, a glass substrate, or a metal substrate. A buffer layer 210 may be formed on the substrate 100. The buffer layer 210 may prevent or reduce penetration of impurities through the substrate 100 and may provide a flat surface on the substrate 100.

A TFT may be located on the buffer layer 210. The TFT may include an activation layer 220, a gate electrode 240, a source electrode 260, and a drain electrode 270.

The activation layer 220 may include an inorganic semiconductor such as silicon and/or polysilicon, an organic semiconductor, and/or an oxide semiconductor, and may include a source region, a drain region and a channel region.

A gate insulating film 230 for insulating the activation layer 220 from the gate electrode 240 may be located on the activation layer 220, and the gate electrode 240 may be located on the gate insulating film 230.

An interlayer insulating film 250 is located on the gate electrode 240. The interlayer insulating film 250 may be placed between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the activation layer 220, and the source electrode 260 and the drain electrode 270 may be in contact with the exposed portions of the source region and the drain region of the activation layer 220.

The TFT is electrically connected to a light-emitting device to drive the light-emitting device, and may be covered by a passivation layer 280. The passivation layer 280 may include an inorganic insulating film, an organic insulating film, or a combination thereof. A light-emitting device may be provided on the passivation layer 280. The light-emitting device may include a first electrode 110, an interlayer 130, and a second electrode 150.

The first electrode 110 may be formed on the passivation layer 280. The passivation layer 280 may not completely cover the drain electrode 270 and may expose a portion of the drain electrode 270, and the first electrode 110 may be connected to the exposed portion of the drain electrode 270.

A pixel-defining layer 290 including an insulating material may be located on the first electrode 110. The pixel-defining layer 290 may expose a region of the first electrode 110, and an interlayer 130 may be formed in the exposed region of the first electrode 110. The pixel-defining layer 290 may be a polyimide or a polyacrylic organic film. In one embodiment, one or more layers of the interlayer 130 may extend beyond the upper portion of the pixel-defining layer 290 in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be formed on the capping layer 170. The encapsulation portion 300 may be formed on a light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, and/or the like), an epoxy-based resin (for example, aliphatic glycidyl ether (AGE), and/or the like), or a combination thereof; or a combination of the inorganic film and the organic film.

FIG. 3 is a cross-sectional view of a light-emitting apparatus according to an embodiment of the disclosure.

The light-emitting apparatus of FIG. 3 is the same as the light-emitting apparatus of FIG. 2, except that a light-shielding pattern 500 and a functional region 400 are additionally placed on the encapsulation portion 300. The functional region 400 may be i) a color filter area, ii) a color conversion area, or iii) a combination of the color filter area and the color conversion area. In an embodiment, the light-emitting device included in the light-emitting apparatus of FIG. 3 may be a tandem light-emitting device.

FIG. 4 is a schematic cross-sectional view of a full-color light-emitting device 30 according to an embodiment of the disclosure. Hereinafter, only differences from the light-emitting device 10 are described in more detail.

The light emitting device 30 may include: a substrate partitioned into a first subpixel area, a second subpixel area, and a third subpixel area; a plurality of anodes 110 respectively located in the first subpixel area, the second subpixel area, and the third subpixel area of the substrate; a cathode 150 facing the plurality of anodes 110; a capping layer 170 on the cathode 150; and an interlayer located between the plurality of anodes 110 and the cathode 150 and including a first emission layer 131a, a second emission layer 131b, and a third emission layer 131c respectively located in the first subpixel area, the second subpixel area, and the third subpixel area of the substrate, wherein the interlayer further includes: a common hole transport region 132 between the first electrode and the first emission layer 131a, the second emission layer 131b, and the third emission layer 131c; and a common electron transport region 133 between the second electrode and the first emission layer 131a, the second emission layer 131b, and the third emission layer 131c.

The hole transport region 132 may include the first to third compounds as described above.

The first emission layer 131a may emit a first-color light, the second emission layer 131b may emit a second-color light, and the third emission layer 131c may emit a third-color light.

The first-color light, the second-color light, and the third-color light may have different maximum emission wavelengths from one another.

The first-color light, the second-color light, and the third-color light may be mixed to emit white light.

In an embodiment, the first-color light may be red light, the second-color light may be green light, and the third-color light may be blue light, but embodiments of the disclosure are not limited thereto.

When the first-color light is blue light, the first emission layer 131a may include a suitable blue light-emitting material, when the first-color light is red light, the first emission layer 131a may include a suitable red light-emitting material, and when the first-color light is green light, the first emission layer 131a may include a suitable green light-emitting material. In an embodiment, the first emission layer 131a may include a suitable host and a suitable dopant. The host and the dopant may each be understood with reference to the description of FIG. 1.

The first electrode 110, the hole transport region 132, the electron transport region 133, the second electrode 150, and the capping layer 170 may each be understood with reference to the description of FIG. 1, and the first emission layer 131a, the second emission layer 131b, and the third emission layer 131c may each be the same as described in connection with the emission layer 131 in the description of FIG. 1.

Manufacture Method

Respective layers included in the hole transport region, the emission layer, and respective layers included in the electron transport region may be formed in a certain region by utilizing one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron-transporting region are formed by vacuum deposition, the vacuum deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

Definition of Terms

The term "$C_3$-$C_{60}$ carbocyclic group" as used herein refers to a cyclic group consisting of only carbon atoms as ring-forming atoms and having three to sixty carbon atoms, and the term "$C_1$-$C_{60}$ heterocyclic group" as used herein refers to a cyclic group that further includes a heteroatom, other than carbon atoms, as a ring-forming atom and having 1 to 60 carbon atoms. The $C_3$-$C_{60}$ carbocyclic group and the $C_1$-$C_{60}$ heterocyclic group may each be a monocyclic group consisting of one ring or a polycyclic group in which two or more rings are condensed with each other. In an embodiment, the $C_1$-$C_{60}$ heterocyclic group may have 3 to 61 ring-forming atoms.

The term "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein refers to a cyclic group that has three to sixty carbon atoms and does not include *—N=*' as a ring-forming moiety, and the term "π electron-deficient nitrogen-containing $C_1$-$C_{60}$ cyclic group" as used herein refers to a heterocyclic group that has one to sixty carbon atoms and includes *—N=*' as a ring-forming moiety.

In an embodiment,
the $C_3$-$C_{60}$ carbocyclic group may be i) a T1 group or ii) a condensed cyclic group in which two or more T1 groups are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group),
the $C_1$-$C_{60}$ heterocyclic group may be i) a T2 group, ii) a condensed cyclic group in which two or more T2 groups are condensed with each other, or iii) a condensed cyclic group in which at least one T2 group and at least one T1 group are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be i) a T1 group, ii) a condensed cyclic group in which two or more T1 groups are condensed with each other, iii) a T3 group, iv) a condensed cyclic group in which two or more T3 groups are condensed with each other, or v) a condensed cyclic group in which at least one T3 group and at least one T1 group are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be i) a T4 group, ii) a condensed cyclic group in which two or more T4 groups are condensed with each other, iii) a condensed cyclic group in which at least one T4 group and at least one T1 group are condensed with each other, iv) a condensed cyclic group in which at least one T4 group and at least one T3 group are condensed with each other, or v) a condensed cyclic group in which at least one T4 group, at least one T1 group, and at least one T3 group are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane group (or a bicyclo[2.2.1]heptane group), a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The term "cyclic group", "$C_3$-$C_{60}$ carbocyclic group", "$C_1$-$C_{60}$ heterocyclic group", "π electron-rich $C_3$-$C_{60}$ cyclic group", or "π electron-deficient nitrogen-containing $C_1$-$C_{60}$ cyclic group" as used herein each refers to a group condensed to any cyclic group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, and/or the like, which may be easily understood by one of ordinary skill in the art according to the structure of the formula including the "benzene group."

Examples of the monovalent $C_3$-$C_{60}$ carbocyclic group and the monovalent $C_1$-$C_6$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group.

The term "$C_1$-$C_{60}$ alkyl group" as used herein refers to a linear or branched aliphatic hydrocarbon monovalent group that has one to sixty carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a monovalent hydrocarbon group having at least one double bond in the middle or at a terminal end (e.g., the terminus) of a $C_2$-$C_{60}$ alkyl group, and examples thereof may include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle or at a terminal end (e.g., the terminus) of a $C_2$-$C_{60}$ alkyl group, and examples thereof may include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof may include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof may include a cyclopropyl group, a cyclobutyl group, a cyclopentyl group, a cyclohexyl group, a cycloheptyl group, a cyclooctyl group, an adamantanyl group, a norbornanyl group (or a bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group that further includes, in addition to carbon atom(s), at least one heteroatom as a ring-forming atom and has 1 to 10 carbon atoms, and examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent cyclic group that has three to ten carbon atoms and at least one double bond in the ring thereof and no aromaticity, and examples thereof may include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group that has, in addition to carbon atom(s), at least one heteroatom as a ring-forming atom, 1 to 10 carbon atoms, and at least one double bond in the cyclic structure thereof. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having six to sixty carbon atoms, and the term "$C_6$-$C_{60}$ arylene group" as used herein refers to a divalent group having a carbocyclic aromatic system having six to sixty carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, a fluorenyl group, and an ovalenyl group. When the $C_6$-$C_{60}$ aryl group and the $C_6$-$C_{60}$ arylene group each include two or more rings, the two or more rings may be condensed with each other.

The term "$C_1$-$C_{60}$ heteroaryl group" as used herein refers to a monovalent group having a heterocyclic aromatic system that has, in addition to carbon atom(s), at least one heteroatom as a ring-forming atom, and 1 to 60 carbon atoms. The term "$C_1$-$C_{60}$ heteroarylene group" as used herein refers to a divalent group having a heterocyclic aromatic system that has, in addition to carbon atom(s), at least one heteroatom as a ring-forming atom, and 1 to 60 carbon atoms. Examples of the $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, a carbazolyl group, a dibenzofuranyl group, a dibenzothiofuranyl group, and a naphthyridinyl group. When the $C_1$-$C_{60}$ heteroaryl group and the $C_1$-$C_{60}$ heteroarylene group each include two or more rings, the two or more rings may be condensed with each other.

The term "monovalent non-aromatic condensed polycyclic group" as used herein refers to a monovalent group having two or more rings condensed to each other, only carbon atoms (for example, having 8 to 60 carbon atoms) as ring-forming atoms, and non-aromaticity in its molecular structure when considered as a whole (e.g., the entire molecular structure is not aromatic). Examples of the monovalent non-aromatic condensed polycyclic group may include an indenyl group, a fluorenyl group, a spiro-bifluorenyl group, a benzofluorenyl group, an indenophenanthrenyl group, an adamantyl group, and an indeno anthracenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, at least one heteroatom other than 1 to 60 carbon atoms as a ring-forming atom, and having non-aromaticity in its molecular structure when considered as a whole (e.g., the entire molecular structure is not aromatic). Examples of the monovalent non-aromatic condensed heteropolycyclic group may include a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, an azaadamantyl group, and a benzothienodibenzothiophenyl group. The term "divalent non-aromatic condensed heteropolycyclic group" as used herein refers to a divalent group having the same structure as the monovalent non-aromatic condensed heteropolycyclic group.

The term "$C_6$-$C_{60}$ aryloxy group" as used herein refers to a monovalent group represented by —$OA_{102}$ (wherein $A_{102}$ is the $C_6$-$C_{60}$ aryl group), and the term "$C_6$-$C_{60}$ arylthio group" as used herein refers to a monovalent group represented by —$SA_{103}$ (wherein $A_{103}$ is the $C_6$-$C_{60}$ aryl group).

The term "$C_7$-$C_{60}$ aryl alkyl group" used herein refers to a monovalent group represented by -$A_{104}A_{105}$ (wherein $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" as used herein refers to a monovalent group represented by -$A_{106}A_{107}$ (wherein $A_{106}$ may be a $C_1$-$C_{59}$ alkylene group, and $A_{107}$ may be a $C_1$-$C_{59}$ heteroaryl group).

$R_{10a}$ may be:
deuterium (-D), —F, —Cl, —Br, —I, a hydroxyl group, a cyano group, or a nitro group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;
a $C_3$-$C_{60}$ carbocyclic group, a $C_1$-$C_6$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or
—$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

$Q_1$ to $Q_3$, $Q_{11}$ to $Q_{13}$, $Q_{21}$ to $Q_{23}$, and $Q_{31}$ to $Q_{33}$ used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "hetero atom" as used herein refers to any atom other than a carbon atom. Examples of the heteroatom may include O, S, N, P, Si, B, Ge, Se, or any combination thereof.

The term "the third-row transition metal" used herein includes hafnium (Hf), tantalum (Ta), tungsten (W), rhenium (Re), osmium (Os), iridium (Ir), platinum (Pt), gold (Au), and/or the like.

The term "Ph" as used herein refers to a phenyl group, the term "Me" as used herein refers to a methyl group, the term "Et" as used herein refers to an ethyl group, the term "ter-Bu" or "Bu$^t$" as used herein refers to a tert-butyl group, and the term "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". The "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula or moiety.

Hereinafter, a compound according to embodiments and a light-emitting device according to embodiments will be described in more detail with reference to Examples. The wording "B was utilized instead of A" utilized in describing Examples refers to that an identical molar equivalent of B was utilized in place of an identical molar equivalent of A.

EXAMPLES

Evaluation Example 1: Measurement of Triplet Energy Level ($T_1$)

Triplet energy levels ($T_1$) of Compounds 48, 51, 54, FD37, PD11, and PD13 are each evaluated utilizing the DFT method of the Gaussian program, which is structure-optimized at the B3LYP/6-31 G(d,p) level and are shown in Table 1.

TABLE 1

| Compound | Triplet energy level (T₁, eV) |
|---|---|
| 39 | 2.6 |
| 48 | 2.6 |
| 51 | 2.7 |
| 54 | 2.6 |
| FD37 | 2.0 |
| PD13 | 2.4 |
| PD11 | 2.0 |

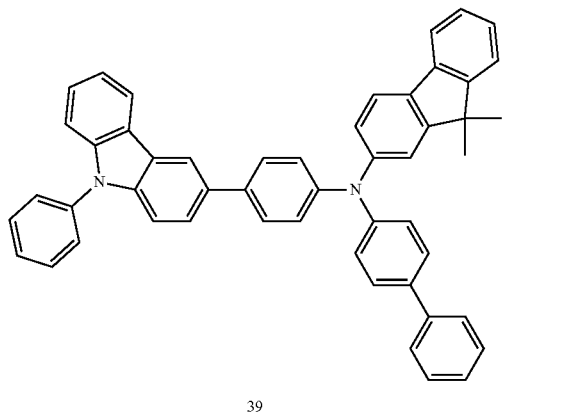 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

39

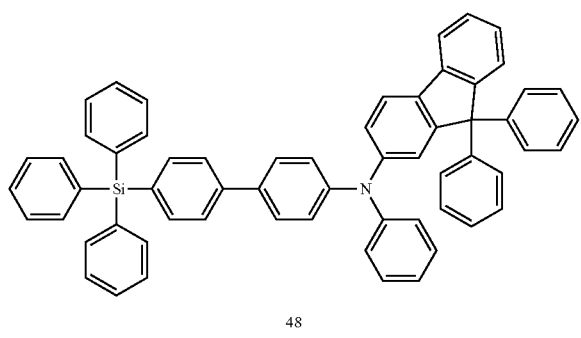 [SMILES: c1ccc(N(c2ccc(-c3ccc([Si](c4ccccc4)(c4ccccc4)c4ccccc4)cc3)cc2)c2ccc3c(c2)C(c2ccccc2)(c2ccccc2)c2ccccc2-3)cc1]

48

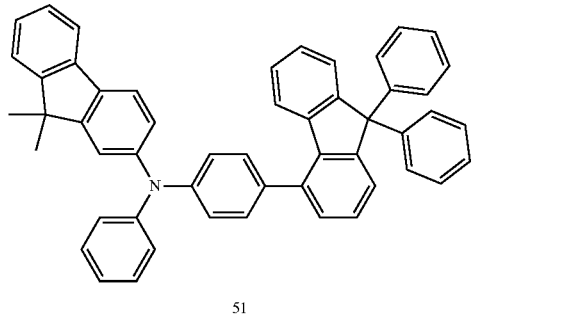 [SMILES: CC1(C)c2ccccc2-c2ccc(N(c3ccccc3)c3ccc(-c4cccc5c4-c4ccccc4C5(c4ccccc4)c4ccccc4)cc3)cc21]

51

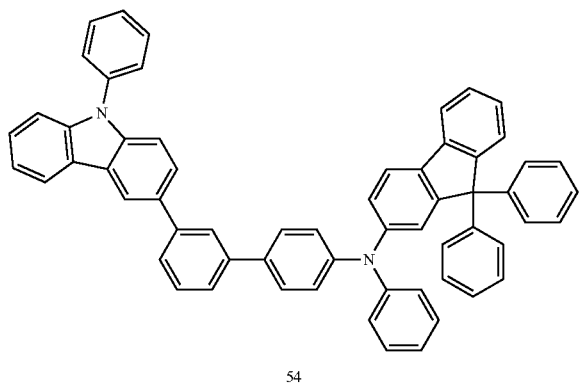 [SMILES: c1ccc(N(c2ccc(-c3cccc(-c4ccc5c(c4)c4ccccc4n5-c4ccccc4)c3)cc2)c2ccc3c(c2)C(c2ccccc2)(c2ccccc2)c2ccccc2-3)cc1]

54

FD37

PD13

PD11

In table 1, Compounds 48, 51, and 54 each satisfy Equation 1 of the disclosure with respect to FD37, PD13, and PD11, respectively.

Example 1-1

As an anode, a 15 Ω/cm² (1,200 Å) ITO glass substrate available from Corning Inc. was cut to a size of 50 mm×50 mm×0.5 mm, sonicated with isopropyl alcohol and pure water each for 15 minutes, and then cleaned by irradiation of ultraviolet rays and exposure of ozone thereto for 30 minutes. The ITO glass substrate was provided to a vacuum deposition apparatus.

Compound 8 was vacuum-deposited on the ITO anode formed on the glass substrate to form a first hole transport layer having a thickness of 10 nm.

Compound 31 was vacuum-deposited on the first hole transport layer to form a second hole transport layer having a thickness of 110 nm, and Compound 48 was vacuum-deposited on the second hole transport layer to form a third hole transport layer having a thickness of 10 nm.

H8 (host) and FD37 (dopant) were co-deposited on the third hole transport layer at a weight ratio of 97:3 to form an emission layer having a thickness of 20 nm.

Next, ET46 was deposited on the emission layer to form a first electron transport layer having a thickness of 5 nm, and ET47 and ET-D1 were co-deposited on the first electron transport layer at a weight ratio of 50:50 to form a second electron transport layer having a thickness of 30 nm.

ET-D1 was deposited on the second electron transport layer to form an electron injection layer having a thickness of 1 nm, and Mg and Ag were co-deposited at a weight ratio of 10:90 to form an electrode having a thickness of 10 nm, thereby manufacturing a light-emitting device.

8

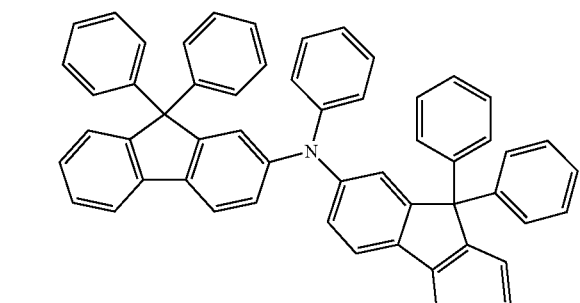

31

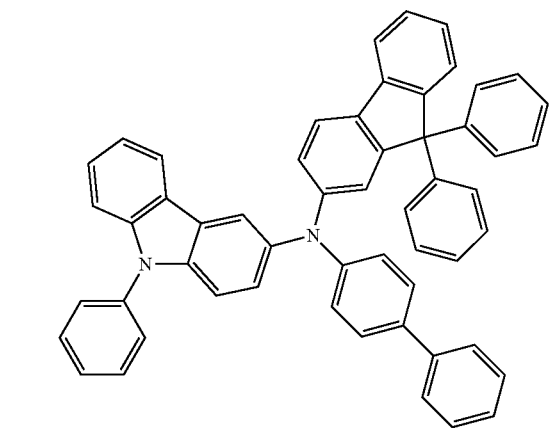

48

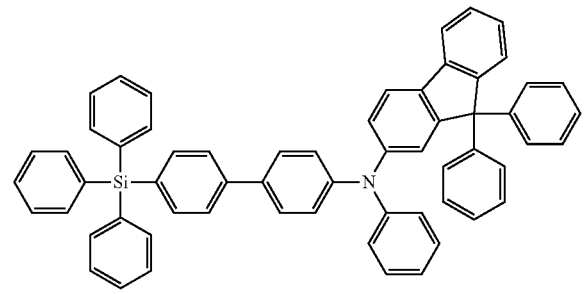

H8

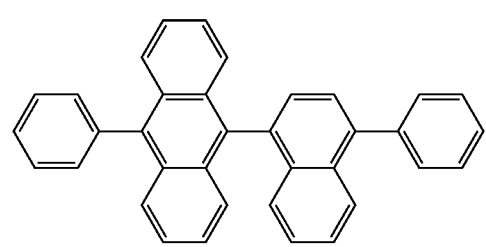

-continued

FD37

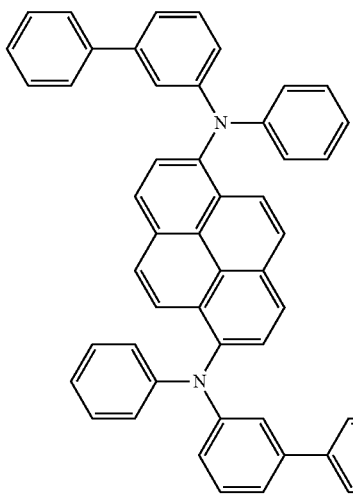

ET46

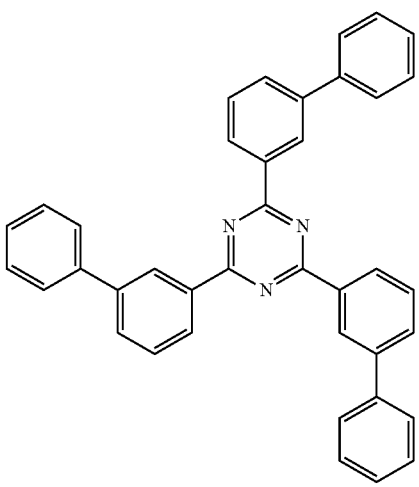

ET47

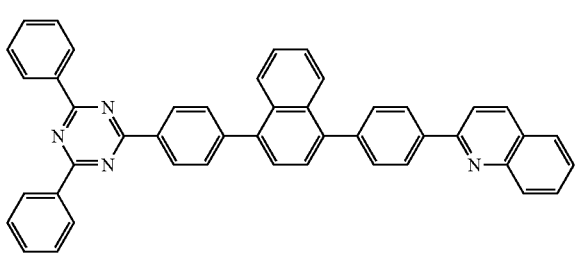

ET-D1

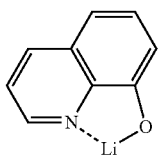

Examples 1-2, 1-4, and 1-6

Light-emitting devices were manufactured in the same manner as in Example 1-1, except that, in forming a first hole transport layer, the respective first compound in Table 2 was formed to have a thickness of 60 nm, and in forming a second hole transport layer, the respective second compound in Table 2 was formed to have a thickness of 60 nm.

Examples 1-3 and 1-5

Light-emitting devices were manufactured in the same manner as in Example 1-1, except that, in forming a first hole transport layer, the respective first compound in Table 2 was utilized, and in forming a second hole transport layer, the respective second compound in Table 2 was utilized.

Comparative Example 1-1

Light-emitting devices were manufactured in the same manner as in Example 1-1, except that, without forming a first hole transport layer on the ITO anode, Compound 31 was vacuum-deposited on the ITO anode to form a second hole transport layer having a thickness of 120 nm.

Comparative Example 1-2

Light-emitting devices were manufactured in the same manner as in Example 1-1, except that Compound 39 and HAT-CN were co-deposited on the ITO anode at a weight ratio of 98:2 to form a first hole transport layer having a thickness of 10 nm, Compound 31 was vacuum-deposited on the first hole transport layer to form a second hole transport layer having a thickness of 40 nm, Compound 39 and HAT-CN were co-deposited on the second hole transport layer at a weight ratio of 98:2 to form a third hole transport layer having a thickness of 20 nm, Compound 31 was vacuum-deposited on the third hole transport layer to form a fourth hole transport layer having a thickness of 40 nm, and Compound 39 was vacuum-deposited on the fourth hole transport layer to form a buffer layer having a thickness of 20 nm.

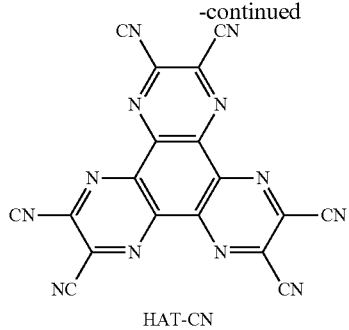

HAT-CN

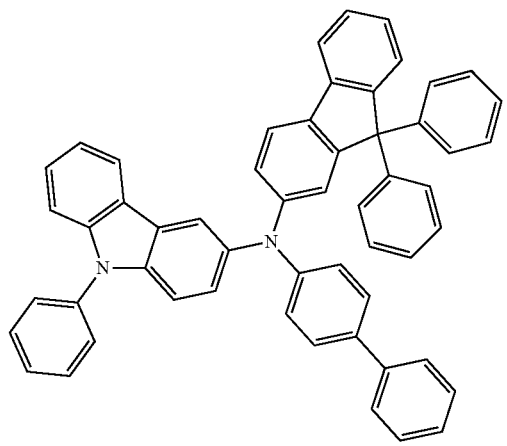

31

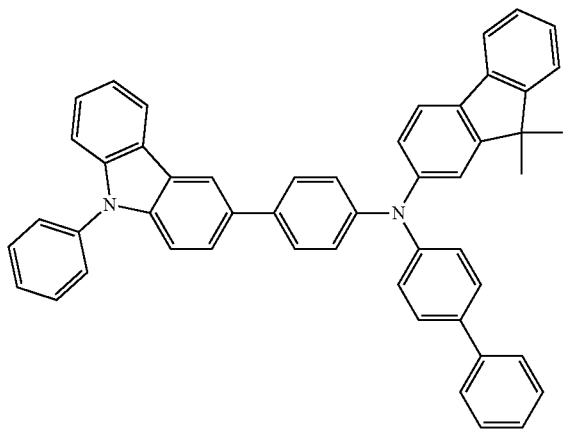

39

Evaluation Example 2

In order to evaluate characteristics of the light-emitting devices manufactured in Examples 1-1 to 1-6, Comparative Example 1-1, and Comparative Example 1-2, each of driving voltage (ΔV) at 1,000 cd/n$^2$, luminescence efficiency (%), lifespan (%), and emission color of the light-emitting devices was measured utilizing Keithley MU 236 and luminance meter PR650, and results are shown in Table 2. The driving voltage was converted to a difference value by assuming the driving voltage of Comparative Example 1-1 as 0. That is, the driving voltage values were calculated as a difference between the driving voltage of a sample and that of Comparative Example 1-1. The luminescence efficiency was converted utilizing the luminescence efficiency of Comparative Example 1-1 as 100%. The lifespan was obtained by measuring the time taken for the luminance to reach 95% relative to the initial luminance, and then converted utilizing the lifespan of Comparative Example 1-1 as 100%.

TABLE 2

| | First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|---|
| Example 1-1 | Compound 8 (10 nm) | Compound 31 (110 nm) | Compound 48 (10 nm) | −0.2 V | 105% | 110% | Blue light |
| Example 1-2 | Compound 8 (60 nm) | Compound 31 (60 nm) | Compound 48 (10 nm) | −0.3 V | 107% | 108% | Blue light |

TABLE 2-continued

| | First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|---|
| Example 1-3 | Compound 10 (10 nm) | Compound 32 (110 nm) | Compound 48 (10 nm) | −0.25 V | 110% | 115% | Blue light |
| Example 1-4 | Compound 10 (60 nm) | Compound 32 (60 nm) | Compound 48 (10 nm) | −0.3 V | 108% | 115% | Blue light |
| Example 1-5 | Compound 16 (10 nm) | Compound 32 (110 nm) | Compound 48 (10 nm) | −0.2 V | 106% | 120% | Blue light |
| Example 1-6 | Compound 16 (60 nm) | Compound 32 (60 nm) | Compound 48 (10 nm) | −0.25 V | 106% | 115% | Blue light |
| Comparative Example 1-1 | — | Compound 31 (120 nm) | Compound 48 (10 nm) | — | 100% | 100% | Blue light |
| Comparative Example 1-2 | Compound 39: HAT-CN (10 nm) | Compound 31 (40 nm) | Compound 39: HAT-CN (20 nm) | −0.1 V | 95% | 85% | Blue light |

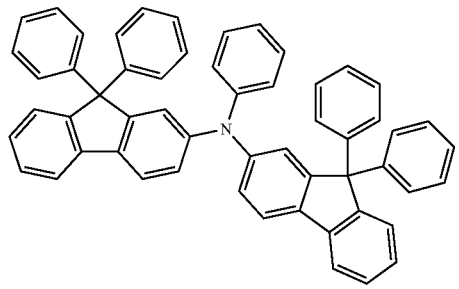

8

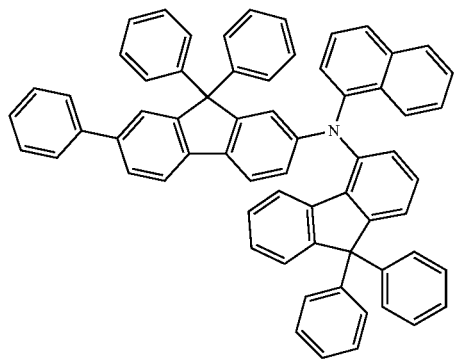

10

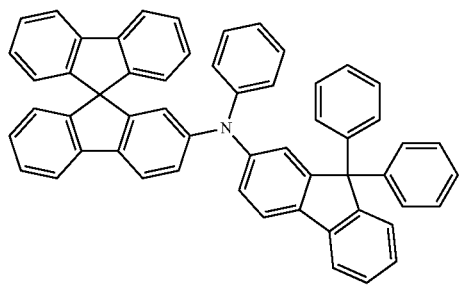

16

TABLE 2-continued
| First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|
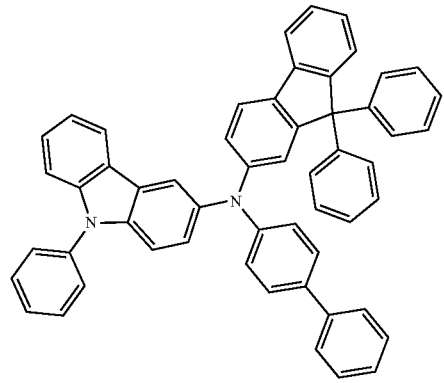
31
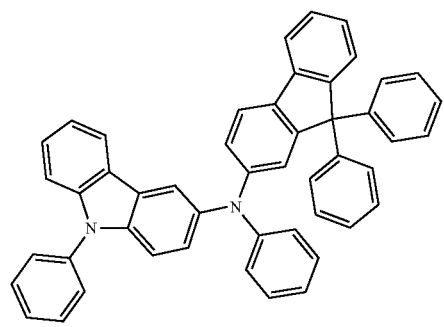
32
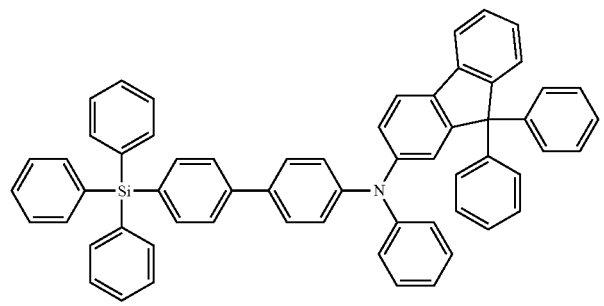
48
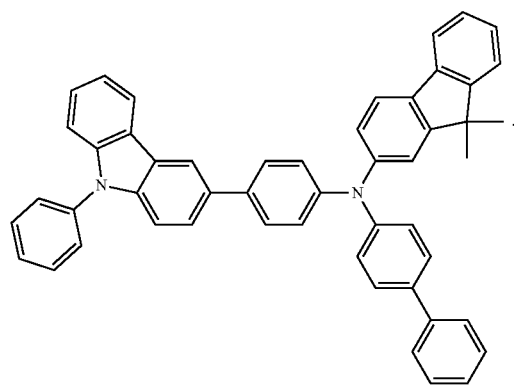
39

From Table 2, it may be confirmed that the light-emitting devices of Examples 1-1 to 1-6 each have reduced driving voltage, increased luminescence efficiency, and increased lifespan, compared to the light-emitting devices of Comparative Examples 1-1 and 1-2.

Example 2-1

As an anode, a 15 Ω/cm² (1,200 Å) ITO glass substrate available from Corning Inc. was cut to a size of 50 mm×50 mm×0.5 mm, sonicated with isopropyl alcohol and pure water each for 15 minutes, and then cleaned by irradiation of ultraviolet rays and exposure of ozone thereto for 30 minutes. The ITO glass substrate was provided to a vacuum deposition apparatus.

Compound 8 was vacuum-deposited on the ITO anode formed on the glass substrate to form a first hole transport layer having a thickness of 10 nm.

Compound 31 was vacuum-deposited on the first hole transport layer to form a second hole transport layer having a thickness of 110 nm, and Compound 51 was vacuum-deposited on the second hole transport layer to form a third hole transport layer having a thickness of 30 nm.

CBP (host) and PD13 (dopant) were co-deposited on the third hole transport layer at a weight ratio of 90:10 to form an emission layer having a thickness of 40 nm.

Next, ET46 was deposited on the emission layer to form a first electron transport layer having a thickness of 5 nm, and ET47 and ET-D1 were co-deposited on the first electron transport layer at a weight ratio of 50:50 to form a second electron transport layer having a thickness of 30 nm.

ET-D1 was deposited on the second electron transport layer to form an electron injection layer having a thickness of 1 nm, and Mg and Ag were co-deposited at a weight ratio of 10:90 to form an electrode having a thickness of 10 nm, thereby manufacturing a light-emitting device.

-continued

31

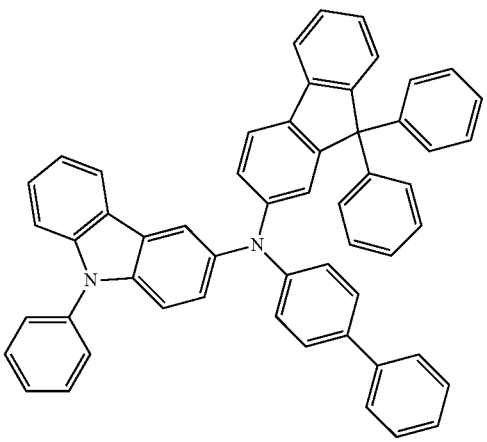

51

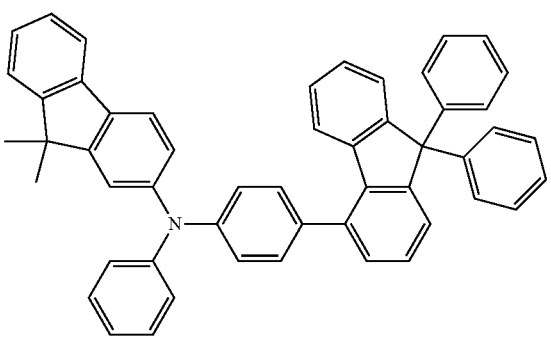

CBP

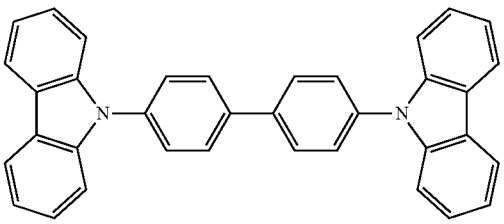

8

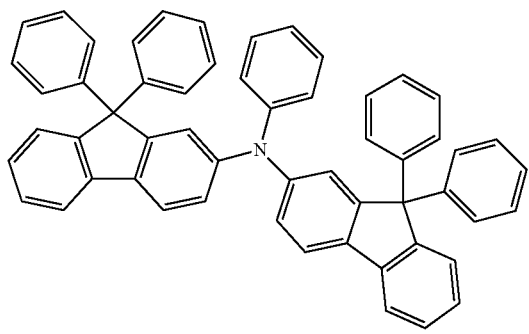

PD13

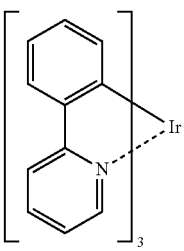

ET46

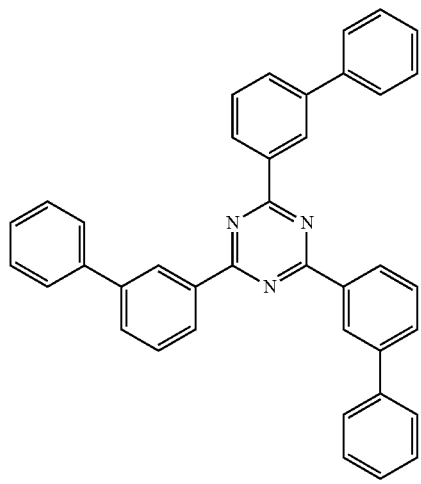

ET47

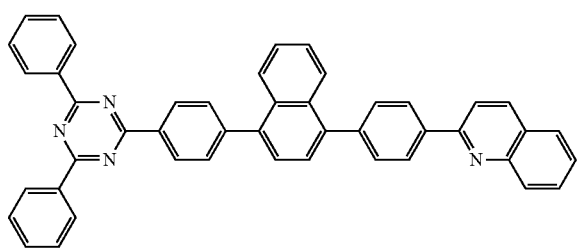

Examples 2-2 and 2-3

Light-emitting devices were manufactured in the same manner as in Example 2-1, except that, in forming a first hole transport layer, the first compound in Table 3 was utilized, and in forming a second hole transport layer, the second compound in Table 3 was utilized.

Comparative Example 2-1

Light-emitting devices were manufactured in the same manner as in Example 2-1, except that, without forming a first hole transport layer on the ITO anode, Compound 31 was vacuum-deposited on the ITO anode to form a second hole transport layer having a thickness of 120 nm.

Evaluation Example 3

In order to evaluate characteristics of the light-emitting devices manufactured in Examples 2-1 to 2-3 and Comparative Example 2-1, each of driving voltage (V) at 12,000 cd/m$^2$, luminescence efficiency (%), lifespan (%), and emission color of the light-emitting devices was measured utilizing Keithley MU 236 and luminance meter PR650, and results are shown in Table 3. The driving voltage is converted to a difference value by assuming the driving voltage of Comparative Example 2-1 as 0. That is, the driving voltage values were calculated as a difference between the driving voltage of a sample and that of Comparative Example 2-1. The luminescence efficiency was converted utilizing the luminescence efficiency of Comparative Example 2-1 as 100%. The lifespan was obtained by measuring the time taken for the luminance to reach 95% relative to the initial luminance, and then converted utilizing the lifespan of Comparative Example 2-1 as 100%.

TABLE 3

|  | First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|---|
| Example 2-1 | Compound 8 (10 nm) | Compound 31 (110 nm) | Compound 51 (30 nm) | −0.25 V | 108% | 115% | Green light |
| Example 2-2 | Compound 10 (10 nm) | Compound 32 (110 nm) | Compound 51 (30 nm) | −0.3 V | 110% | 120% | Green light |
| Example 2-3 | Compound 16 (10 nm) | Compound 32 (110 nm) | Compound 51 (30 nm) | −0.3 V | 108% | 115% | Green light |
| Comparative Example 2-1 | — | Compound 31 (120 nm) | Compound 51 (30 nm) | — | 100% | 100% | Green light |

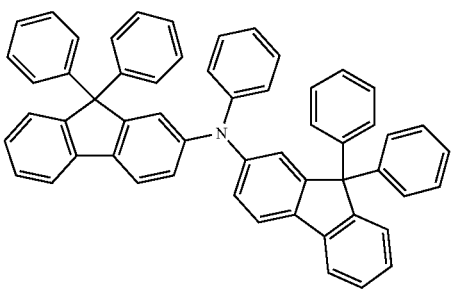

TABLE 3-continued
| First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|
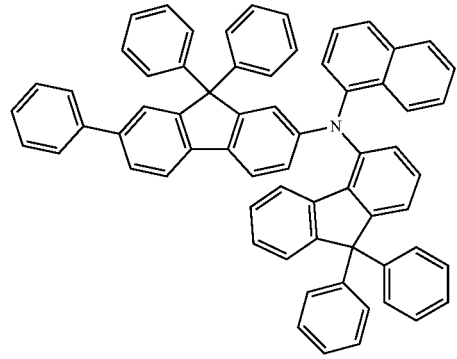
10
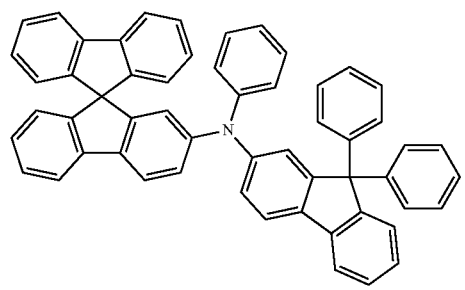
16
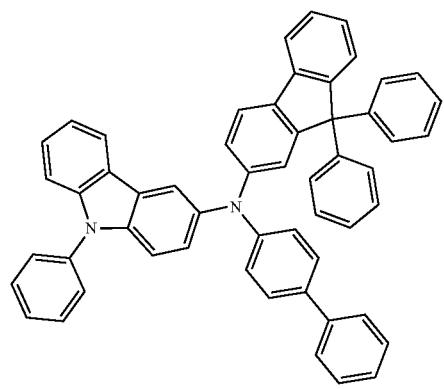
31
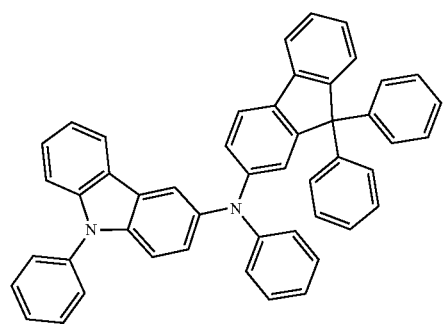
32

TABLE 3-continued

| First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|

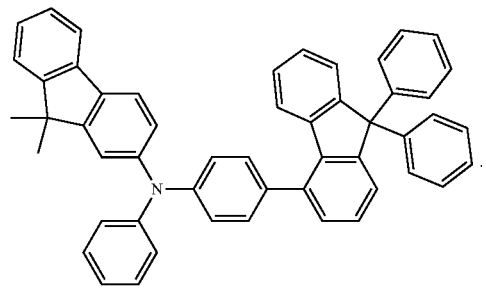

51

From Table 3, it may be confirmed that the light-emitting devices of Examples 2-1 to 2-3 each have reduced driving voltage, increased luminescence efficiency, increased lifespan and increased maximum quantum efficiency, compared to the light-emitting device of Comparative Example 2-1.

Example 3-1

As an anode, a 15 Ω/cm² (1,200 Å) ITO glass substrate available from Corning Inc. was cut to a size of 50 mm×50 mm×0.5 mm, sonicated with isopropyl alcohol and pure water each for 15 minutes, and then cleaned by irradiation of ultraviolet rays and exposure of ozone thereto for 30 minutes. The ITO glass substrate was provided to a vacuum deposition apparatus.

Compound 8 was vacuum-deposited on the ITO anode formed on the glass substrate to form a first hole transport layer having a thickness of 10 nm.

Compound 31 was vacuum-deposited on the first hole transport layer to form a second hole transport layer having a thickness of 110 nm, and Compound 54 was vacuum-deposited on the second hole transport layer to form a third hole transport layer having a thickness of 60 nm.

CBP (host) and PD11 (dopant) were co-deposited on the third hole transport layer at a weight ratio of 98:2 to form an emission layer having a thickness of 40 nm.

Next, ET46 was deposited on the emission layer to form a first electron transport layer having a thickness of 5 nm, and ET47 and ET-D1 were co-deposited on the first electron transport layer at a weight ratio of 50:50 to form a second electron transport layer having a thickness of 30 nm.

ET-D1 was deposited on the second electron transport layer to form an electron injection layer having a thickness of 1 nm, and Mg and Ag were co-deposited at a weight ratio of 10:90 to form an electrode having a thickness of 10 nm, thereby manufacturing a light-emitting device.

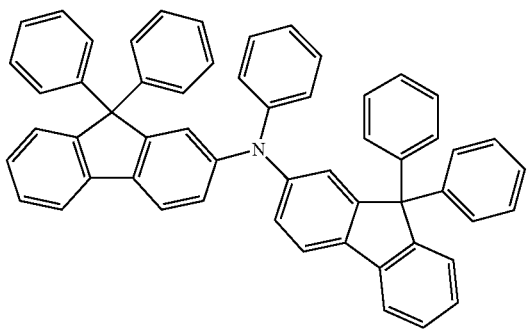

8

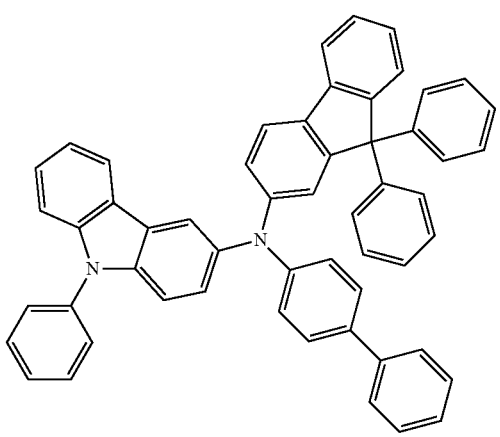

31

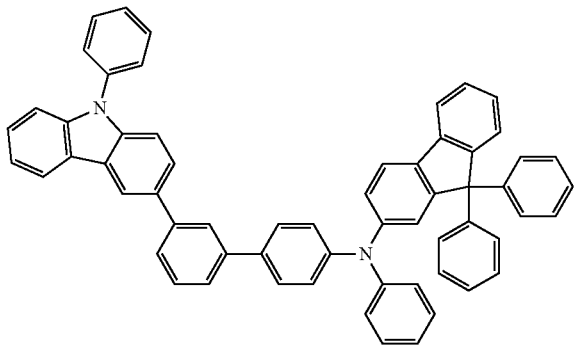

54

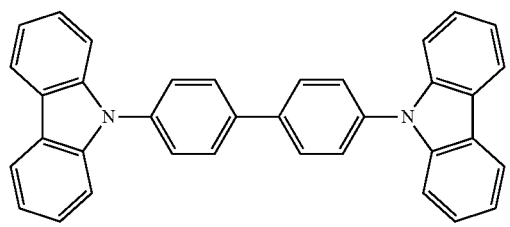

CBP

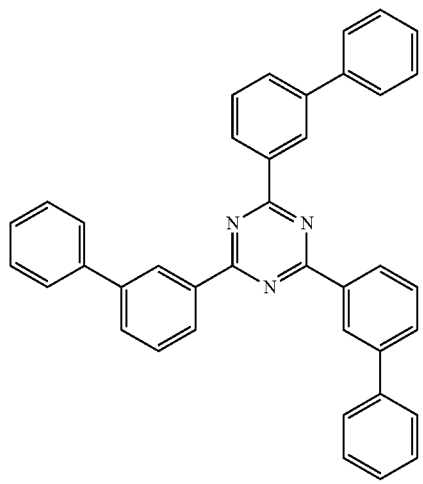

PD11

ET46

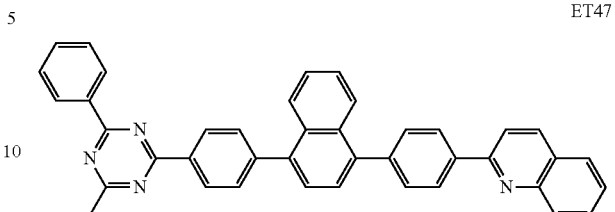

ET47

Examples 3-2 and 3-3

Light-emitting devices were manufactured in the same manner as in Example 3-1, except that, in forming a first hole transport layer, the first compound in Table 4 was utilized, and in forming a second hole transport layer, the second compound in Table 4 was utilized.

Comparative Example 3-1

Light-emitting devices were manufactured in the same manner as in Example 3-1, except that, without forming a first hole transport layer on the ITO anode, Compound 31 was vacuum-deposited on the ITO anode to form a second hole transport layer having a thickness of 120 nm.

Evaluation Example 4

In order to evaluate characteristics of the light-emitting devices manufactured in Examples 3-1 to 3-3 and Comparative Example 3-1, each of driving voltage (V) at 3,500 cd/m$^2$, luminescence efficiency (%), lifespan (%), and emission color of the light-emitting devices was measured utilizing Keithley MU 236 and luminance meter PR650, and results are shown in Table 4. The driving voltage is converted to a difference value by assuming the driving voltage of Comparative Example 3-1 as 0. That is, the driving voltage values were calculated as a difference between the driving voltage of a sample and that of Comparative Example 3-1. The luminescence efficiency was converted utilizing the luminescence efficiency of Comparative Example 3-1 as 100%. The lifespan was obtained by measuring the time taken for the luminance to reach 95% relative to the initial luminance, and then converted utilizing the lifespan of Comparative Example 3-1 as 100%.

TABLE 4

| | First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|---|
| Example 3-1 | Compound 8 (10 nm) | Compound 31 (110 nm) | Compound 54 (60 nm) | −0.4 V | 107% | 110% | Red light |
| Example 3-2 | Compound 10 (10 nm) | Compound 32 (110 nm) | Compound 54 (60 nm) | −0.45 V | 107% | 130% | Red light |
| Example 3-3 | Compound 16 (10 nm) | Compound 32 (110 nm) | Compound 54 (60 nm) | −0.4 V | 105% | 125% | Red light |
| Comparative Example 3-1 | — | Compound 31 (120 nm) | Compound 54 (60 nm) | — | 100% | 100% | Red light |

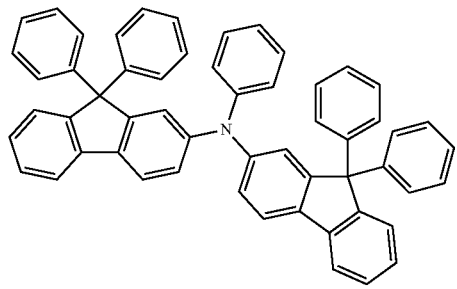

8

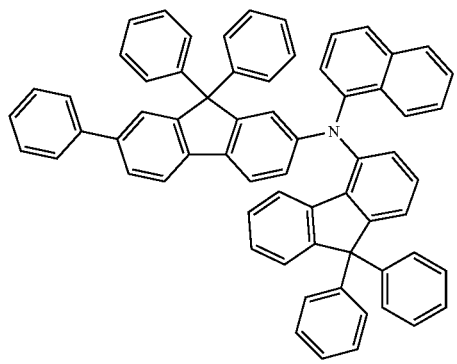

10

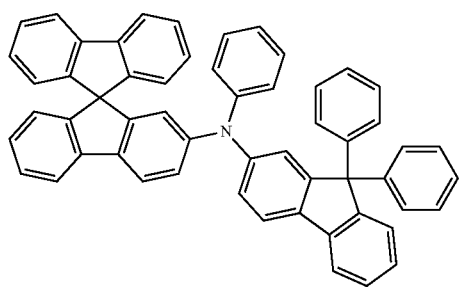

16

TABLE 4-continued

| First compound (thickness, nm) | Second compound (thickness, nm) | Third compound (thickness, nm) | Driving voltage (ΔV) | Luminescence efficiency (%) | Lifespan (%) | Emission color |
|---|---|---|---|---|---|---|

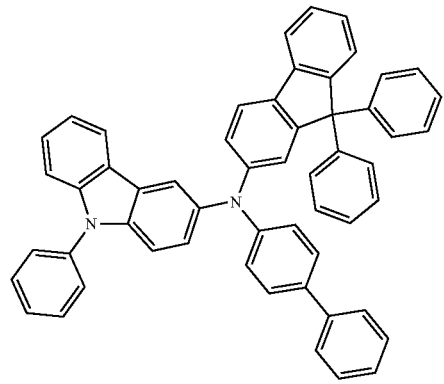

31

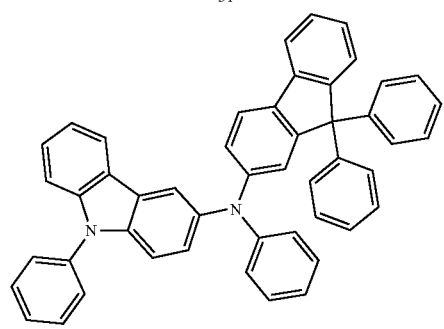

32

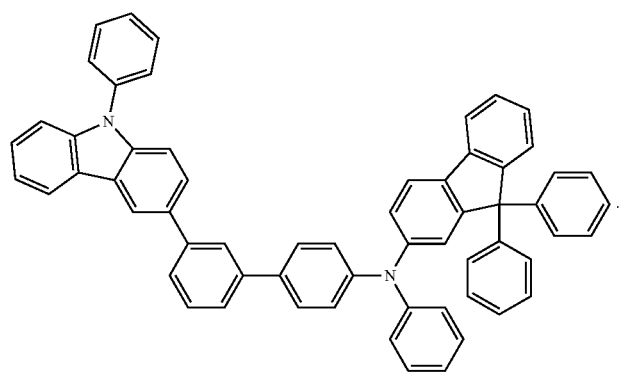

54

From Table 4, it may be confirmed that the light-emitting devices of Examples 3-1 to 3-3 each have reduced driving voltage, increased luminescence efficiency, increased lifespan and increased maximum quantum efficiency, compared to the light-emitting device of Comparative Example 3-1.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various suitable changes in form and details may be made therein without departing from the spirit and scope as defined by the following claims, and equivalents thereof.

What is claimed is:
1. A light-emitting device comprising:
a first electrode;
a second electrode facing the first electrode; and
an interlayer comprising an emission layer between the first electrode and the second electrode and a hole transport region between the first electrode and the emission layer,
wherein the emission layer comprises a dopant,
the hole transport region comprises a first hole transport layer, a second hole transport layer between the first hole transport layer and the emission layer, and a third hole transport layer between the second hole transport layer and the emission layer, the first hole transport layer comprises a first compound, the first compound being a carbazole-free compound, the second hole transport layer comprises a second compound, the third hole transport layer comprises a third compound, the first to third compounds are each independently an amine-based compound, and are different from each other, and Equation 1 is satisfied:

$$T_1(HTM3) \geq T_1(D) + 0.3 \text{ eV, and} \qquad \text{Equation 1}$$

wherein, in Equation 1, $T_1(HTM3)$ is a triplet energy level in electron volt (eV) of the third compound, $T_1(D)$ is a triplet energy level in electron volt (eV) of the dopant, and $T_1(HTM3)$ and $T_1(D)$ are values evaluated utilizing a density functional theory (DFT) method of a Gaussian program, which is structure-optimized at a B3LYP/6-31G(d,p) level.

2. The light-emitting device of claim 1, wherein the first electrode is an anode, the second electrode is a cathode, the interlayer further comprises an electron transport region between the emission layer and the second electrode, the hole transport region further comprises a hole injection layer, an emission auxiliary layer, an electron blocking layer, or any combination thereof, and the electron transport region comprises a buffer layer, a hole blocking layer, an electron control layer, an electron transport layer, an electron injection layer, or any combination thereof.

3. The light-emitting device of claim 1, wherein the hole transport region further comprises a p-dopant.

4. The light-emitting device of claim 1, wherein i) the first hole transport layer is in direct contact with the second hole transport layer, ii) the second hole transport layer is in direct contact with the third hole transport layer, or iii) the first hole transport layer is in direct contact with the second hole transport layer, and the second hole transport layer is in direct contact with the third hole transport layer.

5. The light-emitting device of claim 1, wherein the third hole transport layer is in direct contact with the emission layer.

6. The light-emitting device of claim 1, wherein a thickness of the first hole transport layer and a thickness of the third hole transport layer are each independently from 5 nm to 80 nm.

7. The light-emitting device of claim 1, wherein a thickness of the second hole transport layer is greater than or equal to the thickness of the first hole transport layer or the thickness of the third hole transport layer.

8. The light-emitting device of claim 1, wherein $T_1(HTM3)$ is 1.7 eV or more and 2.8 eV or less.

9. The light-emitting device of claim 1, wherein a difference between $T_1(HTM3)$ and $T_1(D)$ is 0.3 eV or more and 0.8 eV or less.

10. The light-emitting device of claim 1, wherein the first to third compounds are each independently represented by Formula 1-1 or Formula 1-2:

Formula 1-1

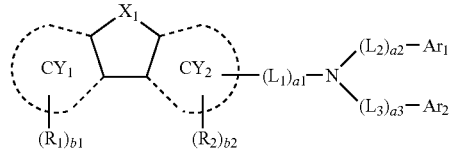

Formula 1-2

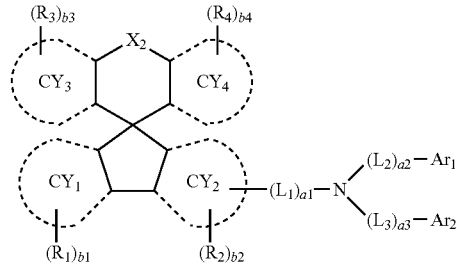

wherein, in Formula 1-1, $X_1$ is $*-C(Z_{1a})(Z_{1b})-*'$, in Formula 1-2, $X_2$ is a single bond, $*-O-**$, $*-S-**$, $*-C(Z_{2a})(Z_{2b})-**$, or $*-N(Z_{2a})(Z_{2b})-*'$, in Formulae 1-1 and 1-2, $CY_1$ to $CY_4$ are each independently a $C_3$-$C_{60}$ carbocyclic group or a $C_1$-$C_{60}$ heterocyclic group, $L_1$ to $L_3$ are each independently a single bond, a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, a1 to a3 are each independently an integer from 0 to 5, $Ar_1$ and $Ar_2$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_1$ to $R_4$, $Z_{1a}$, $Z_{1b}$, $Z_{2a}$, and $Z_{2b}$ are each independently:

hydrogen, deuterium, $-F$, $-Cl$, $-Br$, $-I$, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, $-Si(Q_1)(Q_2)(Q_3)$, $-B(Q_1)(Q_2)$, $-C(=O)(Q_1)$, $-S(=O)_2(Q_1)$, or $-P(=O)(Q_1)(Q_2)$, b1 to b4 are each independently an integer from 0 to 10, when b1 is 2 or more, two $R_1(s)$ of two or more $R_1(s)$ are optionally linked together to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, when b2 is 2 or more, two $R_2(s)$ of two or more $R_2(s)$ are optionally linked together to form a $C_4$-$C_{60}$ carbocyclic group unsubstituted or substituted with at least one $R_{10a}$ or a $C_1$-$C_{60}$ heterocyclic group unsubstituted or substituted with at least one $R_{10a}$, when b3 is 2 or more, two R$_3$(s) of two or more R$_3$(s) are optionally linked together to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, when b4 is 2 or more, two R$_4$(s) of two or more R$_4$(s) are optionally linked together to form a C$_4$-C$_{60}$ carbocyclic group unsubstituted or substituted with at least one R$_{10a}$ or a C$_1$-C$_{60}$ heterocyclic group unsubstituted or substituted with at least one R$_{10a}$, R$_{10a}$ is:

deuterium (—D), —F, —Cl, —Br, —I, a hydroxyl group, a cyano group, or a nitro group;

a C$_1$-C$_{60}$ alkyl group, a C$_2$-C$_{60}$ alkenyl group, a C$_2$-C$_{60}$ alkynyl group, or a C$_1$-C$_{60}$ alkoxy group, each unsubstituted or substituted with deuterium, —F, —Cl, —Br, —I, a hydroxyl group, a cyano group, a nitro group, a C$_3$-C$_{60}$ carbocyclic group, a C$_1$-C$_{60}$ heterocyclic group, a C$_6$-C$_{60}$ aryloxy group, a C$_6$-C$_{60}$ arylthio group, —Si(Q$_{11}$)(Q$_{12}$)(Q$_{13}$), —B(Q$_{11}$)(Q$_{12}$), —C(=O)(Q$_{11}$), —S(=O)$_2$(Q$_{11}$), —P(=O)(Q$_{11}$)(Q$_{12}$), or any combination thereof;

a C$_3$-C$_{60}$ carbocyclic group, a C$_1$-C$_{60}$ heterocyclic group, a C$_6$-C$_{60}$ aryloxy group, or a C$_6$-C$_{60}$ arylthio group, each unsubstituted or substituted with deuterium, —F, —Cl, —Br, —I, a hydroxyl group, a cyano group, a nitro group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{60}$ carbocyclic group, a C$_1$-C$_{60}$ heterocyclic group, a C$_6$-C$_{60}$ aryloxy group, a C$_6$-C$_{60}$ arylthio group, —Si(Q$_{21}$)(Q$_{22}$)(Q$_{23}$), —B(Q$_{21}$)(Q$_{22}$), —C(=O)(Q$_{21}$), —S(=O)$_2$(Q$_{21}$), —P(=O)(Q$_{21}$)(Q$_{22}$), or any combination thereof; or —Si(Q$_{31}$)(Q$_{32}$)(Q$_{33}$), —B(Q$_{31}$)(Q$_{32}$), —C(=O)(Q$_{31}$), —S(=O)$_2$(Q$_{31}$), or —P(=O)(Q$_{31}$)(Q$_{32}$), Q$_1$ to Q$_3$, Q$_{11}$ to Q$_{13}$, Q$_{21}$ to Q$_{23}$, and Q$_{31}$ to Q$_{33}$ are each independently: hydrogen; deuterium; —F; —Cl; —Br; —I; a hydroxyl group; a cyano group; a nitro group; a C$_1$-C$_{60}$ alkyl group; a C$_2$-C$_{60}$ alkenyl group; a C$_2$-C$_{60}$ alkynyl group; a C$_1$-C$_{60}$ alkoxy group; or a C$_3$-C$_{60}$ carbocyclic group or a C$_1$-C$_{60}$ heterocyclic group, each unsubstituted or substituted with deuterium, —F, a cyano group, a C$_1$-C$_{60}$ alkyl group, a C$_1$-C$_{60}$ alkoxy group, a phenyl group, a biphenyl group, or any combination thereof, and

* and ** each indicate a binding site to a neighboring atom.

11. The light-emitting device of claim 10, wherein the first compound does not comprise a group represented by Formulae 2-1 to 2-3:

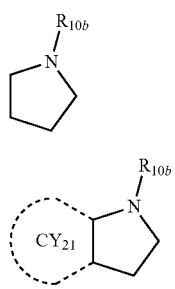

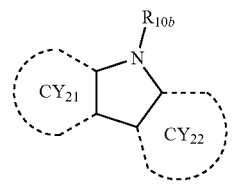

wherein, in Formulae 2-1 to 2-3,

CY$_{21}$ and CY$_{22}$ are each independently a C$_3$-C$_{20}$ carbocyclic group or a C$_1$-C$_{20}$ heterocyclic group, and R$_{10b}$ is the same as described in connection with R$_{10a}$.

12. The light-emitting device of claim 10, wherein the second compound is a carbazole-containing compound.

13. The light-emitting device of claim 10, wherein the second compound comprises a group represented by Formulae 2-1 to 2-3:

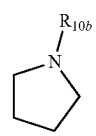

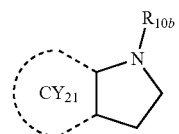

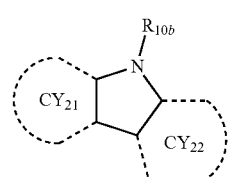

wherein, in Formulae 2-1 to 2-3,

CY$_{21}$ and CY$_{22}$ are each independently a C$_3$-C$_{20}$ carbocyclic group or a C$_1$-C$_{20}$ heterocyclic group, and R$_{10b}$ is the same as described in connection with R$_{10a}$.

14. The light-emitting device of claim 10, wherein CY$_1$ to CY$_4$, Ar$_1$, and Ar$_2$ are each independently a π electron-rich C$_3$-C$_{60}$ cyclic group unsubstituted or substituted with at least one R$_{10a}$.

15. An electronic apparatus comprising the light-emitting device of claim 1.

16. The electronic apparatus of claim 15, further comprising a thin-film transistor, wherein the thin-film transistor comprises a source electrode and a drain electrode, and the first electrode of the light-emitting device is electrically connected to the source electrode or the drain electrode of the thin-film transistor.

17. The electronic apparatus of claim 15, further comprising a color filter, a color conversion layer, a touch screen layer, a polarizing layer, or any combination thereof.

18. The electronic apparatus of claim 15, wherein the electronic apparatus is applied to a display, a light source, a lighting apparatus, a personal computer, a mobile personal computer, a mobile phone, a digital camera, an electronic diary, an electronic organizer, an electronic dictionary, an electronic game machine, a medical instrument, an electronic thermometer, a sphygmomanometer, a blood glucose meter, a pulse measurement device, a pulse wave measurement device, an electrocardiogram display, an ultrasonic diagnostic device, an endoscope display, a fish finder, a measuring instrument, a meter for a vehicle, a meter for an aircraft, a meter for a vessel, or a projector.

19. A light-emitting device comprising:
a first electrode;
a second electrode facing the first electrode; and
an interlayer comprising an emission layer between the first electrode and the second electrode and a hole transport region between the first electrode and the emission layer,
wherein the emission layer comprises a dopant,
the hole transport region comprises a first hole transport layer, a second hole transport layer between the first hole transport layer and the emission layer, and a third hole transport layer between the second hole transport layer and the emission layer,
the first hole transport layer comprises a first compound,
the second hole transport layer comprises a second compound,
the third hole transport layer comprises a third compound,
the first to third compounds are each independently an amine-based compound, and are different from each other, and
Equation 1 is satisfied:

$$T_1(HTM3) \geq T_1(D) + 0.3 \text{ eV, and} \qquad \text{Equation 1}$$

wherein, in Equation 1,
$T_1$(HTM3) is a triplet energy level in electron volt (eV) of the third compound,
$T_1$(D) is a triplet energy level in electron volt (eV) of the dopant, and
$T_1$(HTM3) and $T_1$(D) are values evaluated utilizing a density functional theory (DFT) method of a Gaussian program, which is structure-optimized at a B3LYP/6-31G(d,p) level,
wherein
the first electrode is patterned according to a first subpixel, a second subpixel, and a third subpixel,
the emission layer comprises a first emission layer that is formed in the first subpixel and is to emit a first-color light, a second emission layer that is formed in the second subpixel and is to emit a second-color light, and a third emission layer that is formed in the third subpixel and is to emit a third-color light,
the first hole transport layer and the second hole transport layer are common layers formed over all of the first subpixel, the second subpixel, and the third subpixel,
the third hole transport layer comprises a hole transport layer 3-1 formed in the first subpixel, a hole transport layer 3-2 formed in the second subpixel, and a hole transport layer 3-3 formed in the third subpixel,
the first emission layer comprises a first dopant,
the second emission layer comprises a second dopant,
the third emission layer comprises a third dopant,
the hole transport layer 3-1 comprises a first third compound,
the hole transport layer 3-2 comprises a second third compound,
the hole transport layer 3-3 comprises a third third compound,
the first third compound comprised in the hole transport layer 3-1, the second third compound comprised in the hole transport layer 3-2, and the third compound comprised in the hole transport layer 3-3 are identical to or different from each other, and
Equation 2 is satisfied:

$$T_1(HTM3\text{-}1) > T_1(D1);$$

$$T_1(HTM3\text{-}2) > T_1(D2); \text{ and}$$

$$T_1(HTM3\text{-}3) > T_1(D3), \qquad \text{Equation 2}$$

wherein, in Equation 2,
$T_1$(HTM3-1) is a triplet energy level in electron volt (eV) of the first third compound comprised in the hole transport layer 3-1,
$T_1$(HTM3-2) is a triplet energy level in electron volt (eV) of the second third compound comprised in the hole transport layer 3-2,
$T_1$(HTM3-3) is a triplet energy level in electron volt (eV) of the third third compound comprised in the hole transport layer 3-3,
$T_1$(D1) is a triplet energy level in electron volt (eV) of the first dopant,
$T_1$(D2) is a triplet energy level in electron volt (eV) of the second dopant,
$T_1$(D3) is a triplet energy level in electron volt (eV) of the third dopant, and
$T_1$(HTM3-1) to $T_1$(HTM3-3) and $T_1$(D1) to $T_1$(D3) are values evaluated utilizing the DFT method of the Gaussian program, which is structure-optimized at the B3LYP/6-31G(d,p) level.

20. The light-emitting device of claim 16, wherein Equation 2-1 is further satisfied:

$$T_1(HTM3\text{-}1) \geq T_1(D1) + 0.3 \text{ eV};$$

$$T_1(HTM3\text{-}2) \geq T_1(D2) + 0.3 \text{ eV}; \text{ and}$$

$$T_1(HTM3\text{-}3) \geq T_1(D3) + 0.3 \text{ eV}, \qquad \text{Equation 2-1}$$

wherein, in Equation 2-1, $T_1$(HTM3-1), $T_1$(HTM3-2), and $T_1$(HTM3-3) are each the same as described in connection with Equation 2.

* * * * *